United States Patent
Adams et al.

(10) Patent No.: US 12,102,644 B2
(45) Date of Patent: Oct. 1, 2024

(54) COMPOUNDS AND METHODS OF PROMOTING MYELINATION

(71) Applicant: Case Western Reserve University, Cleveland, OH (US)

(72) Inventors: Drew Adams, Cleveland, OH (US); Dharmaraja Allimuthu, Cleveland, OH (US); Zita Hubler, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 186 days.

(21) Appl. No.: 17/047,831

(22) PCT Filed: Apr. 17, 2019

(86) PCT No.: PCT/US2019/027833
§ 371 (c)(1),
(2) Date: Oct. 15, 2020

(87) PCT Pub. No.: WO2019/204411
PCT Pub. Date: Oct. 24, 2019

(65) Prior Publication Data
US 2021/0121481 A1    Apr. 29, 2021

Related U.S. Application Data

(60) Provisional application No. 62/658,886, filed on Apr. 17, 2019.

(51) Int. Cl.
| | | |
|---|---|---|
| A61K 31/575 | (2006.01) | |
| A61K 31/57 | (2006.01) | |
| A61K 31/573 | (2006.01) | |
| A61K 31/661 | (2006.01) | |
| A61P 25/28 | (2006.01) | |
| C07J 9/00 | (2006.01) | |
| C12N 5/079 | (2010.01) | |

(52) U.S. Cl.
CPC ............ *A61K 31/575* (2013.01); *A61K 31/57* (2013.01); *A61K 31/573* (2013.01); *A61K 31/661* (2013.01); *A61P 25/28* (2018.01); *C07J 9/00* (2013.01); *C12N 5/0622* (2013.01); *C12N 2501/999* (2013.01)

(58) Field of Classification Search
CPC .... A61K 31/575; A61K 31/57; A61K 31/573; A61K 31/661; A61P 25/28; C07J 9/00; C12N 5/0622; C12N 2501/999
See application file for complete search history.

(56) References Cited

U.S. PATENT DOCUMENTS

2018/0228743 A1* 8/2018 Tesar .................. A61K 38/215

FOREIGN PATENT DOCUMENTS

WO    2018/022904 A2    2/2018

OTHER PUBLICATIONS

Fernández et al. Medicine—Programa de Formación MédicaContinuada Acreditado vol. 11, Issue 77, Apr. 2015 , pp. 4601-4609 English Abstract only. (Year: 2015).*
Sakai Pathogenesis of leukodystrophy for Krabbe disease: Molecular mechanism and clinical treatment Brain & Development 31 (2009) 485-487. (Year: 2009).*
Sarah Crunkhorn Parkinson's drug promotes myelin repair Nature Reviews Drug Discovery vol. 12, p. 905 (2013) (Year: 2013).*
Cai and Xiao Oligodendrocytes and Alzheimer's disease International Journal of Neuroscience vol. 126, 2016—Issue 2 (Year: 2016).*
Hubler et al. Accumulation of 8,9-unsaturated sterols drives oligodendrocyte formation and remyelination Nature. Aug. 2018; 560(7718): 372-376. (Year: 2018).*
Xie et al. Clemastine Ameliorates Myelin Deficits via Preventing Senescence of Oligodendrocytes Precursor Cells in Alzheimer's Disease Model Mouse Front. Cell Dev. Biol., Oct. 21, 2021 (Year: 2021).*
Hubler et al., Accumulation of 8,9-unsaturated sterols drives oligodendrocyte formation and remyelination. Nature. Aug. 2018;560(7718):372-376.
International Search Report and Written Opinion for Application No. PCT/US2019/027833, dated Jul. 10, 2019, 9 pages.

* cited by examiner

*Primary Examiner* — Jeffrey S Lundgren
*Assistant Examiner* — William Y Lee
(74) *Attorney, Agent, or Firm* — McCarter & English, LLP; Yu Lu

(57) ABSTRACT

A method of promoting the generation of oligodendrocytes from oligodendrocyte precursor cells by enhancing their survival and/or maturation includes administering to the cell an effective amount of an agent that enhances and/or induces accumulation of 8,9-unsaturated sterols in the OPCs, the agent comprising a compound having the formula (I): wherein variables $Y^1$, $R^1$ and $R^2$ are as defined herein.

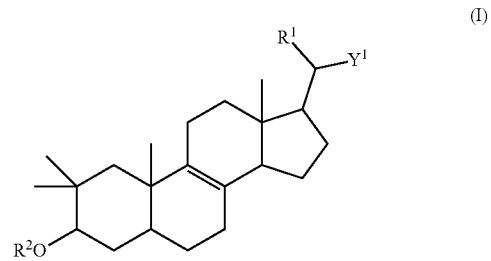

(I)

10 Claims, 29 Drawing Sheets

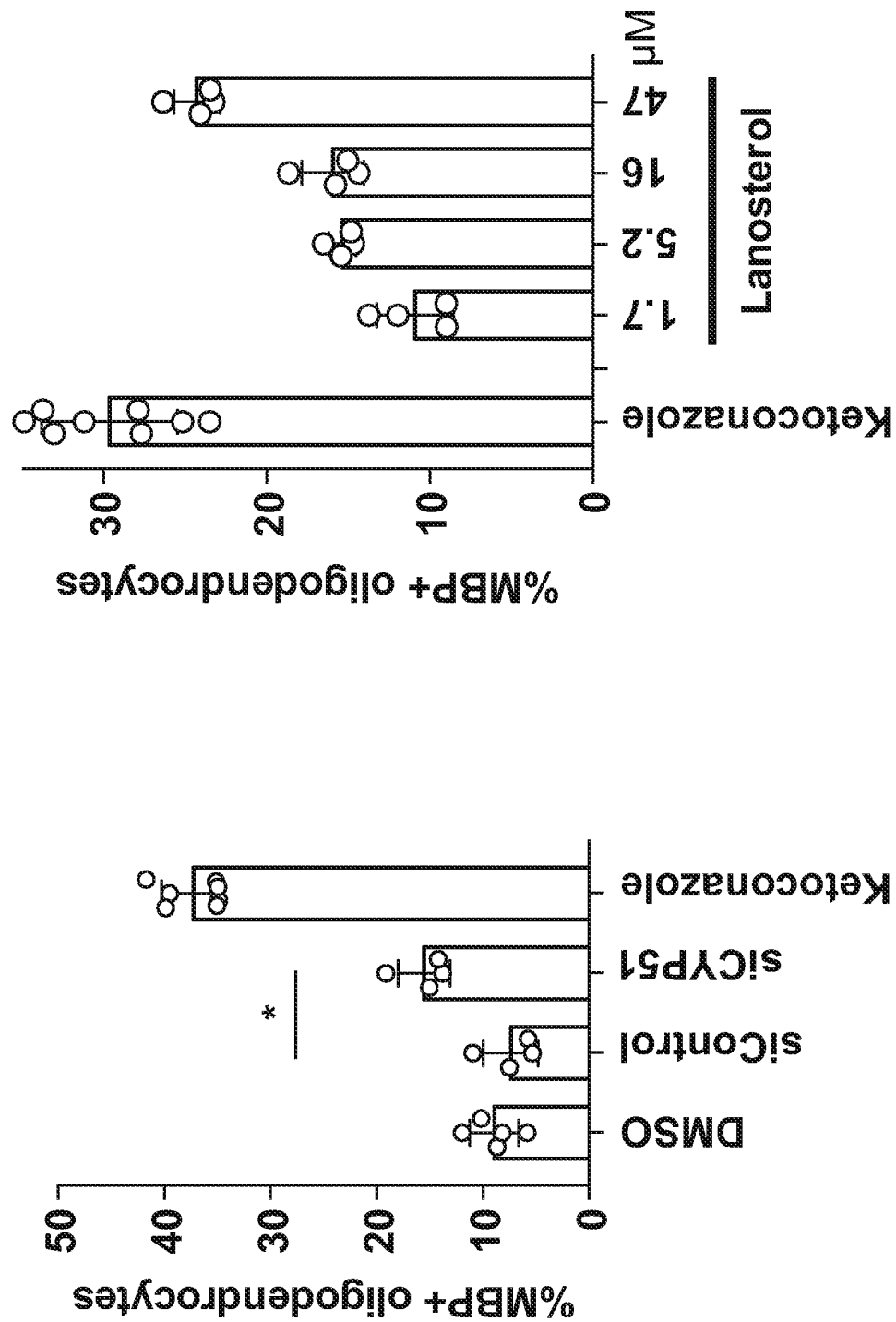

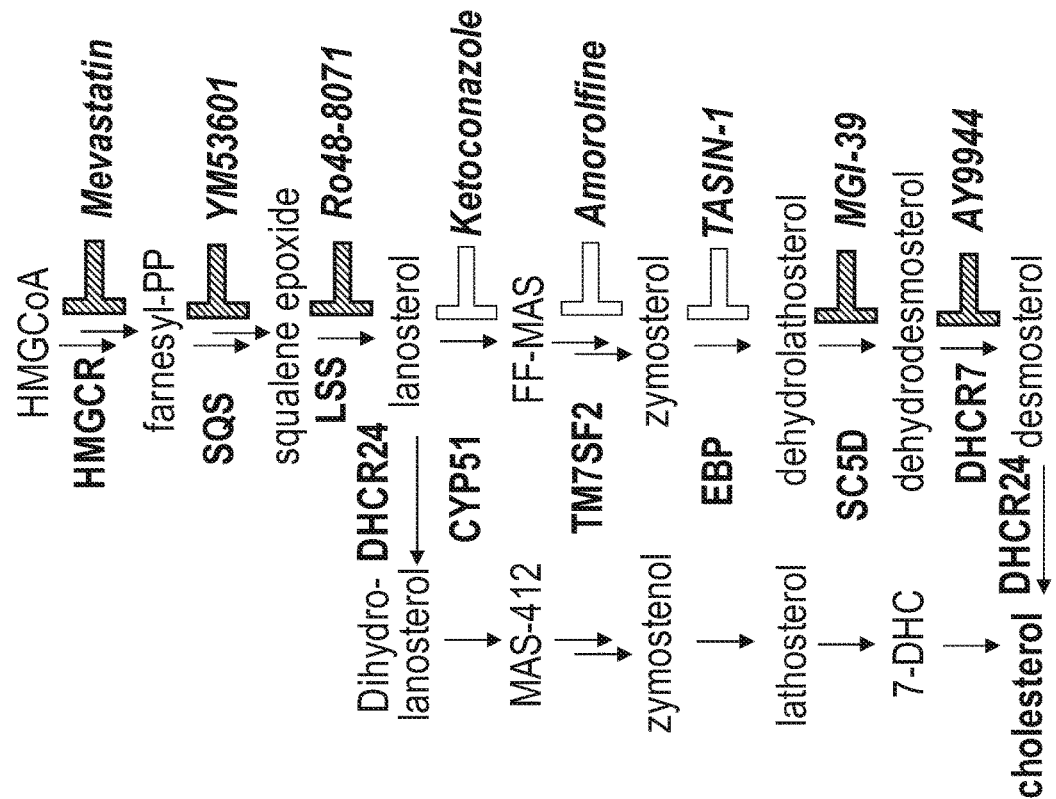
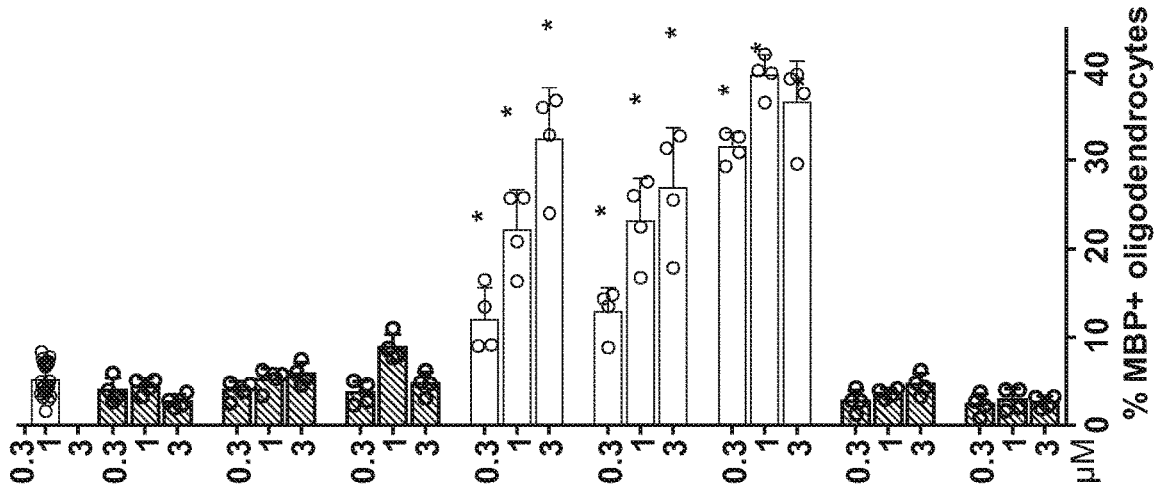
FIG. 2A
FIG. 2B sgNTC sgEBP

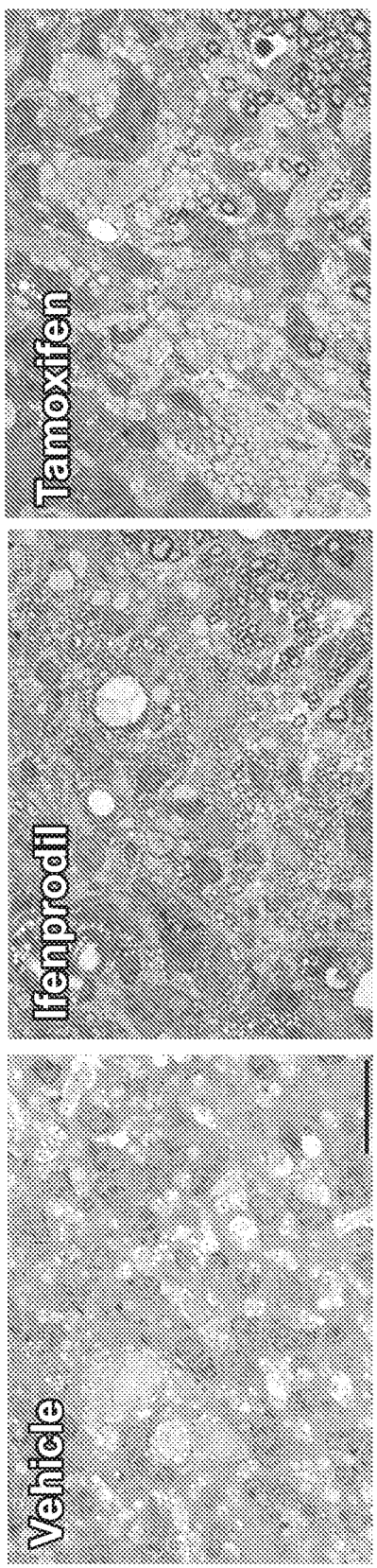

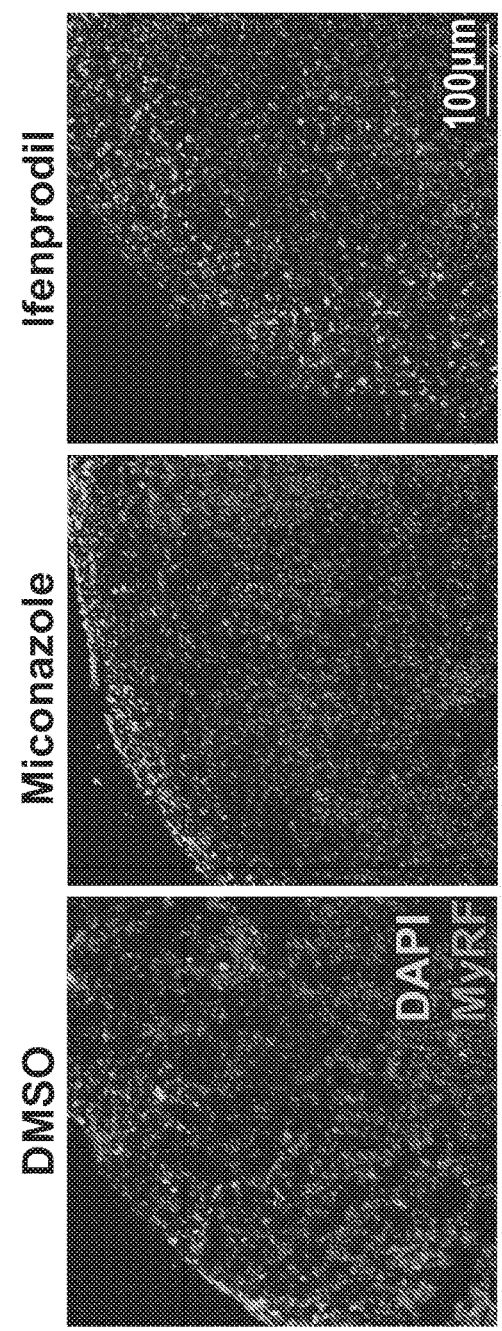
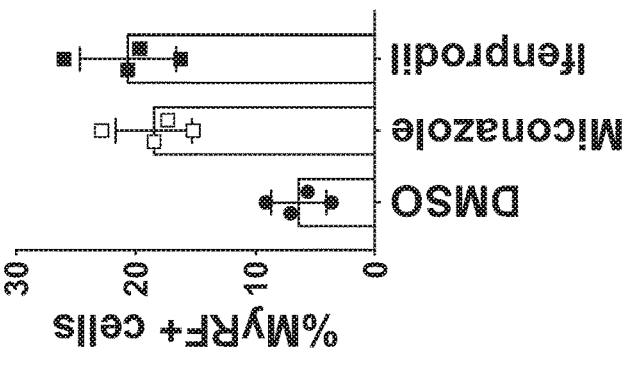
FIG. 4E
FIG. 4F

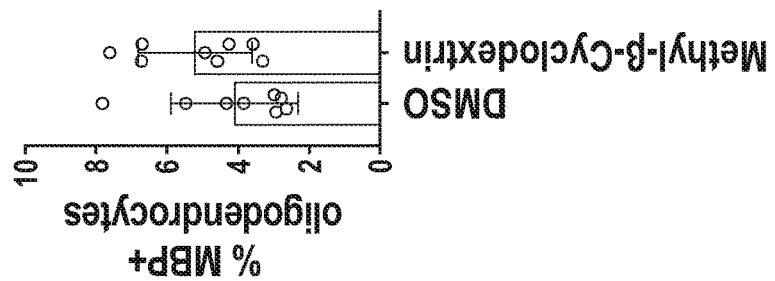
FIG. 5A
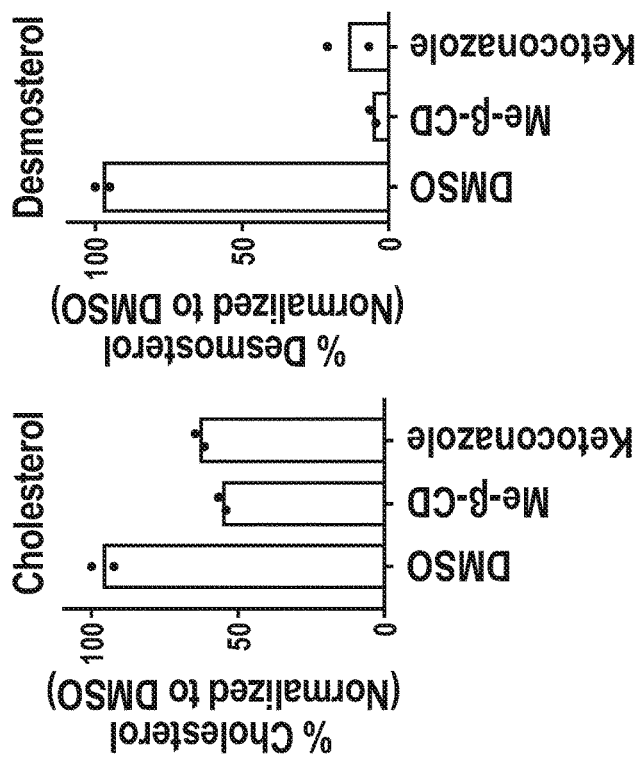
FIG. 5B
FIG. 5C
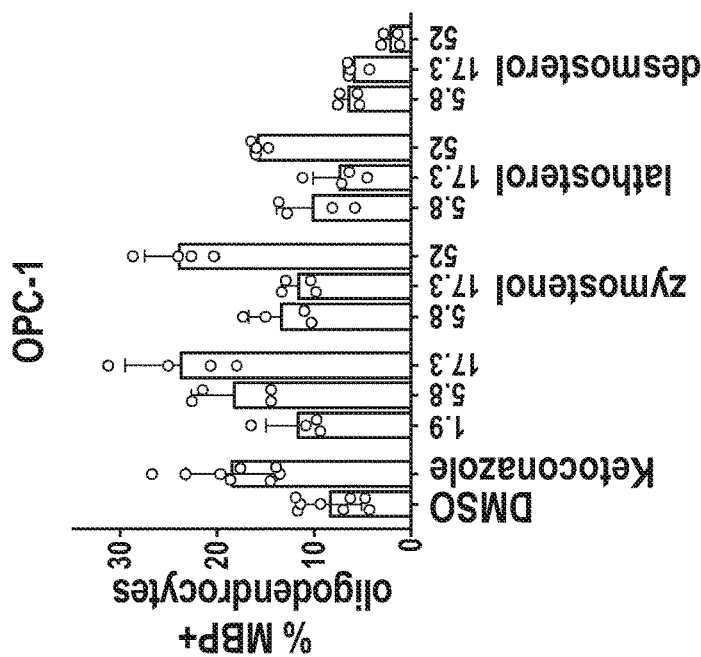

2,2-Me-Zymosterol

COMPOUNDS AND METHODS OF PROMOTING MYELINATION

CROSS REFERENCE TO RELATED APPLICATIONS

This application is a U.S. national stage filing, under 35 U.S.C. § 371(c), of International Application No. PCT/US2019/027833, filed on Apr. 17, 2019, which claims priority to U.S. Provisional Patent Application No. 62/658,886, filed Apr. 17, 2018, the disclosures and contents of which are incorporated herein by reference in their entireties.

GOVERNMENT FUNDING

This invention was made with government support under the grants CA043703 and NS095280, both awarded by the U.S. National Institutes of Health. The U.S. government has certain rights in the invention.

BACKGROUND

Multiple sclerosis (MS) is a complex neurological disease characterized by deterioration of central nervous system (CNS) myelin. This insulating material, composed in its majority by lipids (70% lipids, 30% protein), protects axons and makes possible the saltatory conduction, which speeds axonal electric impulse. Demyelination of axons in chronic MS may result in axon degeneration and neuronal cell death, but more specifically, MS destroys oligodendrocytes, the highly specialized CNS cells that generate and maintain myelin.

Oligodendrocyte precursors (PDGFRα+, NG2-proteoglycan+), the immature oligodendrocytes, are generated in ventral areas of the developing brain from a common glial progenitor, actively migrate and proliferate populating the CNS to finally differentiate to premyelinating oligodendrocytes (O4+). At this maturation point, oligodendrocytes both target and extend myelin sheaths along axons or they die. Less explored has been however, the hypothesis of enhanced myelination and/or remyelination by either endogenous oligodendrocyte precursors or transplanted cells.

Inducing differentiation and/or promoting survival during the maturation of endogenous oligodendrocyte progenitors can stimulate and enhance the generation of new oligodendrocytes and intrinsic myelination and/or remyelination. Therefore, there is a need for compounds and therapeutic methods capable of enhancing the generation of new oligodendrocytes.

SUMMARY

Embodiments described herein generally relate to agents, compounds, and methods for enhancing oligodendrocyte generation by inducing, promoting, and/or modulating oligodendrocyte precursor cell differentiation, proliferation and/or maturation as well as to methods for the treatment of disease or disorders in subjects where myelination or remyelination is beneficial to the subject.

It was found that the enhancement and/or inducement of the accumulation of Δ8,9-unsaturated sterols in OPCs is a central mechanism for enhancing oligodendrocyte generation and that the 8,9 double bond positioning of a sterol is an essential structural feature for efficacy in OPCs. Enhancement and/or inducement of the accumulation of 8,9-unsaturated sterols can be provided by directly and/or indirectly administering 8,9-unsaturated sterols to the OPCs. It was further found that in addition to naturally occurring sterols and sterol intermediates, non-natural 8,9-unsaturated sterols also enhance oligodendrocyte formation. Enhancement and/or inducement of the accumulation of 8,9-unsaturated sterols can promote OPC differentiation, survival, proliferation and/or maturation and treat diseases and/or disorders in subjects where myelination or remyelination is beneficial to the subject.

In some embodiments, an agent that enhances and/or induces accumulation of 8,9-unsaturated sterols in the OPCs can be administered to a subject and/or the OPCs at an amount effective to promote and/or induce OPC differentiation, proliferation and/or maturation as well as oligodendrocyte generation. In one example, the agent can include at least one non-natural 8,9-unsaturated sterol including a 2,2 dimethyl group having the formula (I):

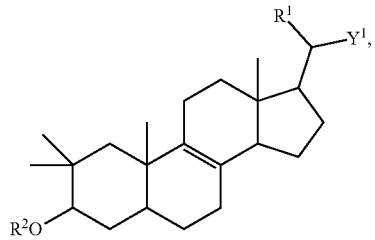

where (a) $R^1$ is —H or $(C_1-C_3)$ alkyl;
(b) $Y^1$ is a $(C_1-C_{10})$ substituted or unsubstituted straight chain or branched alkyl; and
(c) $R^2$ is either H or an acyl group, including sulphonyl group or phosphonyl group, or a group which comes together with the remaining part of the molecule forms an ether.

In some embodiments, the agent can include at least one compound having the formula (II):

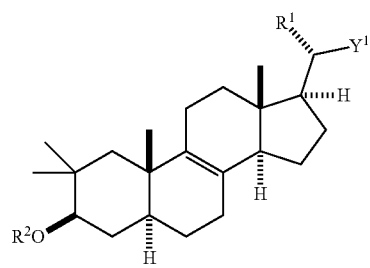

where (a): $R^1$ is —H or $(C_1-C_3)$ alkyl;
(b) $Y^1$ is a $(C_1-C_{10})$ substituted or unsubstituted straight chain or branched alkyl and
(c) $R^2$ is either H or an acyl group, including sulphonyl group or phosphonyl group, or a group which comes together with the remaining part of the molecule forms an ether.

In some embodiments, the agent can include at least one compound having the formula (III):

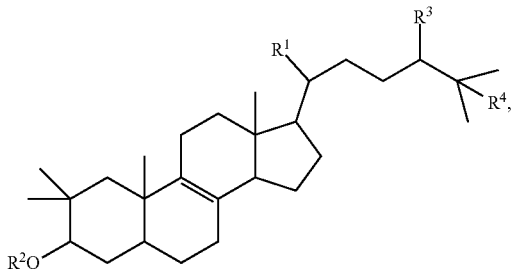

where (a) $R^1$ is —H or $(C_1\text{-}C_3)$ alkyl;
(b) $R^3$ and $R^4$ are hydrogen or together they designate an additional bond between the carbon atoms to which they are bound; and
(c) $R^2$ is either H or an acyl group, including sulphonyl group or phosphonyl group, or a group which comes together with the remaining part of the molecule forms an ether.

In some embodiments, the agent can include at least one compound having the formula (IV):

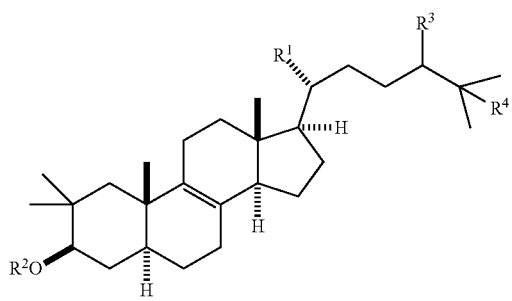

where (a) $R^1$ is —H or $(C_1\text{-}C_3)$ alkyl;
(b) $R^3$ and $R^4$ are hydrogen or together they designate an additional bond between the carbon atoms to which they are bound; and
(c) $R^2$ is either H or an acyl group, including sulphonyl group or phosphonyl group, or a group which comes together with the remaining part of the molecule forms an ether.

In some embodiments, the agent can include at least one compound having the formula (V):

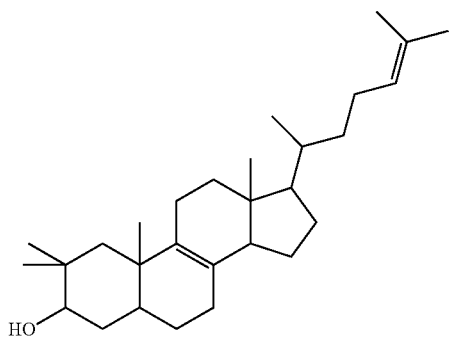 [SMILES: CC(C)=CCCC(C)C1CCC2C3=C(CCC21C)C1(C)CC(C)(C)C(O)CC1CC3]

derivatives, analogs, or pharmaceutically acceptable salts thereof.

In some embodiments, the agent can include at least one compound having the formula (VI):

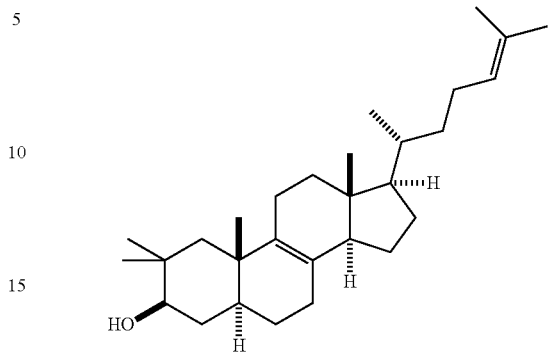

analogs and pharmaceutically acceptable salts thereof.

In some embodiments, the compounds described herein can be used to treat neurodegenerative diseases and disorders in a subject in need thereof. In some embodiments, the neurodegenerative disease or disorder is a myelin related disorder. Myelin related diseases or disorders include diseases, disorders or injuries which relate to dysmyelination or demyelination in a subject's neural cells, e.g., CNS neurons. Examples of myelin related diseases and disorders are multiple sclerosis (MS), neuromyelisits optica (NMO), progressive multifocal leukoencephalopathy (PML), encephalomyelitis (EPL), central pontine myelolysis (CPM), adrenoleukodystrophy, Alexander's disease, Pelizaeus Merzbacher disease (PMD), Vanishing White Matter Disease, Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, Bassen-Kornzweig syndrome, Marchiafava-Bignami syndrome, metachromatic leukodystrophy, trigeminal neuralgia, acute dissmeminated encephalitis, Guillian-Barre syndrome, Charcot-Marie-Tooth disease Bell's palsy, and mental health disorders such as schizophrenia.

DETAILED DESCRIPTION

Figure 1A:
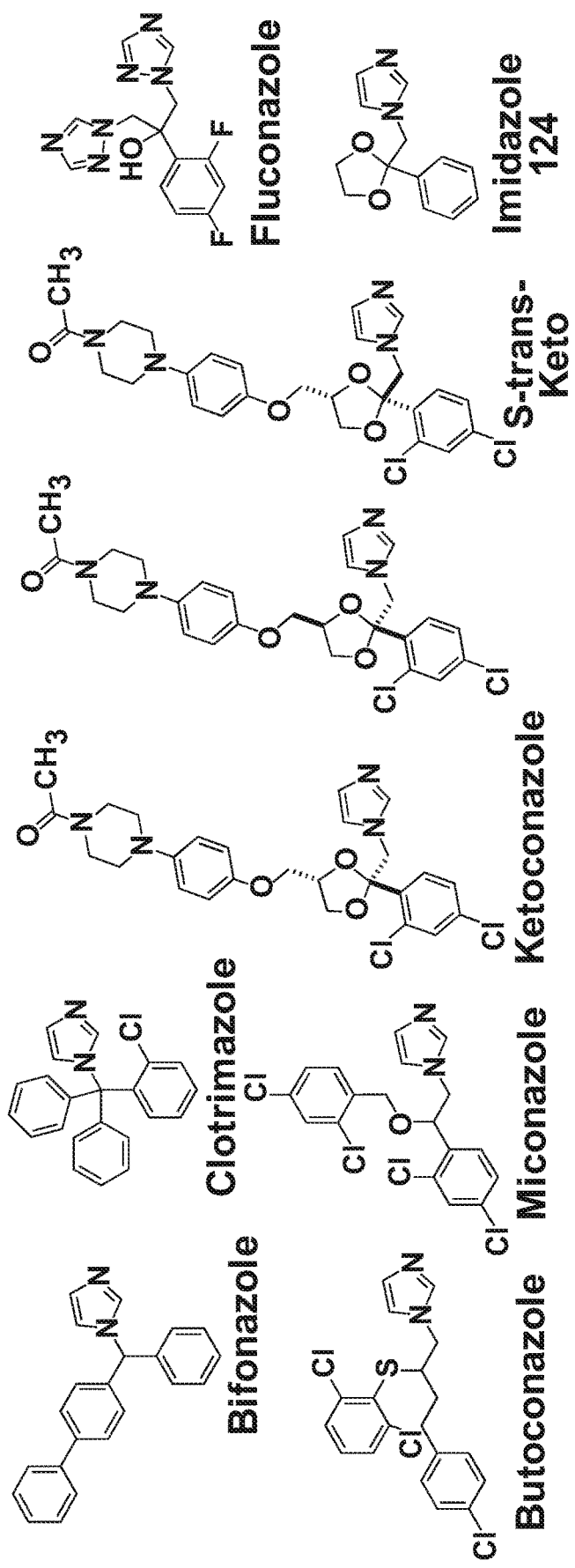
FIGS. 1(A-J) illustrate structures, plots, graphs, and images showing CYP51 is the functional target by which imidazole antifungals enhance oligodendrocyte formation. a) Azole molecules with varying degrees of potency for mammalian CYP51 inhibition. Throughout, green labels indicate molecules considered active, while red labels indicate inactive molecules. b) Rat CYP51 enzymatic activity following treatment with azoles as measured by LC/MS-based quantitation of the CYP51 product FF-MAS (4,4-dimethyl-5α-cholesta-8,14,24-trien-3β-ol). n=2 independent enzymatic assays. c) Percentage of MBP+ oligodendrocytes generated from OPCs at 72 h following treatment with azoles. n=4 replicates per condition, with >1,000 cells analyzed per replicate. *, $P<2\times10^{-5}$, (t-test). d) Representative images of OPCs treated 72 h with the indicated imidazole antifungals. Nuclei are labeled with DAPI (blue), and oligodendrocytes are indicated by immunostaining for myelin basic protein (green). All treatments are at the highest concentration shown in c. Scale bar, 100 μm. e) GC/MS-based quantitation of lanosterol levels in OPCs treated 24 h with the indicated azoles at 2.5 μM. n=2 replicates per condition. f) GC/MS-based quantitation of lanosterol levels in OPCs treated 24 h with the indicated doses of ketoconazole. n=2 replicates per condition. g) CYP51 mRNA levels measured by RT-qPCR following 4 d treatment with non-targeting or CYP51-targeting pools of cell-permeable siRNAs. n=2 replicates, with quadruplicate qPCR measurements per replicate. h) GC/MS-based quantitation of lanosterol levels in OPCs treated 96 h with the indicated reagents. n=2 replicates per condition, Ketoconazole, 2.5 μM. i) Percentage of MBP$^+$ oligodendrocytes generated from OPCs at 72 h following treatment with the indicated reagents. n=2 independent experiments, 4 replicates per condition, with >1,000 cells analyzed per replicate. Two-tailed t-test, **P<0.01 for siRNA groups compared with their respective non-targeting control-treated group. j) Percentage of MBP$^+$ oligodendrocytes generated from OPCs at 72 h following treatment with exogenous lanosterol. n=4 replicates per condition, with >1,000 cells analyzed per replicate. All bar graphs indicate mean+/−standard deviation, and findings in b-f and h-j are representative of two or more independent experiments. Cell-based experiments were performed in the OPC-5 derivation and have been confirmed in a second independent batch of OPCs (OPC-1).

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substituents, e.g., sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein. Typically a derivative is a compound that is derived from a similar compound by a chemical reaction.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed agents, in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl), N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p1-92, Elesevier, New York-Oxford (1985).

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, 3rd ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

The term "oligodendrocyte precursor cells" or "OPCs" as used herein refers to a neural progenitor cell capable to generate new oligodendrocyte cells. Oligodendrocyte precursor cells can be identified by the expression of a number of surface antigens. For example, the surface antigens known as platelet-derived growth factor-alpha receptor subunit (PDGFRα), NG2 chondroitin sulfate proteoglycan, and ganglioside GD3, are commonly used to identify oligodendrocyte precursor cells.

Immature oligodendrocyte precursors are generated in ventral areas of the developing brain from a common glial progenitor. The immature cells actively migrate, proliferate, and populate the CNS to finally differentiate to premyelinating oligodendrocytes (04+). Oligodendrocyte precursor differentiation and maturation is characterized by an extension of multiple processes, increase in cell body size and formation of myelin.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal such as, but not limited to, myelination disturbances, myelin deficiencies, myelin loss and ineffective myelin repair) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "$ED_{50}$" is art-recognized. In certain embodiments, $ED_{50}$ means the dose of a drug, which produces 50% of its maximum response or effect, or alternatively, the dose, which produces a pre-determined response in 50% of test subjects or preparations. The term "$LD_{50}$" is art-recognized. In certain embodiments, $LD_{50}$ means the dose of a drug, which is lethal in 50% of test subjects. The term "therapeutic index" is an art-recognized term, which refers to the therapeutic index of a drug, defined as $LD_{50}/ED_{50}$.

The terms "$IC_{50}$" or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and al kylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate.

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—CN), isocyano (—$N^+C^-$), cyanato (—O—CN), isocyanato (—$ON^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S— alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$O_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

Embodiments described herein generally relate to agents, compounds, and methods for enhancing oligodendrocyte generation by inducing, promoting, and/or modulating oligodendrocyte precursor cell differentiation, proliferation and/or maturation as well as to methods for the treatment of disease or disorders in subjects where myelination or remyelination is beneficial to the subject.

It was found that the enhancement and/or inducement of the accumulation of Δ8,9-unsaturated sterols in OPCs is a central mechanism for enhancing oligodendrocyte generation and that the 8,9 double bond positioning of a sterol is an essential structural feature for efficacy in OPCs. Enhancement and/or inducement of the accumulation of 8,9-unsaturated sterols can be provided by directly and/or indirectly administering 8,9-unsaturated sterols to the OPCs. It was further found that in addition to naturally occurring sterols and sterol intermediates, non-natural 8,9-unsaturated sterols also enhance oligodendrocyte formation. Enhancement and/or inducement of the accumulation of 8,9-unsaturated sterols can promote OPC differentiation, survival, proliferation and/or maturation and treat diseases and/or disorders in subjects where myelination or remyelination is beneficial to the subject.

In some embodiments, an agent that enhances and/or induces accumulation of 8,9-unsaturated sterols in the OPCs can be administered to a subject and/or the OPCs at an amount effective to promote and/or induce OPC differentiation, proliferation and/or maturation as well as oligodendrocyte generation. In one example, the agent can include at least one non-natural 8,9-unsaturated sterol including a 2,2 dimethyl group.

In some embodiments, compounds, which are capable of enhancing OPC differentiation via modulation and/or inhibition of the cholesterol biosynthesis pathway can be identified using a high-throughput small molecule screen (HTS) that is biased to select compounds that have both a high potency and low toxicity in mammal subjects and are able to promote oligodendrocyte precursor differentiation. The term "small molecule" as used herein refers to biologically active organic compounds of low molecular weight (e.g. <550 kDa) which may cross biological membranes and modulate intracellular processes.

The HTS can include a primary screen where small drug-like organic compounds (250-550 kDa) are added to cells seeded and incubated on a 96- or 384-well plate. The cells can then be visually screened for oligodendrocyte precursor morphology changes. In a secondary screen, differentiation and proliferation induced by selected compounds can be further validated by fluorescence microscopy. Further oligodendrocyte precursor proliferation and maturation in response to selected compounds can then be assessed by induction of myelin protein expression as determined by, for example, immunocytochemistry and western blot. Examples of assays that can be used in the primary and secondary screening are described in Najm et al. Nat Methods. 2011 Sep. 25; 8(11):957-62; Bai et al. Neurosci Bull. 2013 April; 29(2):239-50; Yang et al. Dev Biol. 2011 Feb. 1; 350(1):127-38; and Cho et al. Curr Neuropharmacol. 2007 March; 5(1): 19-33.

In some embodiments, the compounds can be further screened using a brain slice assay that assesses myelination the brains of mammals, (e.g., rats and mice). Such assays are described, for example, in Bai et al. Neurosci Bull. 2013 April; 29(2):239-50, Yang et al. Dev Biol. 2011 Feb. 1; 350(1):127-38, and Cho et al. Curr Neuropharmacol. 2007 March; 5(1): 19-33.

In other embodiments, the compounds can be screened using an in vivo assay that assesses remyelination and reduction of clinical severity in the MOG35-55-induced chronic experimental autoimmune encephalomyelitis (EAE) rodent model of multiple sclerosis.

In other embodiments, the compounds can be screened using an assay that assesses myelination in vivo in a lysolecithin-induced mouse model of focal demyelination. Such an assay is described, for example, in Mi, S et al., *Ann Neurol* 65, 304-325 (2009).

In certain embodiments, compounds identified that are capable of enhancing OPC differentiation can enhance or induce accumulation of 8,9-unsaturated sterols in OPCs. In some embodiments, the compounds can enhance or induce accumulation of 8,9-unsaturated sterols in OPCs at an amount effective to promote and/or induce oligodendrocyte precursor cell differentiation, proliferation and/or maturation. For example, the compounds can enhance accumulation of 8,9-unsaturated sterols in OPCs by at least 5%, 10%, 20%, 25%, 30%, 40%, 50%, 60%, 70%, 75%, 80%, 85%, 90%, 95%, 99% or more as compared to the amount of 8,9-unsaturated sterols accumulated in untreated OPCs or subject.

In some embodiments, the agent that enhances and/or induces accumulation of 8,9-unsaturated sterols in the OPCs used in the methods described herein can include at least one non-natural 8,9-unsaturated sterol including a 2,2 dimethyl group having the formula (I):

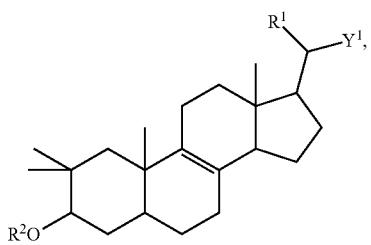

where (a) R is —H or ($C_1$-$C_3$) alkyl;
(b) $Y^1$ is a ($C_1$-$C_{10}$) substituted or unsubstituted straight chain or branched alkyl; and
(c) $R^2$ is either H or an acyl group, including sulphonyl group or phosphonyl group, or a group which comes together with the remaining part of the molecule forms an ether.

In some embodiments, $Y^1$ is ($C_1$-$C_{10}$) substituted with —$CO_2H$, —OH, —NH, —$SO_2$, $CF_3$, —$SO_3H$, —$PO_3H_2$, —$OSO_3H$, —F; or azole. In some embodiments, $R^1$ is $CH_3$. In certain embodiments $R^2$ is H.

In some embodiments, the agent can include at least one compound having the formula (II):

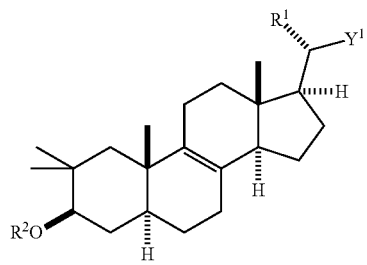

where (a): $R^1$ is —H or ($C_1$-$C_3$) alkyl;
(b) $Y^1$ is a ($C_1$-$C_{10}$) substituted or unsubstituted straight chain or branched alkyl and
(c) $R^2$ is either H or an acyl group, including sulphonyl group or phosphonyl group, or a group which comes together with the remaining part of the molecule forms an ether.

In some embodiments, $Y^1$ is ($C_1$-$C_{10}$) substituted with —$CO_2H$, —OH, —NH, —$SO_2$, $CF_3$, —$SO_3H$, —$PO_3H_2$, —$OSO_3H$, —F; or azole. In some embodiments, $R^1$ is $CH_3$. In certain embodiments $R^2$ is H.

In some embodiments, the agent can include at least one compound having the formula (III):

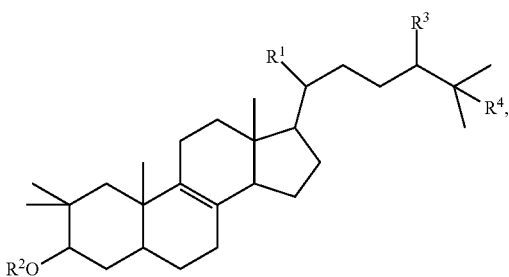

where (a) $R^1$ is —H or ($C_1$-$C_3$) alkyl;
(b) $R^2$ is either H or an acyl group, including sulphonyl group or phosphonyl group, or a group which comes together with the remaining part of the molecule forms an ether; and
(c) $R^3$ and $R^4$ are hydrogen or together they designate an additional bond between the carbon atoms to which they are bound.

In some embodiments, $R^1$ is $CH_3$. In certain embodiments $R^2$ is H. In some embodiments, $R^3$ and $R^4$ are H. In other embodiments, $R^3$ and $R^4$ together designate an additional bond between the carbon atoms to which they are bound.

In some embodiments, the agent can include at least one compound having the formula (IV):

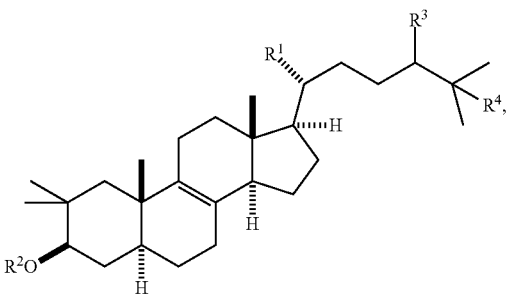

where (a) $R^1$ is —H or ($C_1$-$C_3$) alkyl;
(b) $R^2$ is either H or an acyl group, including sulphonyl group or phosphonyl group, or a group which comes together with the remaining part of the molecule forms an ether; and
(c) $R^3$ and $R^4$ are hydrogen or together they designate an additional bond between the carbon atoms to which they are bound.

In some embodiments, $R^1$ is $CH_3$. In certain embodiments $R^2$ is H. In some embodiments, $R^3$ and $R^4$ are H. In other embodiments, $R^3$ and $R^4$ together designate an additional bond between the carbon atoms to which they are bound.

In some embodiments, the agent can include at least one compound having the formula (V):

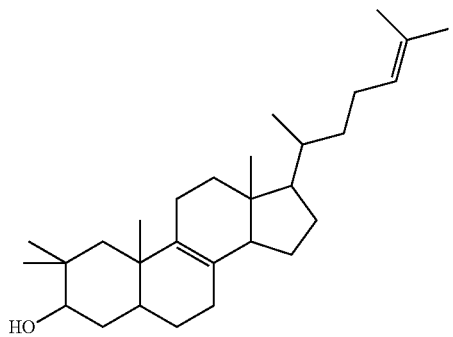 [SMILES: CC(C)=CCCC(C)C1CCC2C3=C(CCC21C)C1(C)CC(C)(C)C(O)CC1CC3]

derivatives, analogs, or pharmaceutically acceptable salts thereof.

In certain embodiments, the agent can include at least one compound having the formula (VI):

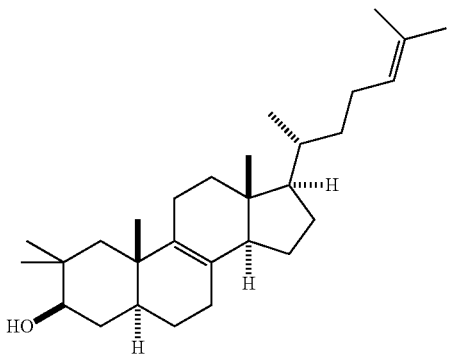 [SMILES: CC(C)=CCC[C@@H](C)[C@H]1CC[C@H]2C3=C(CC[C@]12C)[C@@]1(C)CC(C)(C)[C@H](O)C[C@@H]1CC3]

derivatives, analogs and pharmaceutically acceptable salts thereof.

Compounds described herein may be synthesized using standard synthetic techniques known to those of skill in the art or using methods known in the art in combination with methods described herein. In additions, solvents, temperatures and other reaction conditions presented herein may vary according to the practice and knowledge of those of skill in the art.

The starting material used for the synthesis of compounds described herein can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, ADVANCED ORGANIC CHEMISTRY $4^{th}$ Ed., (Wiley 1992); Carey and Sundberg, ADVANCED ORGANIC CHEMISTRY $4^{th}$ Ed., Vols. A and B (Plenum 2000, 2001), and Green and Wuts, PROTECTIVE GROUPS IN ORGANIC SYNTHESIS $3^{rd}$ Ed., (Wiley 1999) (all of which are incorporated by reference in their entirety).

Agents that enhance and/or induce accumulation of 8,9-unsaturated sterols in the OPCs described herein, can be provided and administered in the form of pharmaceutical compositions for the in vivo promotion of oligodendrocyte precursor differentiation and/or maturation. The pharmaceutical compositions can be administered to any subject that can experience the beneficial effects of the oligodendrocyte precursor differentiation and/or maturation compounds of the present invention. Foremost among such animals are humans, although the present invention is not intended to be so limited.

Pharmaceutical compositions for use in the methods of the present invention preferably have a therapeutically effective amount of the compound or salts thereof in a dosage in the range of 0.01 to 1,000 mg/kg of body weight of the subject, and more preferably in the range of from about 10 to 100 mg/kg of body weight of the patient.

The overall dosage will be a therapeutically effective amount depending on several factors including the overall health of a subject, the subject's disease state, severity of the condition, the observation of improvements and the formulation and route of administration of the selected agent(s). Determination of a therapeutically effective amount is within the capability of those skilled in the art. The exact formulation, route of administration and dosage can be chosen by the individual physician in view of the subject's condition.

The present invention provides a method of treating diseases in a subject by promoting the differentiation and/or proliferation of oligodendrocyte precursors in a subject. The method includes administering to the subject in need thereof a therapeutically effective amount of a pharmaceutical compound in accordance with the present invention. As described above, one or more of the compounds can be administered in association with one or more non-toxic, pharmaceutically acceptable carriers and/or diluents and/or adjuvants and if desired other active ingredients.

The "therapeutically effective amount" of compounds and salts thereof used in the methods of the present invention varies depending upon the manner of administration, the age and body weight of the subject, and the condition of the subject to be treated, and ultimately will be decided by those skilled in the art. The term "therapeutically effective amount" refers to an amount (dose) effective in treating a subject, having, for example, a neurodegenerative disease (e.g. multiple sclerosis).

In certain embodiments, compounds described herein may be administered in an amount effective to promote myelination of CNS neurons in a subject by an increase in the amount of myelin proteins (e.g., MBP) of at least 5%, 10%, 20%, 25%, 30%, 40%, 50%, 60%, 70%, 75%, 80%, 85%, 90%, 95%, 100%, 110%, 120%, 130%, 140%, 150%, 160%, 170%, 180%, 190%, 200%, 250%, 300%, 350%, 400%, 450%, 500%, 550%, 600%, 650%, 700%, 750%, 800%, 850%, 900%, 950%, or 1000% as compared to the level of myelin proteins of an untreated CNS neurons or subject.

In other embodiments, compounds described herein may be administered in an amount effective to promote survival of CNS neurons in a subject by an increase in the number of surviving neurons of at least 5%, 10%, 20%, 25%, 30%, 40%, 50%, 60%, 70%, 75%, 80%, 85%, 90%, 95%, 100%, 110%, 120%, 130%, 140%, 150%, 160%, 170%, 180%, 190%, 200%, 250%, 300%, 350%, 400%, 450%, 500%, 550%, 600%, 650%, 700%, 750%, 800%, 850%, 900%, 950%, or 1000% as compared to the number of surviving neurons in an untreated CNS neurons or subject.

In some embodiments, compounds described herein may be administered in an amount effective enhance generation of OPCs in the subject's central nervous system by an increase in the amount of OPC generation of at least 5%, 10%, 20%, 25%, 30%, 40%, 50%, 60%, 70%, 75%, 80%, 85%, 90%, 95%, 100%, 110%, 120%, 130%, 140%, 150%, 160%, 170%, 180%, 190%, 200%, 250%, 300%, 350%, 400%, 450%, 500%, 550%, 600%, 650%, 700%, 750%, 800%, 850%, 900%, 950%, or 1000% as compared to the amount of OPC generation in untreated OPCs or subject.

In some embodiments, compounds described herein may be administered in an amount effective to induce endogenous oligodendrocyte precursor cell (OPC) differentiation in the subject's central nervous system by an increase in the amount of OPC differentiation of at least 5%, 10%, 20%, 25%, 30%, 40%, 50%, 60%, 70%, 75%, 80%, 85%, 90%, 95%, 100%, 110%, 120%, 130%, 140%, 150%, 160%, 170%, 180%, 190%, 200%, 250%, 300%, 350%, 400%, 450%, 500%, 550%, 600%, 650%, 700%, 750%, 800%, 850%, 900%, 950%, or 1000% as compared to the amount of OPC differentiation in untreated OPCs or subject.

In some embodiments, compounds described herein may be administered in an amount effective to modulate the cholesterol biosynthesis pathway in a OPC cells in a subject by a decrease in the amount of cholesterol and/or one or more sterol intermediates synthesis in OPCs of at least 5%, 10%, 20%, 25%, 30%, 40%, 50%, 60%, 70%, 75%, 80%, 85%, 90%, 95%, or 99% as compared to the amount of cholesterol and/or one or more sterol intermediates synthesis in untreated OPCs or subject.

"Treating" or "treatment" as used herein, refers to the reduction in severity and/or frequency of symptoms, elimination of symptoms and/or underlying cause, prevention of the occurrence of symptoms and/or their underlying cause, and improvement or remediation of disease. Such treatment need not necessarily completely ameliorate the disease. For example, treatment of a subject with a neurodegenerative disease by administration of oligodendrocyte precursor differentiation compounds of the present invention can encompass inhibiting or causing regression of the disease. Further, such treatment can be used in conjunction with other traditional treatments for neurodegenerative diseases known to those of skill in the art.

The pharmaceutical compositions of the present invention can be administered to a subject by any means that achieve their intended purpose. For example, administration can be by parenteral, subcutaneous, intravenous, intraarticular, intrathecal, intramuscular, intraperitoneal, or intradermal injections, or by transdermal, buccal, oromucosal, ocular routes or via inhalation. Alternatively, or concurrently, administration can be by the oral route.

Formulation of the pharmaceutical compounds for use in the modes of administration noted above (and others) are known in the art and are described, for example, in Remington's Pharmaceutical Sciences (18th edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y., U.S.A., 2005; and Mathiowitz et al., eds., Bioadhesive Drug Delivery Systems, Drugs and the Pharmaceutical Sciences Series, Marcel Dekker, Inc., N.Y., U.S.A., 1999. Compounds of the invention can be formulated into pharmaceutical compositions containing pharmaceutically acceptable non-toxic excipients and carriers. The excipients are all components present in the pharmaceutical formulation other than the active ingredient or ingredients. Suitable excipients and carriers useful in the present invention are composed of materials that are considered safe and effective and may be administered to an individual without causing undesirable biological side effects, or unwanted interactions with other medications. Suitable excipients and carriers are those, which are composed of materials that will not affect the bioavailability and performance of the agent. As generally used herein "excipient" includes, but is not limited to surfactants, emulsifiers, emulsion stabilizers, emollients, buffers, solvents, dyes, flavors, binders, fillers, lubricants, and preservatives. Suitable excipients include those generally known in the art such as the "Handbook of Pharmaceutical Excipients", 4th Ed., Pharmaceutical Press, 2003.

The compounds can be administered to a subject to treat neurodegenerative diseases and disorders. A neurodegenerative disease, as contemplated for treatment by methods of the present invention, can arise from but is not limited to an inherited genetic abnormality, stroke, heat stress, head and spinal cord trauma (blunt or infectious pathology), and/or bleeding that occurs in the brain.

The neurodegenerative disease contemplated for treatment by some aspects of the present invention can include a myelin related disorder. Myelin disorders can include any disease, condition (e.g., those occurring from traumatic spinal cord injury and cerebral infarction), or disorder related to demyelination, insufficient myelination and remyelination, or dysmyelination in a subject. A myelin related disorder as used herein can arise from a myelination related disorder or demyelination resulting from a variety of neurotoxic insults. "Demyelination" as used herein, refers to the act of demyelinating, or the loss of the myelin sheath insulating the nerves, and is the hallmark of some neurodegenerative autoimmune diseases, including multiple sclerosis, transverse myelitis, chronic inflammatory demyelinating polyneuropathy, and Guillain-Barre Syndrome. Leukodystrophies are caused by inherited enzyme deficiencies, which cause abnormal formation, destruction, and/or abnormal turnover of myelin sheaths within the CNS white matter. Both acquired and inherited myelin disorders share a poor prognosis leading to major disability. Thus, some embodiments of the present invention can include methods for the treatment of neurodegenerative autoimmune diseases in a subject. Remyelination of neurons requires oligodendrocytes. The term "remyelination", as used herein, refers to the re-generation of the nerve's myelin sheath by replacing myelin producing cells or restoring their function.

Myelin related diseases or disorders which may be treated or ameliorated by the methods of the present invention include diseases, disorders or injuries which relate to dysmyelination or demyelination in a subject's brain cells, e.g., CNS neurons. Such diseases include, but are not limited to, diseases and disorders in which the myelin which surrounds the neuron is either absent, incomplete, not formed properly, or is deteriorating. Such disease include, but are not limited to, multiple sclerosis (MS), neuromyelisits optica (NMO), progressive multifocal leukoencephalopathy (PML), encephalomyelitis (EPL), central pontine myelolysis (CPM), adrenoleukodystrophy, Alexander's disease, Pelizaeus Merzbacher disease (PMD), Vanishing White Matter Disease, Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, Bassen-Kornzweig syndrome, Marchiafava-Bignami syndrome, metachromatic leukodystrophy, trigeminal neuralgia, acute dissmeminated encephalitis, Guillian-Barre syndrome, Charcot-Marie-Tooth disease Bell's palsy, and mental health disorders such as schizophrenia.

In some embodiments, myelin related diseases or disorders which may be treated or ameliorated by the methods of the present invention include leukodystrophies. Leukodystrophies are a group of progressive, metabolic, genetic diseases that affect the brain, spinal cord and often the peripheral nerves. Each type of leukodystrophy is caused by a specific gene abnormality that leads to abnormal development or destruction of the myelin sheath of the brain. Each type of leukodystrophy affects a different part of the myelin sheath, leading to a range of neurological problems. Exemeplary leukodystrophies which may be treated or ameliorated by the methods of the present invention include, but are not limited to, adult-onset autosomal dominant leukodystrophy (ADLD), Aicardi-Goutieres syndrome, Alexander disease, CADASIL, Canavan disease, CARASIL, cerebrotendionous xanthomatosis, childhood ataxia and cerebral ypomyelination (CACH)/vanishing white matter disease (VWMD), Fabry disease, fucosidosis, GM1 gangliosidosis, Krabbe disease, L-2-hydroxyglutaric aciduria, megalencephalic leukoencephalopathy with subcortical cysts, metachromatic leukodystrophy, multiple sulfatase deficiency, Pelizaeus-Merzbacher disease (PMD), Pol III-related leukodystrophies, Refsum disease, salla disease (free sialic acid storage disease), Sjogren-Larsson syndrome, X-linked adrenoleukodystrophy, and Zellweger syndrome spectrum disorders.

Myelin related diseases or disorders which may be treated or ameliorated by the methods of the present invention include a disease or disorder characterized by a myelin deficiency. Insufficient myelination in the central nervous system has been implicated in a wide array of neurological disorders. Among these are forms of cerebral palsy in which a congenital deficit in forebrain myelination in children with periventricular leukomalacia, contributes to neurological morbidity (Goldman et al., 2008) Goldman, S. A., Schanz, S., and Windrem, M. S. (2008). Stem cell-based strategies for treating pediatric disorders of myelin. Hum Mol Genet. 17, R76-83. At the other end of the age spectrum, myelin loss and ineffective repair may contribute to the decline in cognitive function associated with senescence (Kohama et al., 2011) Kohama, S. G., Rosene, D. L., and Sherman, L. S. (2011) Age (Dordr). Age-related changes in human and non-human primate white matter: from myelination disturbances to cognitive decline. Therefore, it is contemplated that effective compounds and methods of enhancing myelination and/or remyelination may have substantial therapeutic benefits in halting disease progression and restoring function in MS and in a wide array of neurological disorders.

In some embodiments, the compounds of the present invention can be administered to a subject that does not have, and/or is not suspected of having, a myelin related disorder in order to enhance or promote a myelin dependent process. In some embodiments, compounds described herein can be administered to a subject to promote myelination of CNS neurons in order to enhance cognition, which is known to be a myelin dependent process, in cognitive healthy subjects. In certain embodiments, compounds described herein can be administered in combination with cognitive enhancing (nootropic) agents. Exemplary agents include any drugs, supplements, or other substances that improve cognitive function, particularly executive functions, memory, creativity, or motivation, in healthy individuals. Non limiting examples include racetams (e.g., piracetam, oxiracetam, and aniracetam), nutraceuticals (e.g., bacopa monnieri, panax ginseng, ginko biloba, and GABA), stimulants (e.g., amphetamine pharmaceuticals, methylphenidate, eugeroics, xanthines, and nicotine), L-Theanine, Tolcapone, Levodopa, Atomoxetine, and Desipramine.

One particular aspect of the present invention contemplates the treatment of multiple sclerosis in a subject. The method includes administering to the subject a therapeutically effective amount of one or more oligodendrocyte differentiation promoting compound(s) described above.

Multiple sclerosis (MS) is the most common demyelinating disease. In multiple sclerosis, the body's failure to repair myelin is thought to lead to nerve damage, causing multiple sclerosis associated symptoms and increasing disability. The demyelination observed in MS is not always permanent and remyelination has been documented in early stages of the disease. It is contemplated that methods of the present invention can promote oligodendrocyte precursor cell differentiation in a subject, therefore leading to endogenous remyelination.

Another particular aspect of the present invention contemplates the treatment of a genetic myelin disorder which results from the loss of myelin (demyelination) in a subject. The method includes administering to the subject a therapeutically effective amount of one or more agents(s) that enhance and/or induce accumulation of Δ8,9-unsaturated sterol intermediates of the cholesterol biosynthesis pathway in OPCs described above. In certain embodiments, the genetic myelin disorder is a leukodystrophy such as, but not limited to Pelizaeus Merzbacher Disease (PMD)

Another strategy for treating a subject suffering from a neurodegenerative disease or disorder is to administer a therapeutically effective amount of a compound described herein along with a therapeutically effective amount of additional oligodendrocyte differentiation and/or proliferation inducing agent(s) and/or anti-neurodegenerative disease agent. Examples of anti-neurodegenerative disease agents include L-dopa, cholinesterase inhibitors, anticholinergics, dopamine agonists, steroids, and immunomodulators including interferons, monoclonal antibodies, and glatiramer acetate.

Therefore, in a further aspect of the invention, the oligodendrocyte precursor differentiation and/or proliferation inducing compounds described herein can be administered as part of a combination therapy with adjunctive therapies for treating neurodegenerative and myelin related disorders.

The phrase "combination therapy" embraces the administration of the oligodendrocyte precursor differentiation inducing compounds described herein and a therapeutic agent as part of a specific treatment regimen intended to provide a beneficial effect from the co-action of these therapeutic agents. When administered as a combination, the oligodendrocyte precursor differentiation inducing compound and a therapeutic agent can be formulated as separate compositions. Administration of these therapeutic agents in combination typically is carried out over a defined time period (usually minutes, hours, days or weeks depending upon the combination selected).

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (e.g., surgery).

In another aspect of the invention, the therapeutic agents administered in a combination therapy with the oligodendrocyte differentiation and/or proliferation inducing compounds described herein can include at least one anti-neurodegenerative agent such as but not limited to, an immunotherapeutic agent.

An immunotherapeutic agent for use in the methods of the present invention can include therapies which target the immune component of the disease and/or the acute inflammatory response evidenced during an acute attack in remitting-relapsing multiple sclerosis. Examples include, but are not limited to immunomodulators such as interferon beta-1a and beta-1b (Avonex and Betaseron respectively), natalizumab (Copaxone) natalizumab (Tysabri), glatiramer acetate (Copaxone) or mitoxantrone.

The invention is further illustrated by the following example, which is not intended to limit the scope of the claims.

EXAMPLE

Regeneration of myelin is mediated by oligodendrocyte progenitor cells (OPCs), an abundant stem cell population in the CNS and the principal source of new myelinating oligodendrocytes. Loss of myelin-producing oligodendrocytes in the central nervous system (CNS) underlies a number of neurological diseases, including multiple sclerosis (MS) and diverse genetic diseases. Using high throughput chemical screening approaches, the inventors have identified small molecules that promote myelination by stimulating oligodendrocyte formation from OPCs, and functionally enhance remyelination in vivo. Here the inventors demonstrate using chemical and genetic approaches that a broad range of these pro-myelinating small molecules function not through their canonical targets but by directly inhibiting CYP51 (cytochrome P450, family 51), sterol 14-reductase, or EBP (emopamil binding protein), a narrow range of enzymes within the cholesterol biosynthesis pathway. The inventors show that intracellular accumulation of the 8,9-unsaturated sterol substrates of these enzymes is the direct mechanism underlying enhanced oligodendrocyte formation, as 8,9-unsaturated sterols are effective when supplied to OPCs in purified form while analogous sterols lacking this structural feature have no effect. Functional studies showed that small molecule inhibitors of CYP51, sterol 14-reductase, and EBP induce accumulation of 8,9-unsaturated sterols in human cortical spheroids in vitro and mouse brain tissue in vivo. At the same doses, these molecules also enhance the formation of human oligodendrocytes and the rate of myelination in vivo in a lysolecithin-induced mouse model of focal demyelination. Collectively, the results described herein provide a unifying sterol-based mechanism-of-action for most known small-molecule enhancers of oligodendrocyte formation and highlight specific targets for the development of optimal remyelinating therapeutics.

Methods

No statistical methods were used to predetermine sample size.

Small Molecules

The identity and purity of small molecules were authenticated by LC/MS before use. The following compounds were purchased from Sigma-Aldrich as a solid: Ketoconazole, Miconazole, Clotrimazole, Fluconazole, Fulvestrant, Ifenprodil, Benztropine, Liothyronine, Bexarotene, Tamoxifen, Ospemifene, GSK343, Trans-U50488 and Cholesterol. The following compounds were purchased from Cayman Chemicals as a solid: Clemastine, AY9944, YM53601 and Ro-48-8071. The following compounds were obtained from Janssen Pharmaceuticals as a solid: R-trans-Ketoconazole, and S-trans-Ketoconazole. Mevastatin was purchased as a solid from Selleck Chemicals. The following compounds were purchased from Selleck Chemicals as a 10 mM DMSO solution: Bifonazole, Butoconazole, Amorolfine, Toremifene, EPZ005687, EPZ6438, UNC1999, Hydroxyzine, Ziprasidone, p-Fluorohexahydro-sila-difenidol (abbreviated in figures as Sigma $H_{127}$), Vesamicol, Raloxifene, L-745,870, TMB-8, Pramoxine, Varespladib, Tanshinone-I, Levofloxacin, Nateglinide, Abiraterone, Allopurinol, Detomidine, Rivastigmine, Beta carotene, BEZ-235, Scopolamine, and Homatropine. Pirenzepine and Telenzepine were purchased from Sigma-Aldrich as a 10 mM DMSO solution. Cholesterol biosynthetic intermediates were purchased from Avanti Polar Lipids as a solid: Lanosterol, Zymosterol, Zymostenol, Lathosterol, Desmosterol, 7-dehydrodesmosterol and T-MAS. 14-dehydrozymostenol (cholesta-8,14-dien-j-ol) was provided by Franz Bracher, Ludwig-Maximilians University of Munich. Imidazole 124, TASIN-1, and MGI39 were synthesized as reported.

Mouse OPC Preparation

To rigorously assess effects of small molecule and genetic treatments on OPCs, all treatments were assayed in two batches of epiblast stem cell-derived OPCs, and key results were confirmed using mouse primary OPCs. OPCs were generated from two separate EpiSC lines, EpiSC5 (giving rise to OPC-5 OPCs) and 12901 (giving rise to OPC-1 OPCs). Unless otherwise noted, results in OPC-5 cells are presented in FIGS. 1-4 while results in OPC-1 are presented in FIG. 5-11.

EpiSC-derived OPCs were obtained using in vitro differentiation protocols and culture conditions described previously. To ensure uniformity throughout all in vitro screening experiments, EpiSC-derived OPCs were sorted to purity by fluorescence activated cell sorting at passage five with conjugated CD 140a-APC (eBioscience, 17-1401; 1:80) and NG2-AF488 (Millipore, AB5320Δ4; 1:100) antibodies. Sorted batches of OPCs were expanded and frozen down in aliquots. OPCs were thawed into growth conditions for one passage before use in further assays. Cultures were regularly tested and shown to be *mycoplasma* free.

To obtain mouse primary OPCs, whole brain was removed from post-natal day 2 pups anesthetized on ice. Brains were placed in cold DMEM/F12, and the cortices were isolated and the meninges were removed. The cortices were manually chopped and processed with the Tumor Dissociation Kit (Miltenyi) and incubated at 37° C. for 10 minutes. The cell suspension was filtered through a 70 μM filter and centrifuged at 200×g for 4 minutes at room temperature. The cells were washed in DMEM/F12, re-centrifuged and plated in poly-Ornithine and Laminin-treated flasks containing DMEM/F12 supplemented with N2 Max, B27 (ThermoFisher), 20 ng/mL FGF, and 20 ng/mL PDGF. Small molecules were passaged once prior to treatment. Media was changed every 48 hours.

In Vitro Phenotypic Screening of OPCs

EpiSC-derived OPCs were grown and expanded in poly-ornithine (PO) and laminin-coated flasks with growth medium (DMEM/F12 supplemented with N2-MAX (R&D Systems), B-27 (ThermoFisher), GlutaMax (Gibco), FGF2 (10 μg/mL, R&D systems, 233-FB-025) and PDGF-AA (10 μg/mL, R&D systems, 233-AA-050) before harvesting for plating. The cells were seeded onto poly-D-lysine 96-well CellCarrier plates (PerkinElmer) coated with laminin (Sigma, L2020; 15 µg/ml) using multi-channel pipet. For the experiment, 800,000 cells/mL stock in differentiation medium (DMEM/F12 supplemented with N2-MAX and B-27) was prepared and stored on ice for 2 h. Then, 40,000 cells were seeded per well in differentiation medium and allowed to attach for 30 min before addition of drug. For dose-response testing of all molecules except sterols, a 1000× compound stock in dimethyl sulphoxide (DMSO) was added to assay plates with 0.1 µL solid pin multi-blot replicators (V & P Scientific; VP 409), resulting in a final primary screening concentration of 1×. Sterols were added to cells as an ethanol solution (0.2% final ethanol concentration). Positive control wells (ketoconazole, 2.5 µM) and DMSO vehicle controls were included in each assay plate. Cells were incubated under standard conditions (37° C., 5% $CO_2$) for 3 days and fixed with 4% paraformaldehyde (PFA) in phosphate buffered saline (PBS) for 20 min. Fixed plates were washed with PBS (200 µL per well) twice, permeabilized with 0.1% Triton X-100 and blocked with 10% donkey serum (v/v) in PBS for 40 min. Then, cells were labelled with MBP antibodies (Abcam, ab7349; 1:200) for 16 h at 4° C. followed by detection with Alexa Fluor conjugated secondary antibodies (1:500) for 45 min. Nuclei were visualized by DAPI staining (Sigma; 1 µg/ml). During washing steps, PBS was added using a multi-channel pipet and aspiration was performed using Biotek EL406 washer dispenser (Biotek) equipped with a 96-well aspiration manifold.

High-Content Imaging and Analysis

Plates were imaged on the Operetta High Content Imaging and Analysis system (PerkinElmer) and a set of 6 fields captured from each well resulting in an average of 1200 cells being scored per well. Analysis (PerkinElmer Harmony and Columbus software) began by identifying intact nuclei stained by DAPI; that is, those traced nuclei that were larger than 300 µm$^2$ in surface area. Each traced nucleus region was then expanded by 50% and cross-referenced with the mature myelin protein (MBP) stain to identify oligodendrocyte nuclei, and from this the percentage of oligodendrocytes was calculated. In some experiments, the total process length of MBP$^+$ oligodendrocytes was calculated as previously described.

High-Throughput Screening of 3,000 Bioactive Small Molecules

EpiSC-derived OPCs were grown and expanded in poly-ornithine and laminin-coated flasks before harvesting for plating. Cells were dispensed in differentiation media supplemented with Noggin (R&D Systems; 100 ng/ml), Neurotrophin 3 (R&D Systems; 10 ng/ml), cAMP (Sigma; 50 µM), and IGF-1 (R&D Systems; 100 ng/ml)) using a Biotek EL406 Microplate Washer Dispenser (Biotek) equipped with 5 µL dispense cassette (Biotek), into poly-D-lysine/laminin (Sigma, L2020; 4 µg/ml)-coated sterile, 384-well, CellCarrier ultra plates (PerkinElmer), to a final density of 12,500 cells per well and allowed to attach for 45 min before addition of drug. A 3 mM stock of bioactive compound library in dimethylsulphoxide (DMSO) were prepared in an Abgene storage 384-well plate (ThermoFisher Scientific; AB1055). These were added to assay plates using a 50 nL solid pin tool attached to Janus automated workstation (Perkin Elmer), resulting in a final screening concentration of 2 µM. Cells were incubated at 37° C. for 1 hour and then T3 (Sigma; 40 ng/ml) was added to all wells except negative controls, to which FGF (20 ng/ml) was added instead. Negative controls and T3-alone were included in each assay plate. After incubation at 37° C. for 72 h, cells were fixed, washed and stained similar to 96-well OPC assay protocol, although all the washing steps were performed using a Biotek EL406 Microplate Washer Dispenser (Biotek) equipped with a 96-well aspiration manifold. Cells were stained with DAPI (Sigma; 1 µg/ml) and MBP antibody (Abcam, ab7349; 1:100). Plates were imaged on the Operetta High Content Imaging and Analysis system (PerkinElmer) and a set of 4 fields captured from each well resulting in an average of 700 cells being scored per well. Analysis was performed as in High-Content Imaging and Analysis, above. All plates for the primary screen were processed and analyzed simultaneously to minimize variability. Molecules causing more than 20% reduction in nuclear count relative to DMSO control wells were removed from consideration, and hits were called on the basis of largest fold-increase in percentage of MBP$^+$ oligodendrocytes relative to DMSO controls within the same plate. When selecting the leading hits for further experiments, molecules obtained in previous screens were omitted, including imidazole antifungals and clemastine.

GC/MS-Based Sterol Profiling

EpiSC-derived OPCs were plated at one million cells per well in PDL- and laminin-coated six well plates with differentiation media. After 24 hours, cells were dissociated with Accutase, rinsed with saline, and cell pellets were frozen. For sterol analyses, cells were lysed in methanol (Sigma-Aldrich) with agitation for 30 minutes and cell debris removed by centrifugation at 10,000 rpm for 15 min. Cholesterol-d7 standard (25,26,26,26,27,27,27-$^2$H$_7$-cholesterol, Cambridge Isotope Laboratories) was added before drying under nitrogen stream and derivatization with 55 µl of bis(trimethylsilyl)trifluoroacetamide/trimethylchlorosilane to form trimethylsilyl derivatives. Following derivatization at 60° C. for 20 minutes, 1 µl was analyzed by gas chromatography/mass spectrometry using an Agilent 5973 Network Mass Selective Detector equipped with a 6890 gas chromatograph system and a HP-5MS capillary column (60 m×0.25 µm×0.25 mm). Samples were injected in splitless mode and analyzed using electron impact ionization. Ion fragment peaks were integrated to calculate sterol abundance, and quantitation was relative to cholesterol-d7. The following m/z ion fragments were used to quantitate each metabolite: cholesterol-d7 (465), FF-Mas (482), cholesterol (368), zymostenol (458), zymosterol (456), desmosterol (456, 343), 7-dehydrocholesterol (456, 325), lanosterol (393), lathosterol (458), 14-dehydrozymostenol (456). Calibration curves were generated by injecting varying concentrations of sterol standards and maintaining a fixed amount of cholesterol-D7. The human glioma cell line GBM528 was a gift of Jeremy Rich (Cleveland Clinic). Cortical organoids were generated as described previously.

CYP51 Enzymatic Assay

CYP51 enzymatic activity was measured using a reported method with slight modifications: rat CYP51 (Cypex, Inc.) was used as enzyme; reaction volume was 500 µl; reaction time was 30 minutes; lanosterol concentration was 50 µM; and reactions were quenched with 500 µl isopropanol. Finally, 15 µl of each reaction/isopropanol mixture was injected onto a SCIEX Triple Quad 6500 LC-MS/MS system using an APCI ion source in positive ion mode with a Shimadzu UFLC-20AD HPLC and a Phenomenex Kinetix C18XB 50×2.1×2.6 column at 40° C.

EBP Enzymatic Assay

EBP enzymatic activity was measured using a reported method with slight modifications: active EBP was obtained from mouse microsomes, inhibitors were added, zymostenol was added at a final concentration of 25 µM in a final reaction volume of 500 μl, and the reaction incubated at 37° C. for 2 h. Sterols were extracted using 3×1 ml hexanes, cholesterol-d7 was added to enable quantitation, and the pooled organics were dried ($Na_2SO_4$) and evaporated under nitrogen gas. Samples were then silylated and analyzed using GC/MS as described above.

siRNA Treatments

Cell-permeable siRNAs were obtained as pools of 4 individual siRNAs targeting mouse CYP51, or a non-targeting control (Accell siRNAs, Dharmacon). For differentiation analysis, cells were plated in 96-well plate (as detailed above) and treated with 1 μM pooled siRNA suspended in RNAse free water diluted in differentiation media (as detailed above). For sterol analysis cells were plated in a six-well plate at 300,000 cells per well in standard differentiation media supplemented with PDGF (R&D Systems, 20 ng/ml), neurotrophin 3 (R&D Systems; 10 ng/ml), cAMP (Sigma; 50 μM), IGF-1 (R&D Systems; 100 ng/ml), noggin (R&D Systems; 100 ng/ml). At 24 hours, 1 μM siRNA was added to the media. Cells were grown for three more days in siRNA containing media, with growth factor supplementation every 48 h, before harvesting and processing for GC/MS analysis as detailed above.

Focal Demyelination, Drug Treatment and Histological Analysis

Focal demyelination in the dorsal column of the spinal cord was induced by the injection of 1% LPC solution. 12 week old C57BL/6 female mice were anesthetized using isoflurane and T10 laminectomies were performed. 1 μl of 1% LPC was infused into the dorsal column at a rate of 15 μl/hour. At day 4, animals were randomized into treatment groups prior to treatment (2 animals were excluded due to surgical complications). Between days 4 and 11 post laminectomy, animals received daily injections of either vehicle or drug intraperitoneally. Drugs were dissolved in DMSO or corn oil and then diluted with sterile saline for injections such that final doses were 2 mg/kg for Tamoxifen and 10 mg/kg for Ifenprodil. This experiment was done in a blinded manner: compounds were coded to ensure the researchers performing the experiments were unaware of the treatment being administered to each animal. All animals were euthanized 12 days post laminectomy (n=4-6 per group). Mice were anesthetized using ketamine/xylazine rodent cocktail and then euthanized by transcardial perfusion with 4% PFA, 2% glutaraldehyde, and 0.1 M sodium cacodylate. Samples were osmicated, stained en bloc with uranyl acetate and embedded in EMbed 812, an Epon-812 substitute (EMS). 1 μm sections were cut and stained with toluidine blue and visualized on a light microscope (Leica DM5500B). The number of myelinated axons per unit areas was counted from sections in the middle of each lesion and then averaged over each treatment group. A Mann-Whitney statistical analysis was performed to assess statistical significance.

Analysis of Mouse Brain Sterol Levels

Ten to twelve week old male C57BL/6 mice were injected with 2 mg/kg tamoxifen, 10 mg/kg ifenprodil, or 10 mg/kg miconazole dissolved in corn oil (tamoxifen) or DMSO (ifenprodil, miconazole) in sterile saline daily for three days. Mice were anaesthetized with isoflurane and perfused with phosphate buffered saline to remove blood from the brain. Brains were collected and flash frozen using liquid nitrogen. The samples were pulverized and 50-100 milligrams of tissue were collected for further processing. A modified Folch protocol was used for extraction of sterols. Briefly, samples were resuspended in a 2:1 chloroform/methanol mixture and homogenized. Cell debris was removed by centrifugation at 4000 g for 10 min. The solution was dried under air and resuspended in hexane with a cholesterol-D7 standard and dried again. Lipids were derivatized with 70 μl of bis(trimethylsilyl)trifluoroacetamide; 2 μls were injected and analyzed by GC/MS as described above.

Estrogen-Dependent Cell Proliferation Assay

Estrogen-dependent cell proliferation was measured as previously described with minor modifications. After growth in estrogen-free media (Phenol red-free RPMI supplemented with 10% charcoal stripped fetal bovine serum) for 5 days, cells were seeded at 2,500 cells/well into 96 well plates. The following day 3× drug containing media was added to triplicate wells and cells were allowed to grow for an additional 5 days at 37° C. in standard a 5% $CO_2$ humidified incubator. Total DNA per well was measured using an adaptation of the method of Labarca and Paigen. At this time media was removed, cells were washed one time with 0.25×PBS and 100 ul of distilled water was added. Plates were frozen and thawed to enhance cell lysis and 200 μl of 10 μg/ml Hoechst 33258 (Sigma-Aldrich, St. Louis, MO.) in 2M NaCl, 1 mM EDTA, 10 mM Tris-HCl pH 7.4 was added. After incubation at room temperature for 2 hours, plates were read in a SpectraMax i3 fluorescent plate reader (Molecular Devices, Sunnyvale, CA) with excitation at 360 nm and emission at 460 nm. All values were converted to microgram DNA per well using a standard curve derived from purified salmon testes DNA.

Oligodendrocyte Formation and Imaging on Eletrospun Microfibers

A 12-well plate containing Mimetex aligned scaffold (microfiber plate, AMSBIO, AMS.TECL-006-1X, Electrospun poly-L-lactide Scaffold, 2 μM fibre diameter cell crown inserts) was prepared as previously described. Briefly, inserts were sterilized with 70% ethanol and washed with PBS before being coated with polyornithine and laminin. After laminin coating, 100,000 cells/mL of EpiSC-derived OPCs were plated in differentiation medium. After 24 h the media was replaced with fresh media containing small molecule treatments. Every 48 h the media was replaced with fresh compound containing media for a total of 14 days. Plates were fixed with 4% PFA, permeabilized with 0.1% Triton X-100, and blocked with 10% donkey serum (v/v) in PBS for 60 min. Plates were stained for MBP (Abcam, ab7349; 1:100) and DAPI staining (Sigma; 5 μg/ml). After staining, the inserts were moved into new 12-well plate and covered with 2 mL of PBS before imaging in Operetta high content Imaging and analysis system. Plates were imaged on the Operetta High Content Imaging and Analysis system (PerkinElmer) and a set of 8 fields captured from each well resulting in an average of 45,000 cells being scored per well. Analysis (PerkinElmer Harmony and Columbus software) identified intact nuclei stained by DAPI and calculated the MBP signal intensity per cell per well. Microfiber insert tracking images were taken using a Leica DMi8 with a 20× Dry/NA 0.40 objective. Microfiber plate inserts were mounted using Flouromount-G (SouthernBiotech) and allowed to partially harden before coverslips were added and the insert ring was removed. Confocal images were obtained on a Leica SP8 confocal scanning microscope, with 40× oil/NA 1.30 objective. Confocal stacks of 0.336 μm z-steps were taken at 1024×1024. Each fluorophore was excited sequentially and all contrast and brightness changes were applied consistently between images.

CYP51 qPCR

Cells were plated at 500,000 cells per well in a six-well plate and were grown in standard differentiation media supplemented with PDGF, neurotrophin 3, cAMP, IGF-1, and noggin for four days as described above. At 24 hours, cells were treated with 1 µM siRNA. Growth factors were added every 48 hours. After three days of siRNA treatment, RNA was isolated with the RNeasy Mini Kit (Qiagen), and cDNA was made using High-Capacity RNA-to-cDNA™ Kit (Applied Biosystems). Exon spanning primers for ActinB (Thermo-Fisher, Taqman, Mm02619580_g1) and CYP51 (Thermo-Fisher, Taqman, Mm00490968_m1) were used for detection of relative RNA levels by quantitative real time PCR (Applied Biosystems, 7300 Realtime PCR system). Cycle time and outliers were calculated using Applied Biosystems' 7300 System Sequence Detection Software version 1.4.

Muscarinic Receptor Antagonism Assay

GeneBLAzer M1-NFAT-bla CHO-K1 cells (or M3- or M5-NFAT-bla CHO-K1 cells)(ThermoFisher) were thawed into Assay Media (DMEM, 10% dialyzed FBS, 25 mM HEPES pH 7.3, 0.1 mM NEAA). 10,000 cells/well were added to a 384-well TC treated assay plate and incubated 16-24 h at 37° C. 4 µl of a 10× stock of antimuscarinic molecules was added to the plate and incubated 30 min. 4 µl of 10× control agonist Carbachol at the pre-determined EC80 concentration was added to wells containing antimuscarinic molecules. The plate was incubated 5 h and 8 µl of 1 µM Substrate+Solution D Loading Solution was added to each well and the plate was incubated 2 h at room temperature before reading on a fluorescence plate reader.

Results

High-throughput phenotypic screening has emerged as a promising route to identifying small molecules that enhance the generation of new oligodendrocytes from OPCs. Multiple groups have identified screening hits that show functional benefit in animal models of demyelination. However, translation of these findings to humans has been impeded by lack of knowledge of the functional targets of these molecules in enhancing oligodendrocyte formation. Previously the inventors used mouse pluripotent stem cell-derived OPCs to identify structurally-diverse imidazole antifungal drugs as a robust class of hits that stimulate the generation of new mouse and human oligodendrocytes and enhance remyelination in mouse disease models. Imidazole antifungals are known to mediate their effects in yeast by inhibiting sterol 14-α-demethylase (CYP51), an essential enzyme for sterol biosynthesis in both fungal and mammalian cells. However, the mechanism of action of imidazole antifungal drugs in OPCs has remained undefined.

Figure 1B:
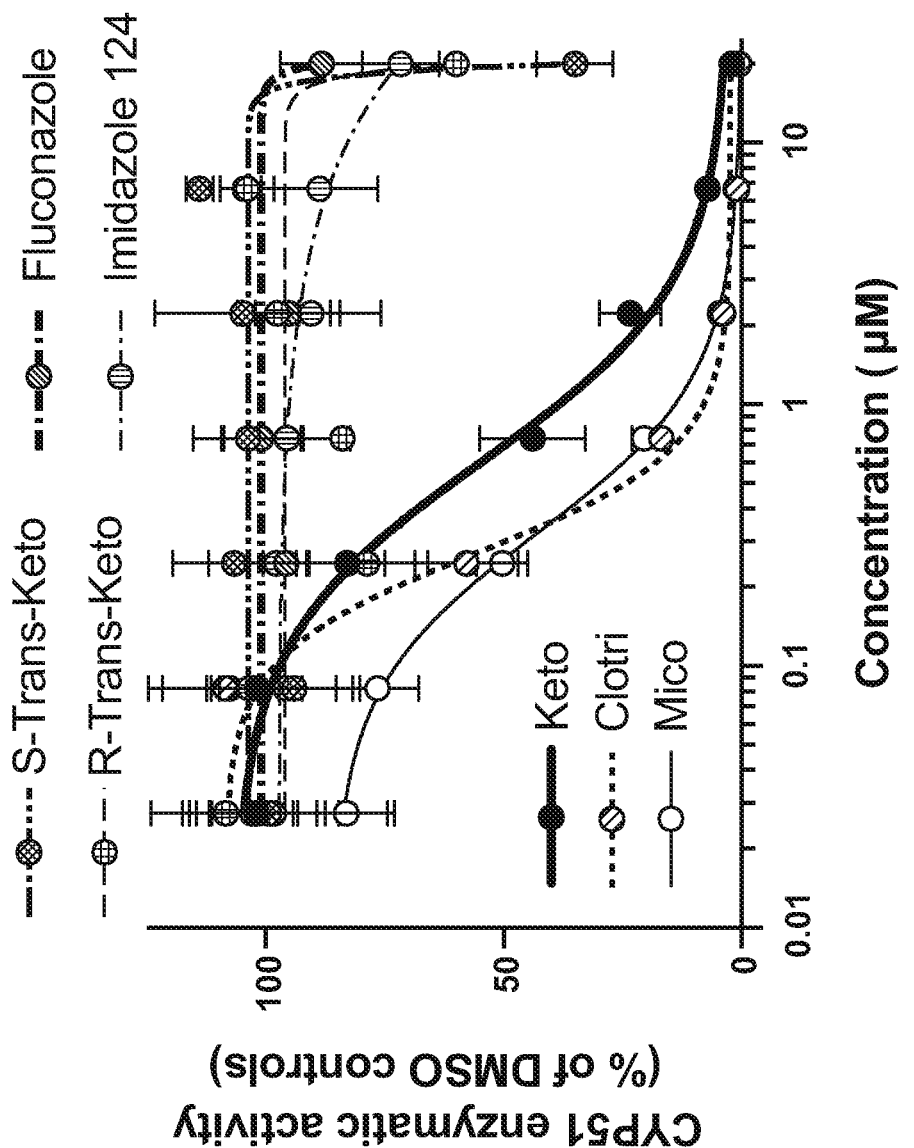
Figure 1C:
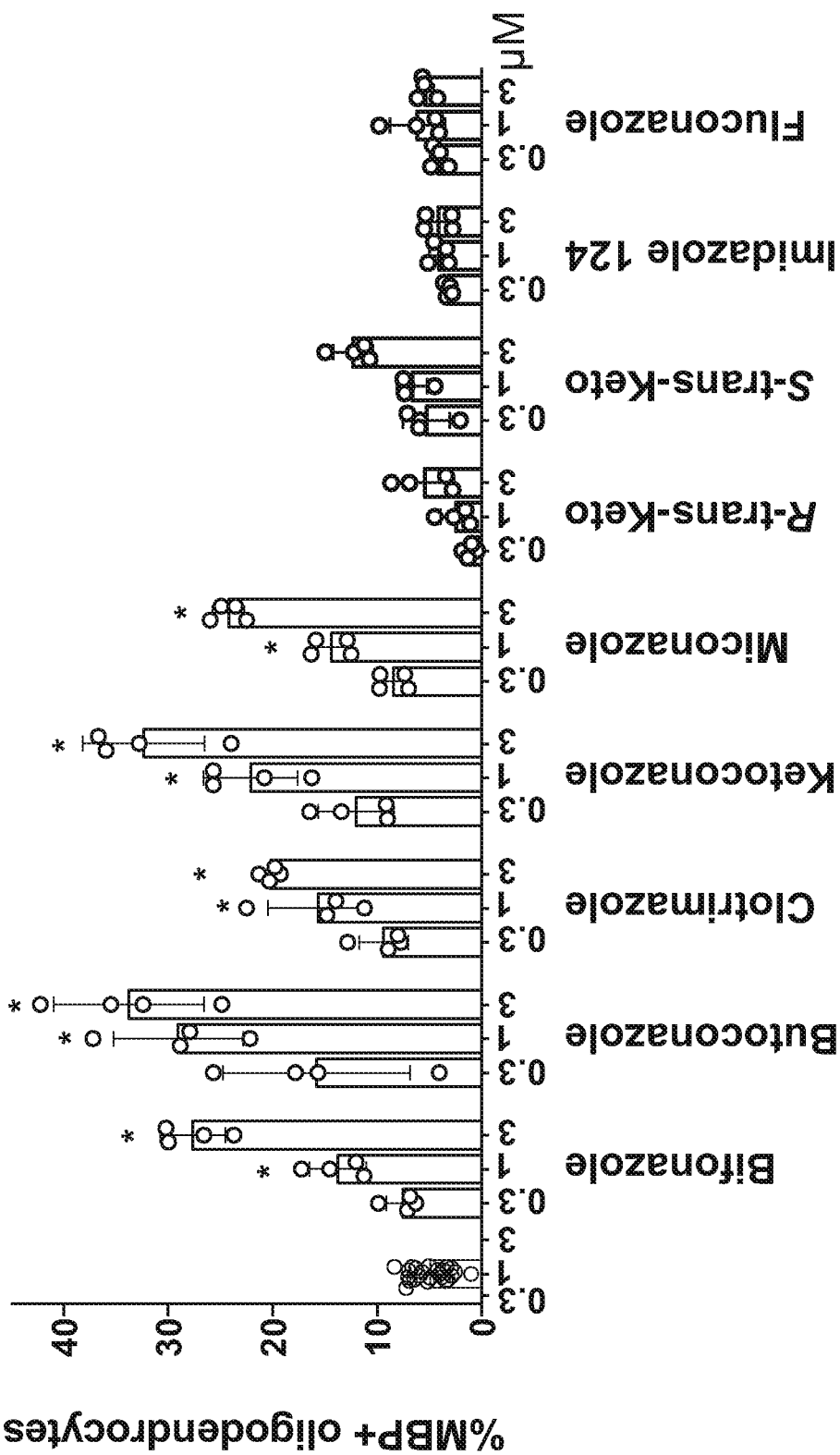
Figure 1D:
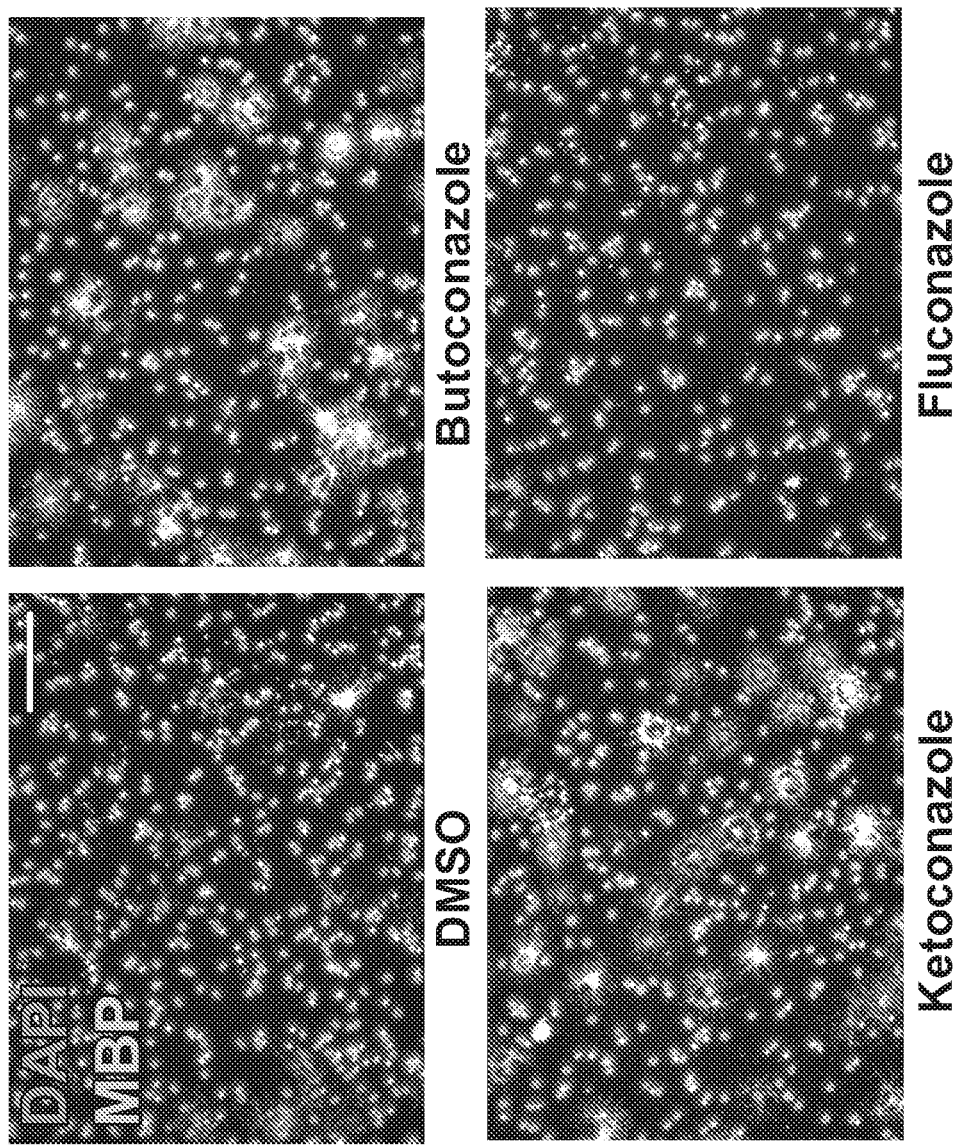
Figure 1E:
Figure 1E:
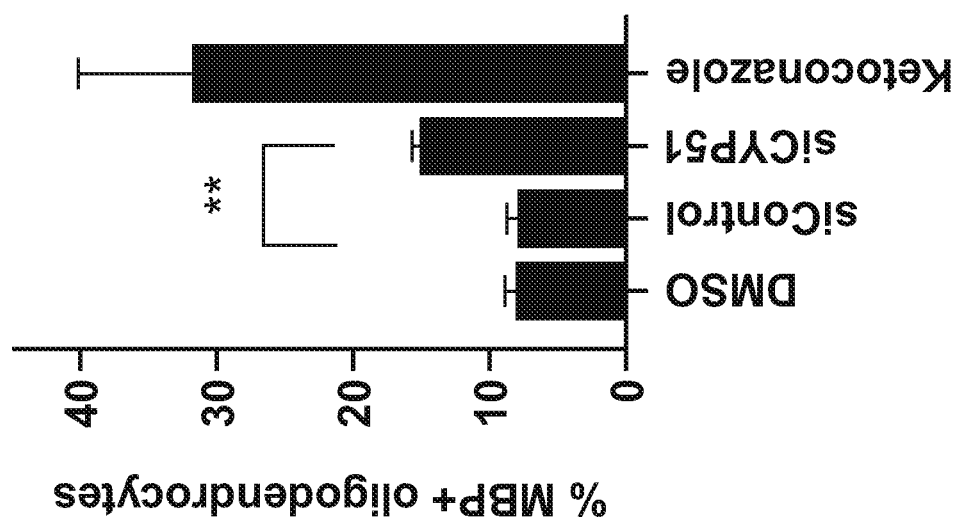

To test whether CYP51 inhibition is responsible for the effect of imidazole antifungal drugs in promoting the generation of oligodendrocytes from OPCs, the inventors assembled a collection of nine azole-containing molecules with wide-ranging potency for mammalian CYP51 inhibition (FIG. 1A). The inventors used a mass spectrometry-based biochemical assay to confirm that FDA-approved imidazole antifungals (miconazole, clotrimazole, and ketoconazole) showed clear inhibition of rodent CYP51 in vitro with similar $IC_{50}$ values ranging from 300-700 nM (FIG. 1B). Three close analogs of ketoconazole known to lack antifungal activity were strikingly less effective at inhibiting mammalian CYP51: namely, the R-trans and S-trans diastereomers of ketoconazole[11] and a truncated analog, Imidazole 124 (FIG. 1A,B). Additionally, the inventors confirmed that the triazole antifungal fluconazole, which selectively targets yeast CYP51, did not inhibit mammalian CYP51 in vitro (FIG. 1B). For each molecule in the panel, potency for inhibition of mammalian CYP51 in vitro paralleled the enhanced formation of mature myelin basic protein-positive (MBP+) oligodendrocytes from mouse epiblast stem cell-derived OPCs cultured under differentiation-permissive conditions (FIG. 1C,D). These findings suggest that imidazole antifungals act by their canonical target, CYP51, to enhance oligodendrocyte formation.

Since CYP51 is known to function in cholesterol biosynthesis in mammalian cells, the inventors assessed functional inhibition of CYP51 in OPCs using gas chromatography/mass spectrometry (GC/MS) to measure cellular sterol levels (for a diagram of cholesterol pathway enzymes and intermediates). Mouse OPCs were treated with each azole-containing molecule for 24 hours, at which point they were lysed for analysis by GC/MS and levels of lanosterol, the substrate of CYP51, as well as downstream cholesterol levels were quantified. Lanosterol accumulated in OPCs only after treatment with each of five active imidazole antifungals, mirroring the effects of these molecules on CYP51 function in our biochemical assay (FIG. 1B,E). Notably, to eliminate potential cell source or assay artifacts, the inventors confirmed all effects of small molecules on oligodendrocyte formation and sterol levels using a second, independently isolated batch of mouse epiblast stem cell-derived OPCs. Additionally, the effects of azole molecules on oligodendrocyte formation and lanosterol levels were confirmed using primary mouse OPCs, using an orthogonal image quantitation approach measuring total process length, and using proteolipid protein 1 (PLP1) as a second marker of oligodendrocyte formation. For ketoconazole, the dose-response for accumulation of lanosterol closely resembled the dose-response for enhanced oligodendrocyte formation (compare FIG. 1F, 1C). The tight correlation between CYP51 inhibition and enhanced formation of oligodendrocytes among these highly structurally diverse azole-containing small molecules suggests that CYP51 is the relevant target in OPCs.

Figure 1H:
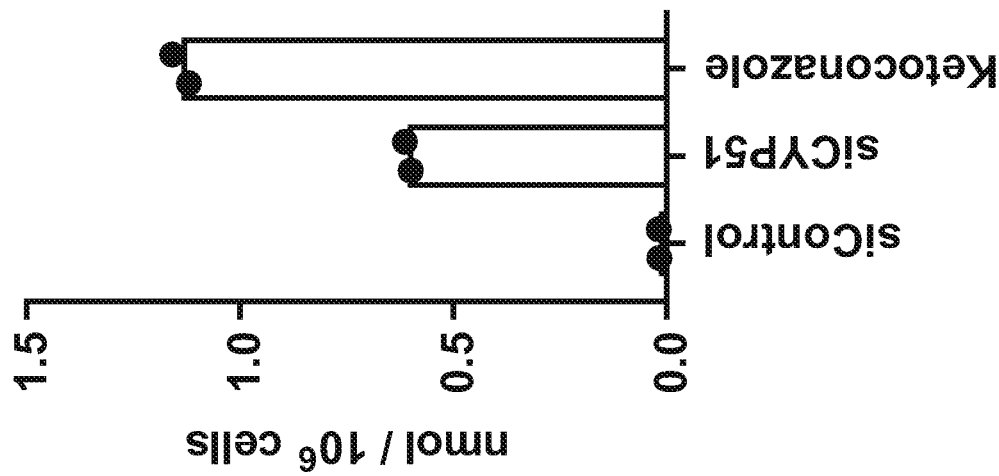
Figure 1G:
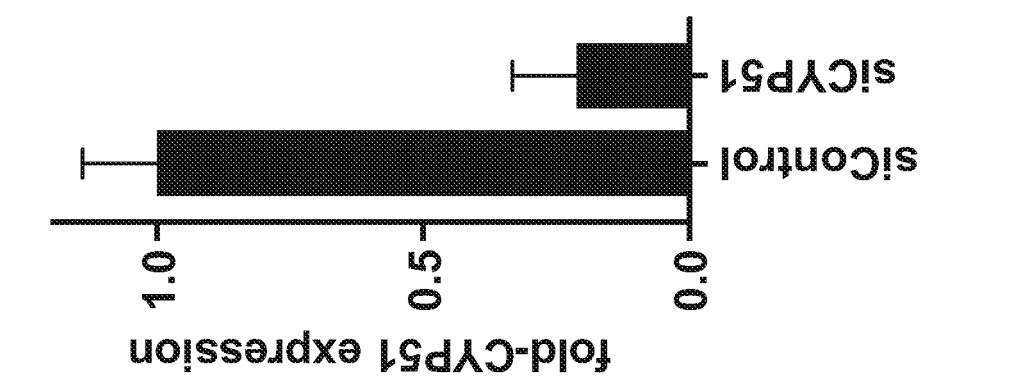
Figure 1F:
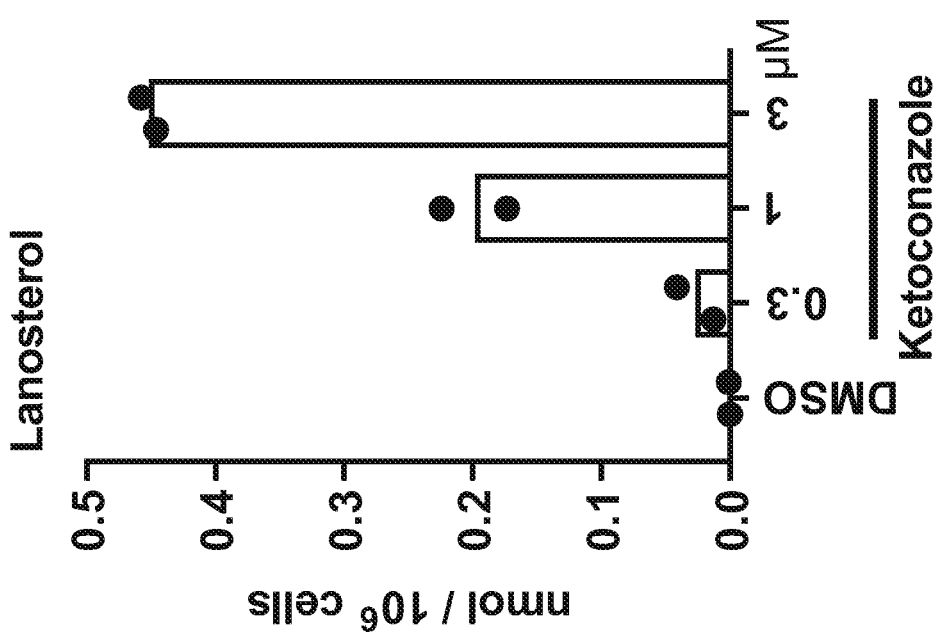

The inventors next used RNA interference and metabolite supplementation to independently confirm the role of CYP51 in oligodendrocyte formation. The inventors used cell-permeable siRNA reagents to deplete CYP51 transcript levels in OPCs by 80% (FIG. 1G). Suppression of CYP51 led to significant accumulation of lanosterol and enhanced formation of MBP+ oligodendrocytes, although this effect was smaller than seen for ketoconazole treatment, likely due to the siRNA treatment's slower kinetics and incomplete target suppression (FIG. 1H,I). Additionally, the inventors treated OPCs directly with purified lanosterol and observed enhanced formation of MBP+ oligodendrocytes in a dose-responsive fashion (FIG. 1J). This finding suggests that accumulation of sterol intermediates may play a direct role in enhancing oligodendrocyte formation from OPCs.

Figure 2E:
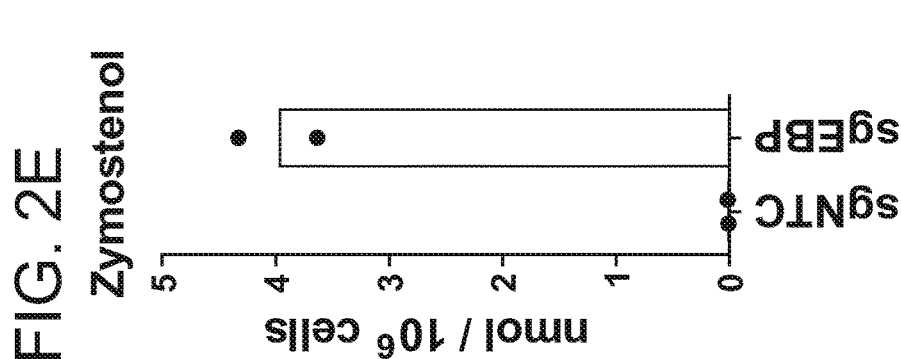
FIGS. 2(*a-h*) illustrate structures, plots, graphs, and images showing the effect of small-molecule inhibition of enzymes in the cholesterol biosynthesis pathway on enhancing oligodendrocyte formation. a) Abbreviated cholesterol biosynthesis pathway, with intermediate metabolites and selective inhibitors labeled. Green, enzyme targets and small molecules whose inhibition promotes oligodendrocyte formation. For a more detailed pathway map and chemical structures of metabolites and inhibitors. b) Percentage of MBP$^+$ oligodendrocytes generated from OPCs at 72 h following treatment with the indicated pathway inhibitors. n=4 replicates per condition, with >1,000 cells analyzed per replicate. *, P<0.02, t-test. c) GC/MS-based quantitation of 14-dehydrozymostenol and zymostenol levels in OPCs treated 24 h with the indicated doses of amorolfine or TASIN-1. n=2 replicates per condition. d) Percentage of MBP$^+$ oligodendrocytes generated from OPCs infected with lentivirus expressing Cas9 and guide RNA targeting EBP. Infected cells were selected with puromycin for 96 hours and assayed for MBP+ cells after an additional 72 h in differentiation media. 8 replicates per condition, with >1,000 cells analyzed per replicate. Two-tailed t-test, **P<0.01. e) Functional validation of CRISPR-based targeting of EBP using GC/MS-based quantitation of zymostenol levels. OPCs were infected with lentivirus expressing the indicated guides and infected cells were selected by exposure to puromycin-containing media for 96 h prior to harvest of sterols. n=2 replicates per condition. f) Representative images of the oligodendrocyte formation assay shown in e. Nuclei are labeled with DAPI (blue), and oligodendrocytes are indicated by immunostaining for myelin basic protein (green). Scale bar, 100 μm. g) Percentage of MBP$^+$ oligodendrocytes generated from OPCs at 72 h following treatment with the indicated purified sterol intermediates. n=4 replicates per condition, with >1,000 cells analyzed per replicate. Green labels highlight metabolites that accumulate after treatment with inhibitors that enhance oligodendrocyte formation in panel b. h) Percentage of MBP$^+$ oligodendrocytes generated from OPCs at 72 h following treatment with the indicated purified 'meiosis-activating sterols'. n=4 replicates per condition, with >1,000 cells analyzed per replicate. All bar graphs indicate mean+/−standard deviation, and findings in b-d are representative of two or more independent experiments. Experiments were performed in the OPC-5 derivation and panels b-c and g-h have been confirmed in a second independent derivation of OPCs (OPC-1). CRISPR targeting of EBP has been confirmed using a second targeting sequence.
Figure 2D:
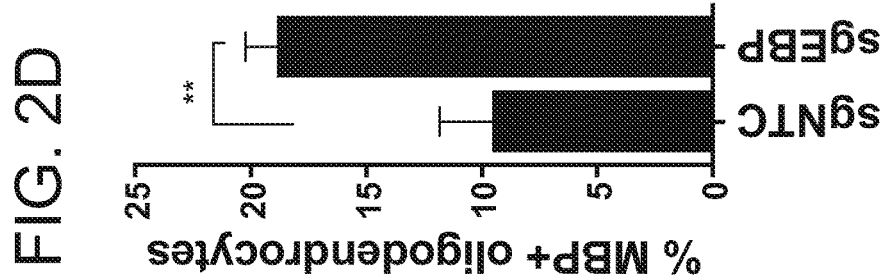
Figure 2C:
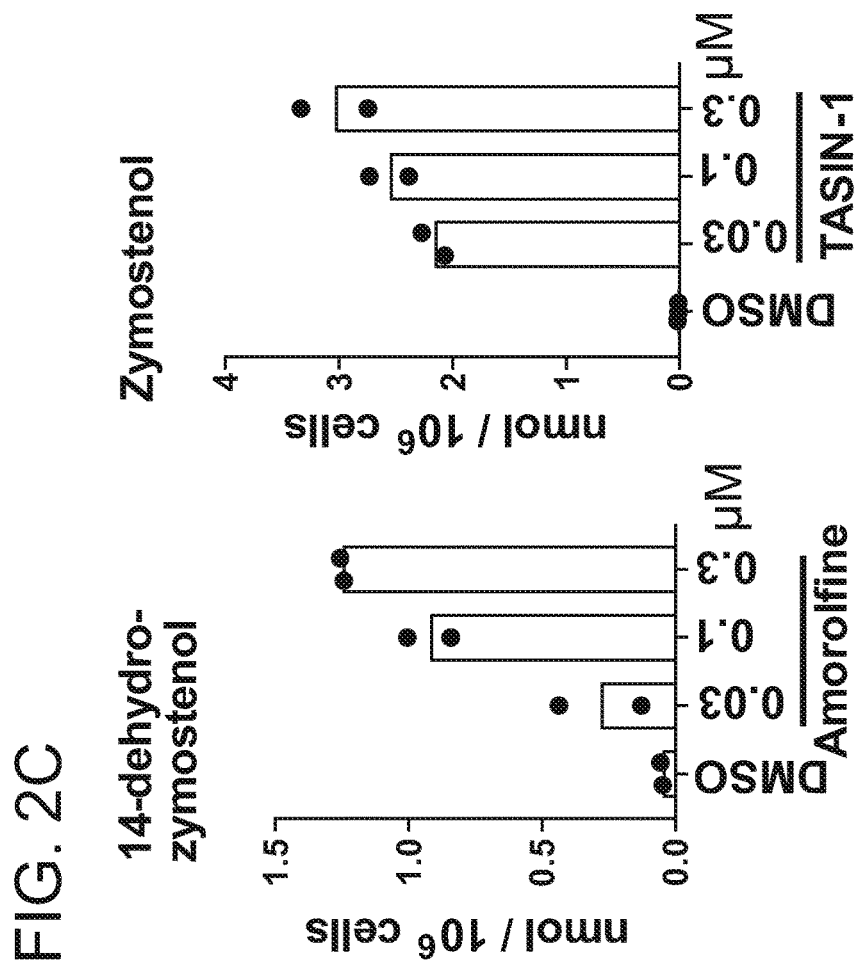

Since CYP51 inhibition was sufficient to induce the formation of oligodendrocytes, the inventors used a chemical genetics approach to test whether modulation of other steps in cholesterol biosynthesis has a similar effect. Cholesterol biosynthesis is a long, intricately regulated pathway for which many high-quality small-molecule probes and approved drugs are available (FIG. 2A). The inventors collected selective small-molecule inhibitors of eight enzymes throughout the cholesterol biosynthesis pathway and assessed their impact on oligodendrocyte generation and sterol levels in OPCs. The inventors confirmed that inhibitors targeting sterol-metabolizing enzymes selectively caused the accumulation of the expected upstream sterol intermediates in OPCs, and for all probes the inventors confirmed reduced levels of one or both of the pathway's terminal products, desmosterol and cholesterol. The inventors evaluated the effects of each of these eight pathway inhibitors on OPC differentiation to oligodendrocytes. Only molecules targeting CYP51 (ketoconazole), sterol 14-reductase (amorolfine), and EBP (TASIN-1) enhanced formation of MBP+ oligodendrocytes, whereas inhibitors of the five other pathway enzymes were ineffective (FIG. 2B). Treatments had minimal effect on total cell number during the 3 d assay. Amorolfine and TASIN-1 were effective at doses below 100 nM, with potency for accumulation of 14-dehydrozymostenol and zymostenol mirroring potency for enhancement of oligodendrocyte formation (FIG. 2C). Distinct structural classes of inhibitors of CYP51, sterol 14 reductase, and EBP also enhanced oligodendrocyte formation, with one EBP inhibitor, TASIN-449 functional at picomolar doses, providing independent chemical validation for each of these enzyme targets.

Figure 2F:
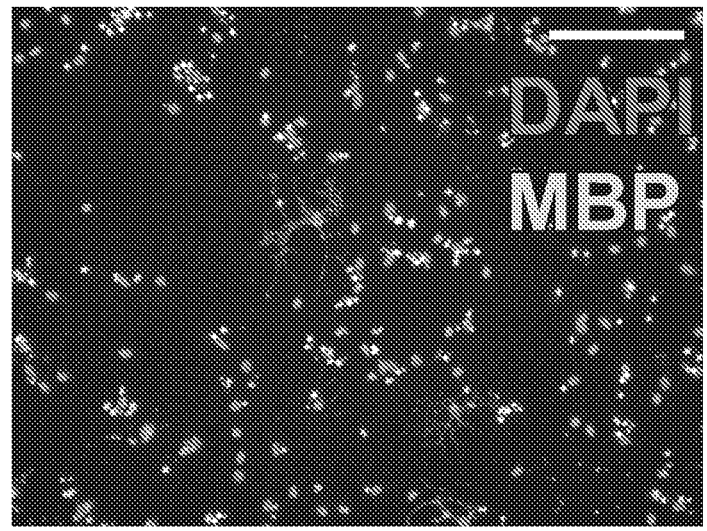
Figure 2F:
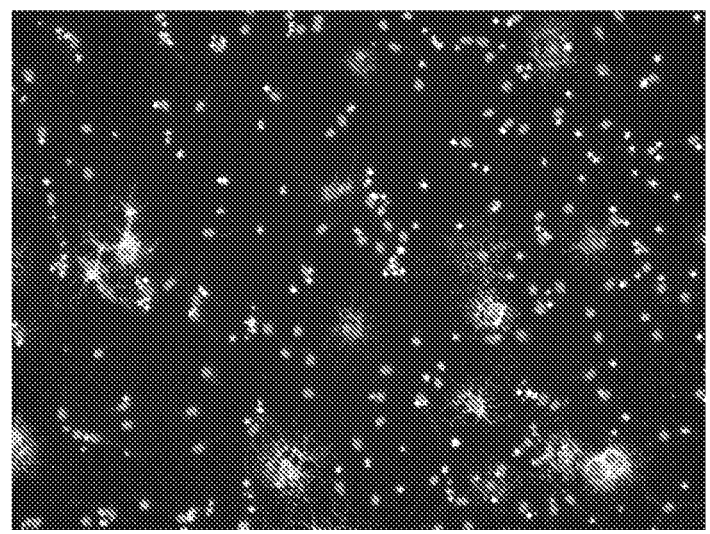
Figure 2H:
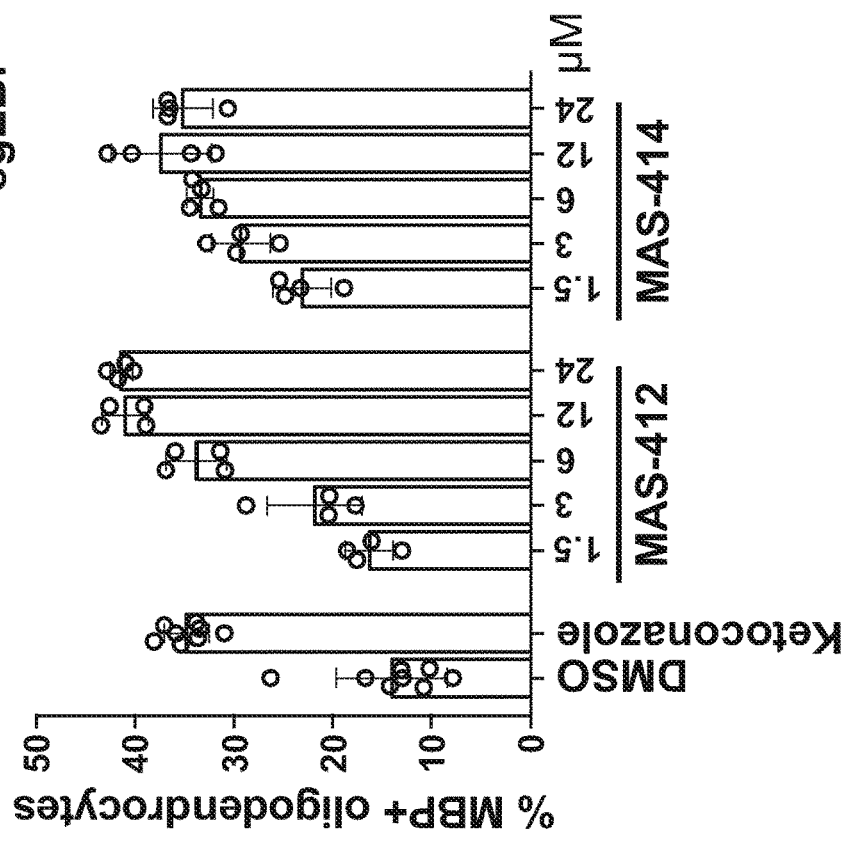

Additionally, the inventors used CRISPR/Cas9 targeting to evaluate the effects of genetic suppression of EBP. OPCs were treated with lentivirus expressing Cas9 and guide RNA targeting EBP, and infected cells were selected on the basis of puromycin resistance. These OPCs demonstrated reduced EBP transcript levels, robust accumulation of the expected intermediate zymostenol, and also enhanced formation of oligodendrocytes under differentiation-permissive conditions (FIG. 2D-F). Two independent guide RNA sequences provided comparable results. In total, this genetic and chemical genetic analysis suggests that inhibition of the cholesterol biosynthesis pathway within a limited window spanning CYP51 to EBP is sufficient for enhancing the formation of oligodendrocytes.

Figure 2G:
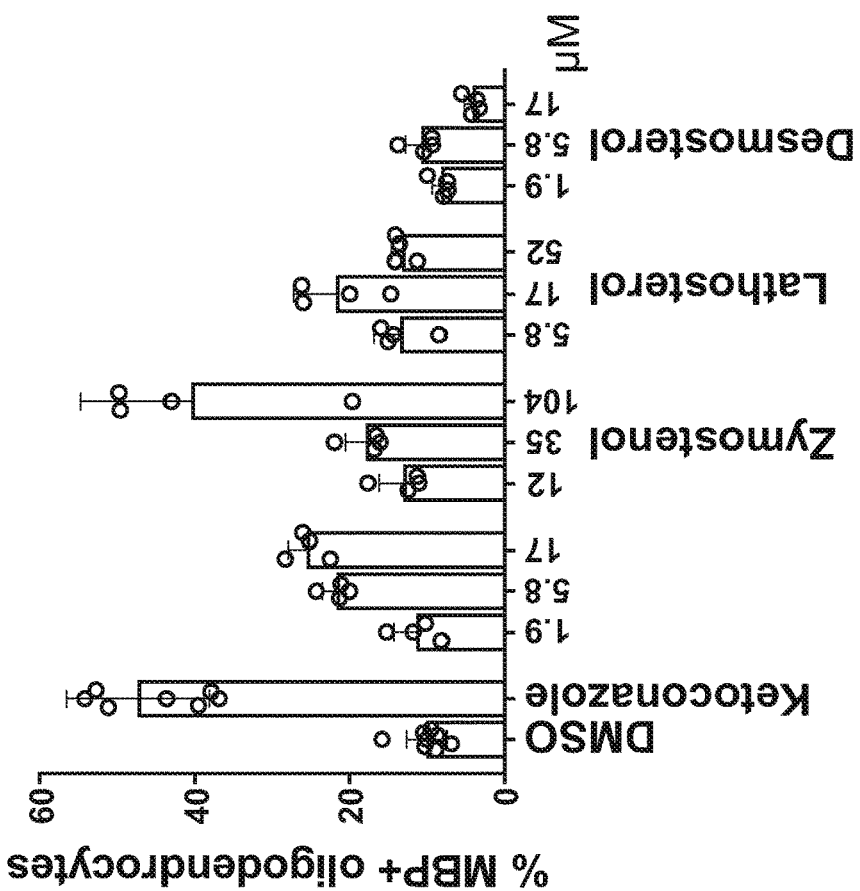
Figure 5D:
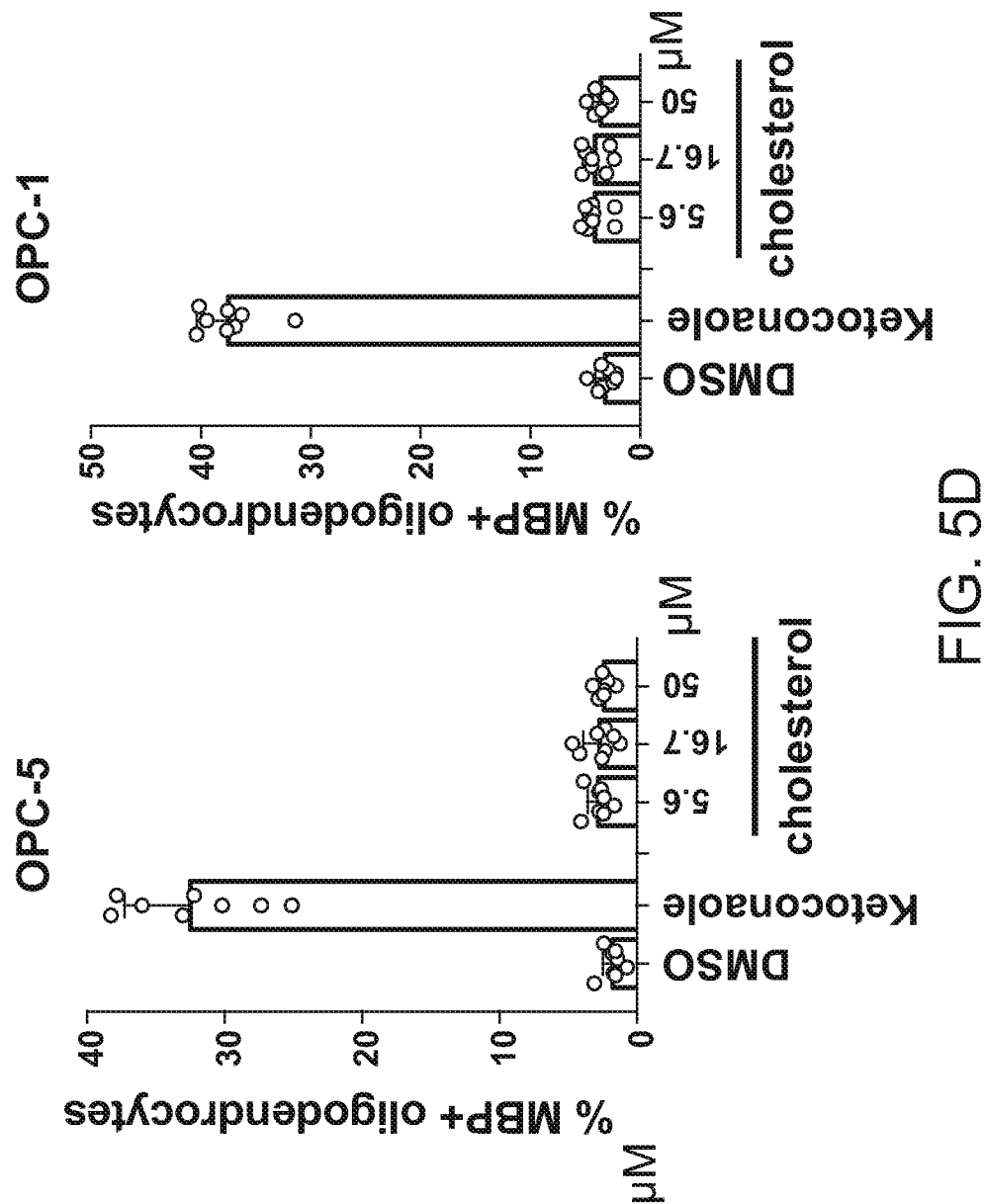
FIGS. 5(A-P) illustrate structures, plots, graphs, and images showing the effect of 8,9-unsaturated sterols on oligodendrocyte formation. a) Percentage of MBP$^+$ oligodendrocytes generated from OPCs (OPC-5) at 72 h following treatment with methyl β-cyclodextrin (1 mM) for 30 min at 37° C. n=4 replicates per condition, with >1,000 cells analyzed per replicate. b) GC/MS-based quantitation of cholesterol (left) and desmosterol (right) levels in OPCs (OPC-5) treated with methyl β-cyclodextrin (Me-j-CD) at 1 mM or ketoconazole at 2.5 μM. n=2 replicates per condition. Cells were harvested 24 h after plating, but methyl β-cyclodextrin was removed from the culture media after 30 min. c) Percentage of MBP$^+$ oligodendrocytes generated from OPC-1 OPCs at 72 h following treatment with the indicated purified sterol intermediates. n=4 replicates per condition, with >1,000 cells analyzed per replicate. Green labels indicate metabolites that accumulate after treatments that enhance oligodendrocyte formation. d) Percentage of MBP$^+$ oligodendrocytes generated from OPC-5 and OPC-1 OPCs at 72 h following treatment with the indicated concentrations of cholesterol. n=4 replicates per condition, with >1,000 cells analyzed per replicate. e) Percentage of MBP$^+$ oligodendrocytes generated from OPCs (OPC-5) at 72 h following treatment with the indicated small molecules or combinations of small molecules (ketoconazole, 2.5 μM; Ro 48-8071, 11 nM; liothyronine, 3 μM). n=4 replicates per condition, with >1,000 cells analyzed per replicate. f) GC/MS-based quantitation of lanosterol levels in OPCs (OPC-5) treated 24 h with the indicated small molecules or combinations of small molecules at concentrations stated in e. n=2 replicates per condition. g) Total cell number as measured by counting of DAPI+ nuclei in the experiment presented in panel e. h, i) Percentage of MBP$^+$ oligodendrocytes generated from OPC-5 (top) and OPC-1 (bottom) at 72 h following treatment with the indicated concentrations of sterols that are structurally identical aside from the presence or absence of the D8,9 double bond. Structures shown at bottom. n=4 replicates per condition, with >1,000 cells analyzed per replicate. j) Percentage of MBP$^+$ oligodendrocytes generated from OPC-5 (top) and OPC-1 at 72 h following treatment with 2,2-dimethylzymosterol. n=4 replicates per condition, with >1,000 cells analyzed per replicate. j) Percentage of MBP$^+$ oligodendrocytes generated from OPC-5 (top) and OPC-1 (bottom) at 72 h following treatment with 2,2-Dimethylzymosterol. n=4 replicates per condition, with >1,000 cells analyzed per replicate. k) Representative images of OPC-5 cells treated 72 h with vehicle and 2,2-Dimethylzymosterol (5 μM). Nuclei are labeled with DAPI (blue), and oligodendrocytes are indicated by immunostaining for myelin basic protein (green). Scale bar, 100 μm. 1) Percentage of MBP$^+$ oligodendrocytes generated from OPCs (OPC-5) at 72 h following treatment with the indicated small molecules or combinations of small molecules (ketoconazole, 2.5 μM; 2,2-Dimethylzymosterol, 1.5 μM; liothyronine, 3 μM). n=4 replicates per condition, with >1,000 cells analyzed per replicate. m) Percentage of MBP$^+$ oligodendrocytes generated from OPC-1 at 72 h following treatment with MAS-412 and MAS-414. n=4 replicates per condition, with >1,000 cells analyzed per replicate. n) Representative images of OPC-5 cells treated 72 h with vehicle, MAS-412, or MAS-414 (3 μM). Nuclei are labeled with DAPI (blue), and oligodendrocytes are indicated by immunostaining for myelin basic protein (green). Scale bar, 100 μm. o) Percentage of MBP$^+$ oligodendrocytes generated from OPC-5 (left) and OPC-1 (right) at 72 h following treatment with FF-MAS and T-MAS. n=4 replicates per condition, with >1,000 cells analyzed per replicate. p) Chemical structures of FF-MAS, T-MAS, MAS-412, and MAS-414 with annotations of the cholesterol biosynthesis pathway enzymes that metabolize these sterols.
Figure 5G:
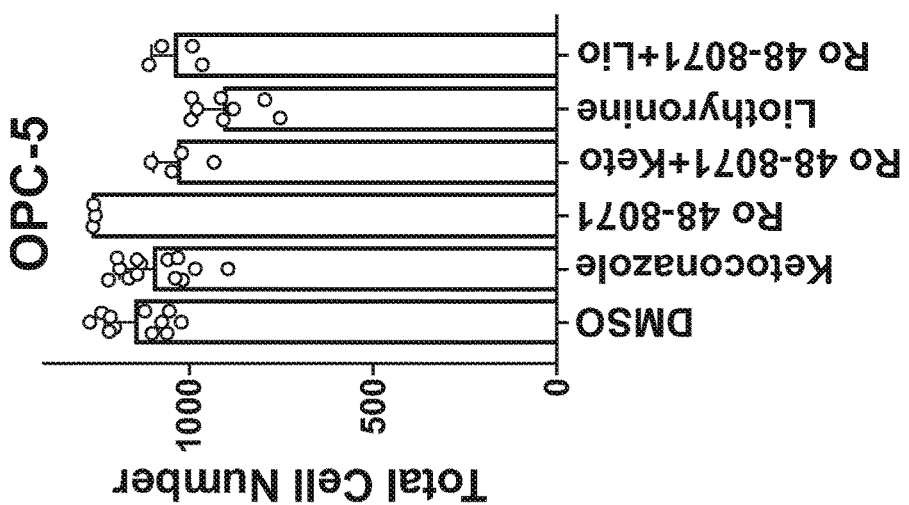
Figure 5F:
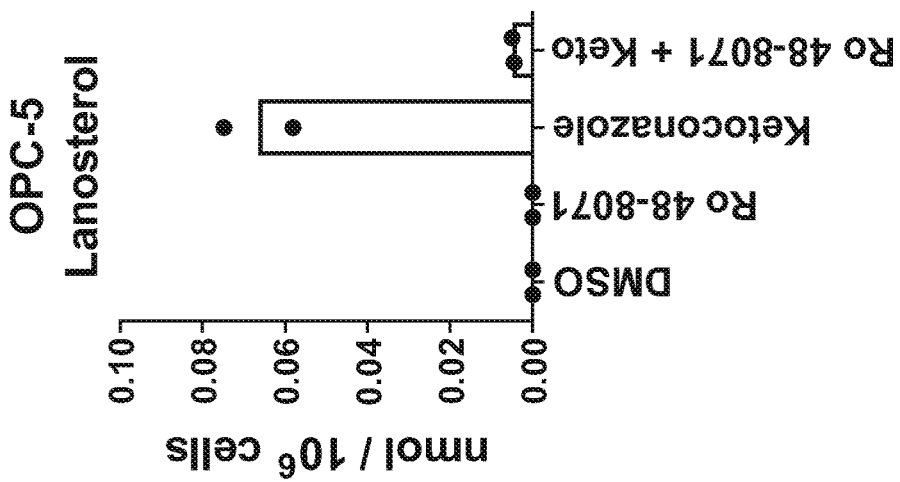
Figure 5E:
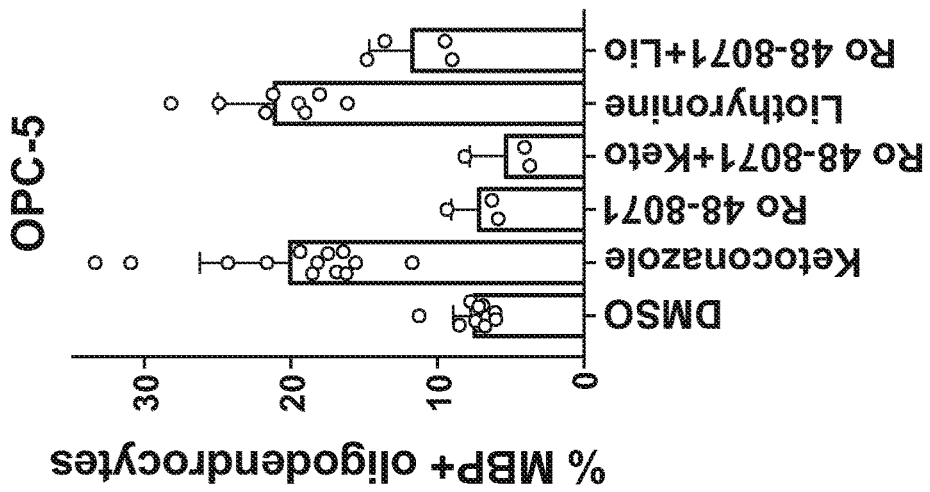

The efficacy of these small molecules and genetic perturbations is not mediated by simple reduction of sterol levels, as statin drugs and various other pathway inhibitors that the inventors confirmed as depleting cholesterol levels did not enhance oligodendrocyte formation from OPCs (FIG. 2B). Likewise, using methyl-β-cyclodextrin to directly complex and remove sterols from OPCs led to reductions in cholesterol levels comparable to pathway inhibitor treatment but had no effect on oligodendrocyte formation (FIG. 5A,B). Because treatment of OPCs with CYP51's substrate lanosterol enhanced oligodendrocyte formation (FIG. 1J), the inventors examined the effects of other purified sterols on OPCs. Direct treatment of OPCs with 14-dehydrozymostenol and zymostenol, which accumulate following inhibition of sterol 14 reductase and EBP, respectively, also enhanced the formation of MBP+ oligodendrocytes. By contrast, other sterols associated with steps downstream of EBP, including cholesterol itself, were ineffective (FIG. 2G, confirmed in FIG. 5C,D). Conversely, preventing the accumulation of 8,9-unsaturated sterols in OPCs abrogated the enhanced oligodendrocyte formation observed from the CYP51 inhibitor ketoconazole. The inventors co-treated OPCs with ketoconazole and Ro 48-8071, which inhibits lanosterol synthase, the enzyme immediately upstream of CYP51 (FIG. 2B). This combination led to a 90% reduction in lanosterol levels relative to ketoconazole alone and also completely suppressed ketoconazole's pro-myelinating effects (FIG. 5E,F). Importantly, Ro 48-8071 treatment alone had little impact on MBP+ oligodendrocyte formation or total cell number in our differentiation assay (FIG. 5E,G). These experiments indicate that accumulation of 8,9-unsaturated sterols, rather than cholesterol depletion, is associated with enhanced oligodendrocyte formation.

Figure 5H:
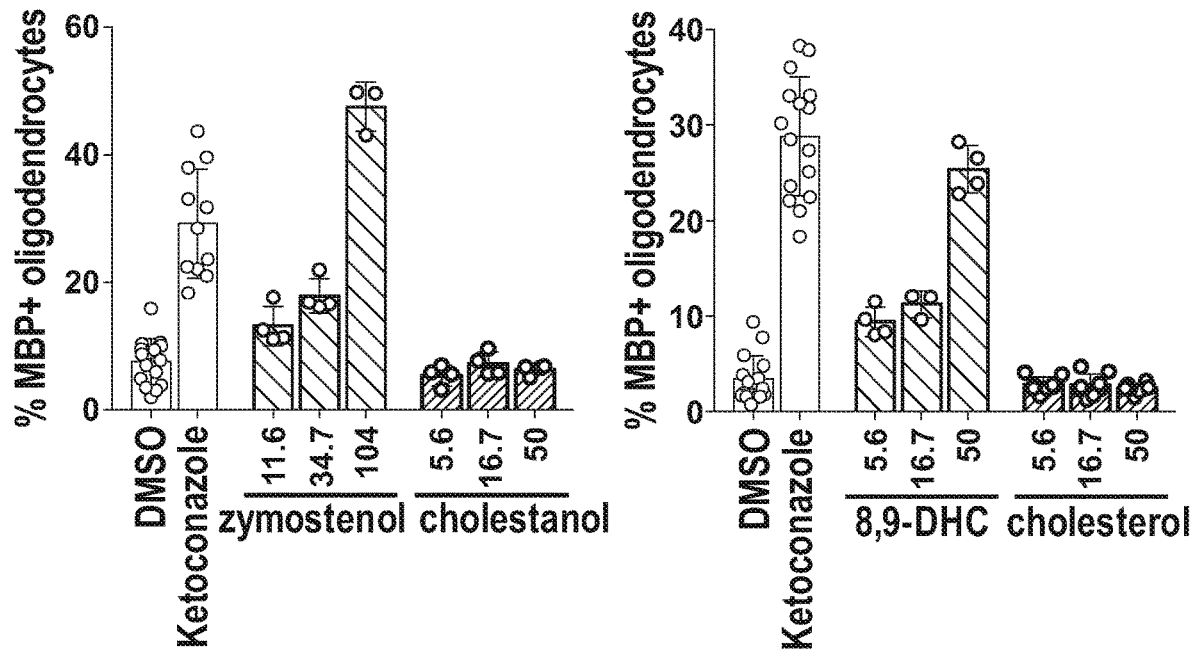
Figure 5I:
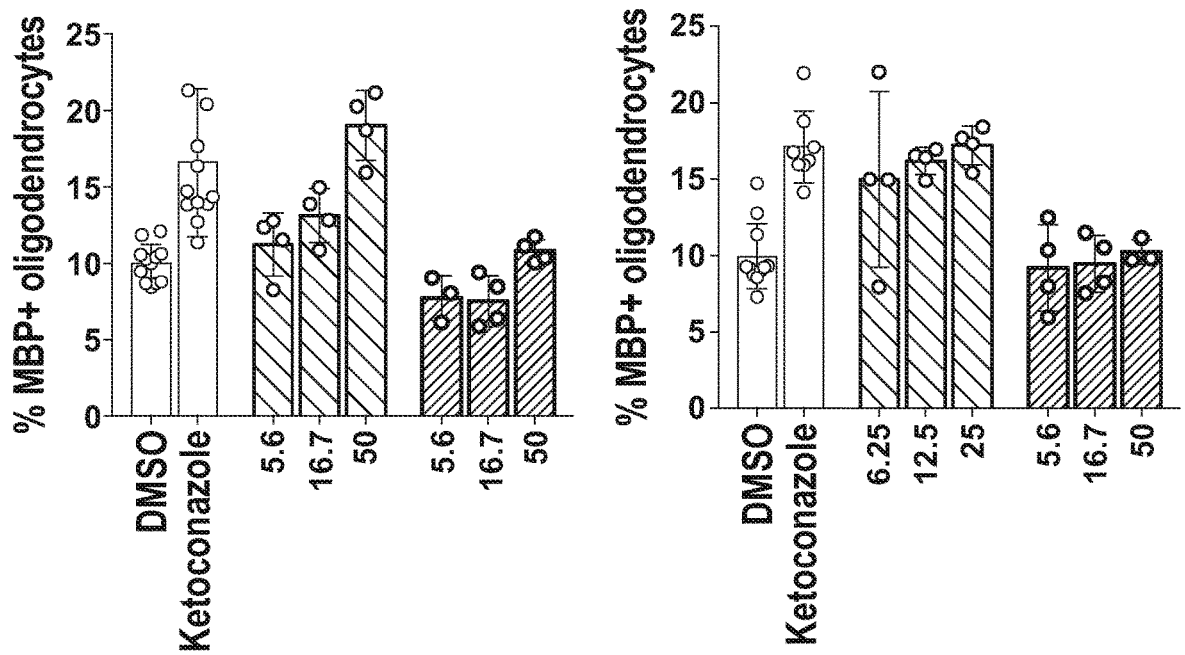
Figure 5J:
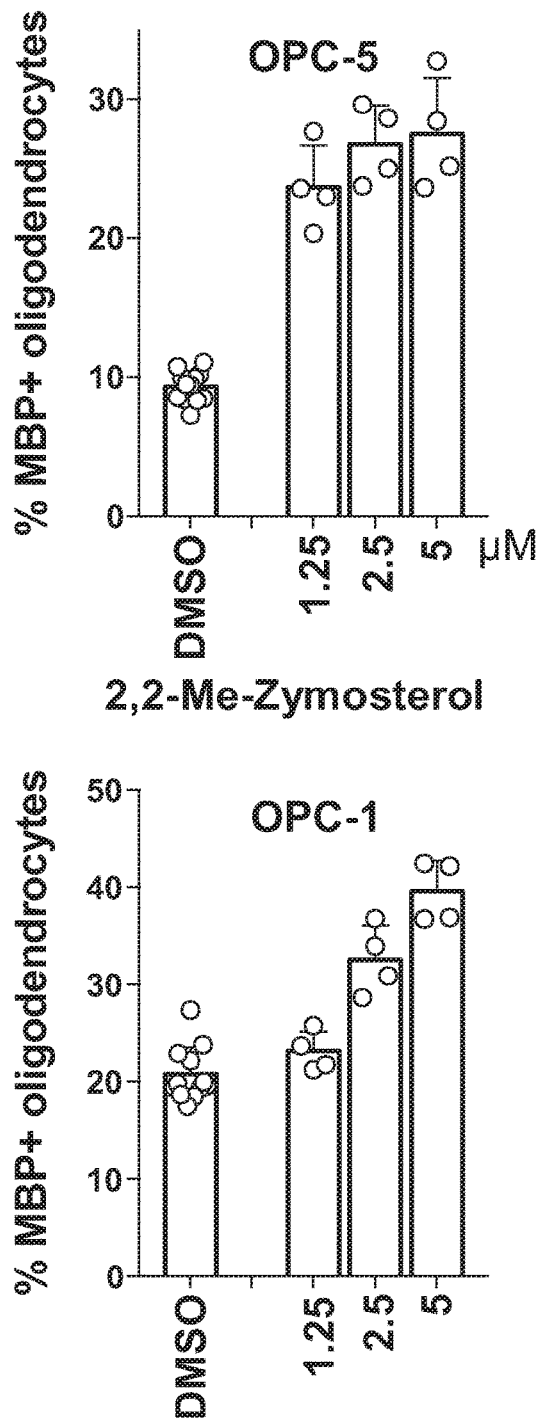
Figure 5K:
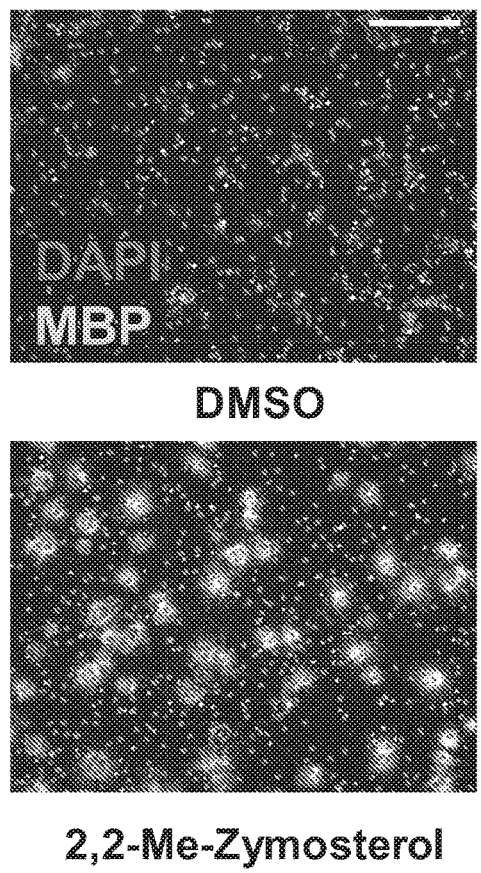
Figure 5K:
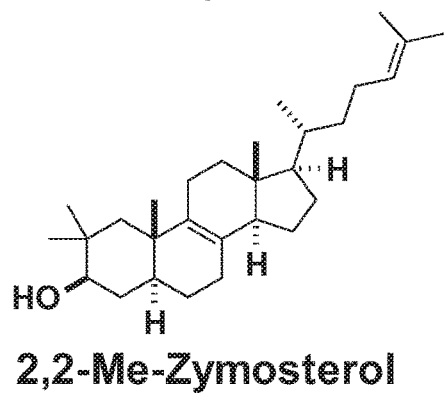
Figure 5L:
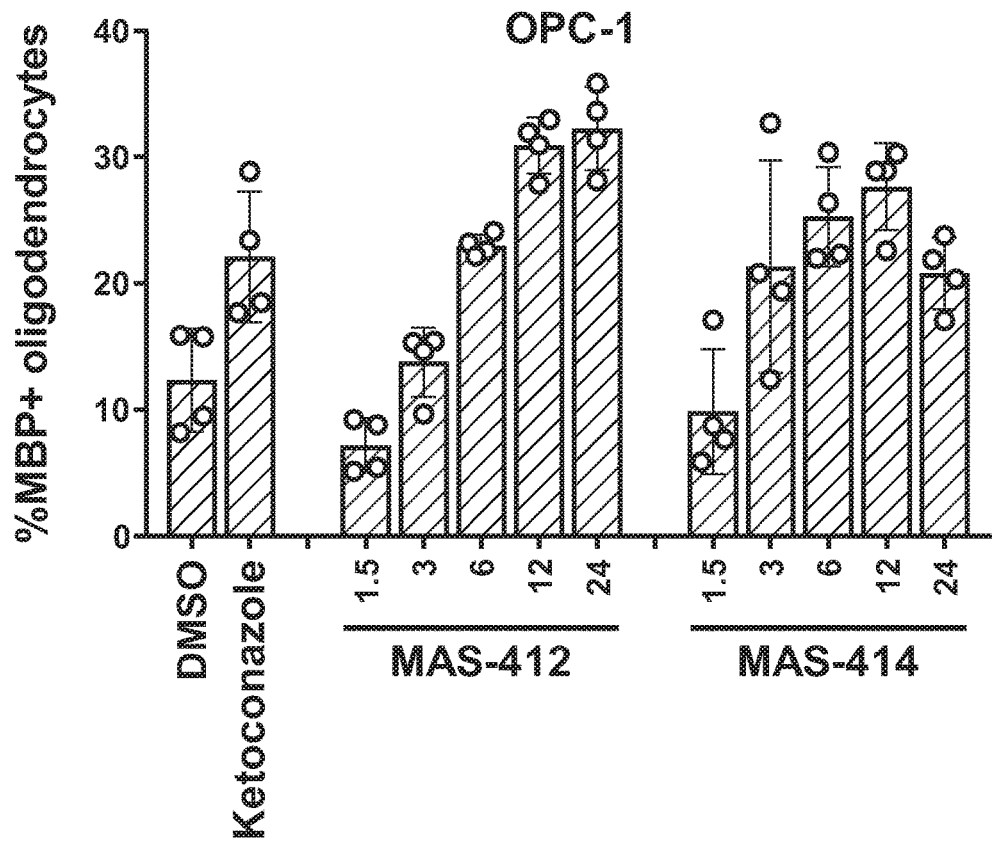
Figure 5M:
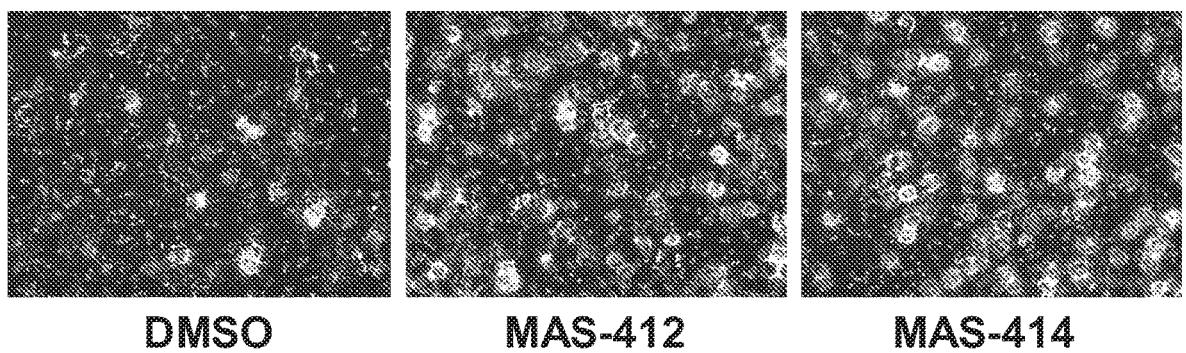
Figure 5N:
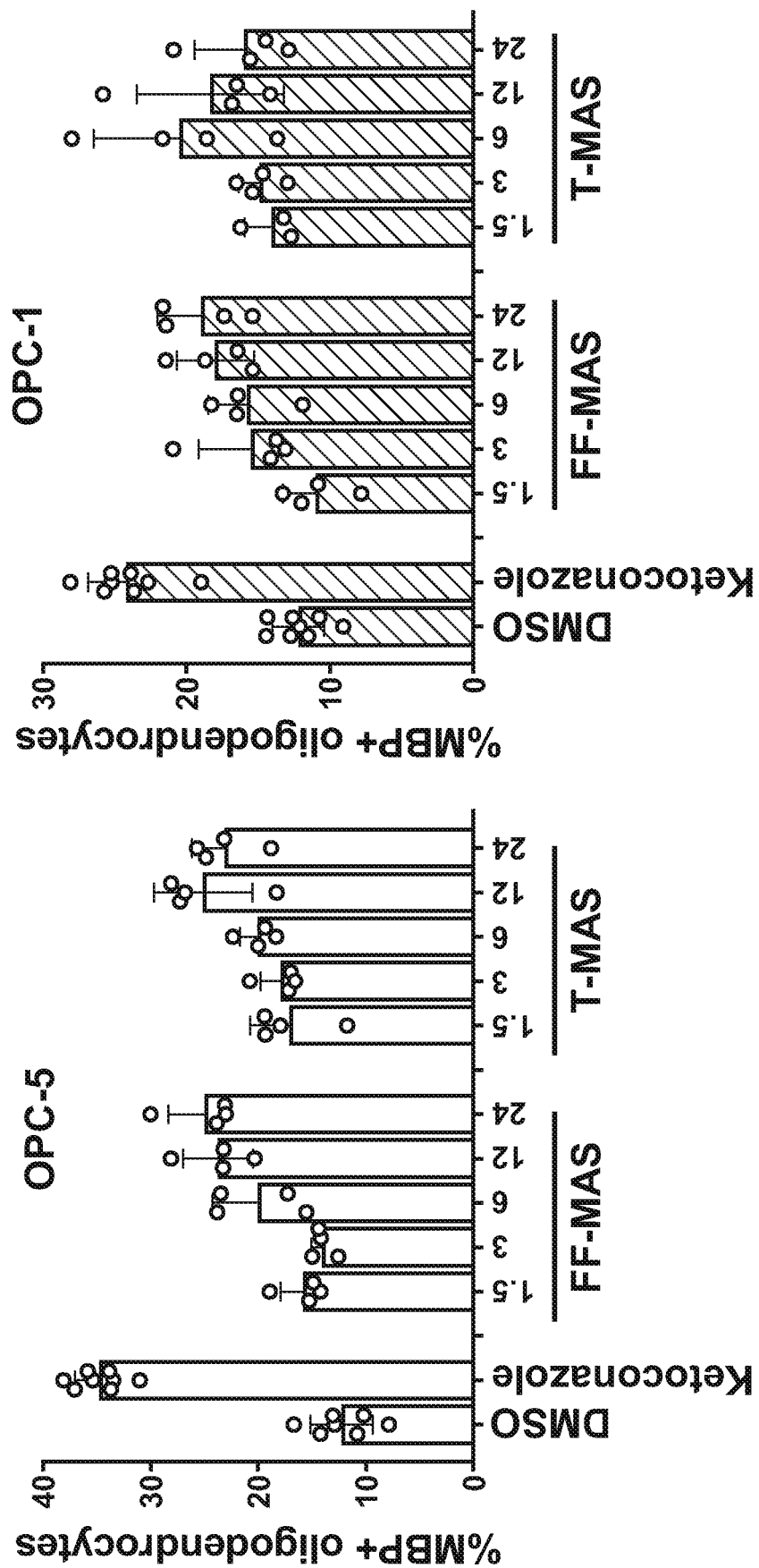
Figure 5O:
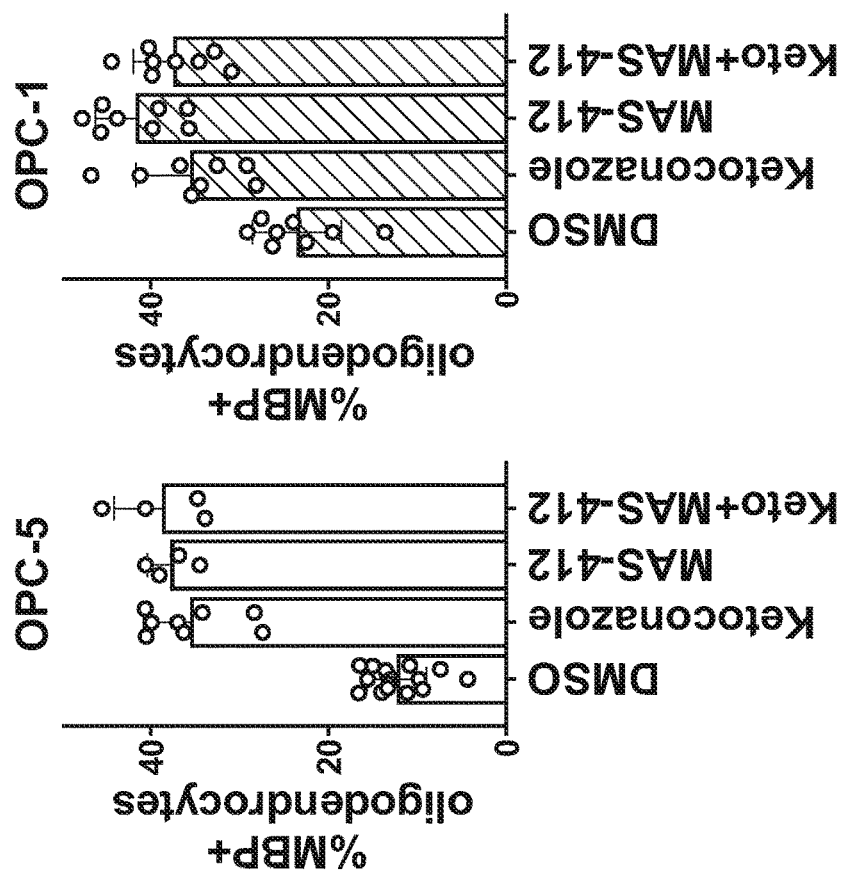
Figure 5P:
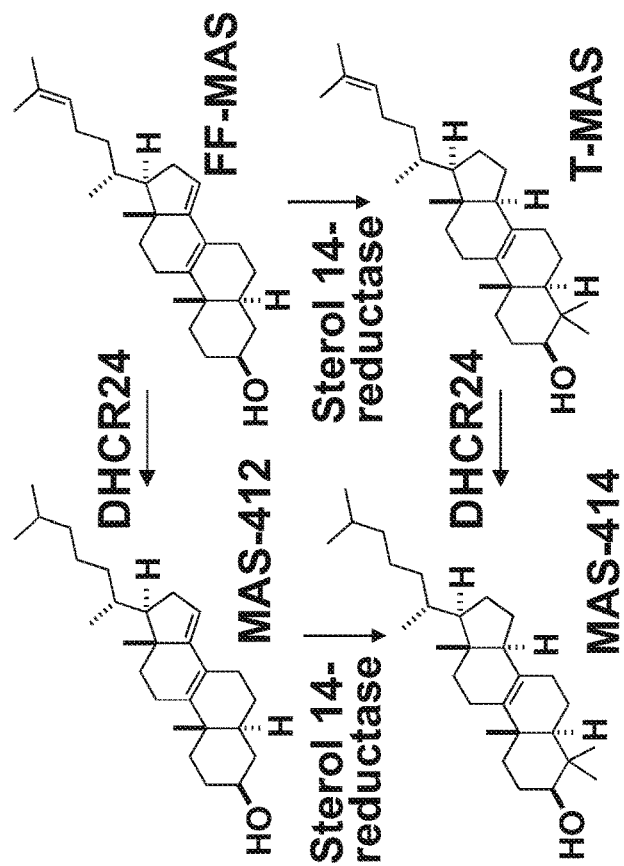

The inventors next examined whether the 8,9 positioning of the double bond is an essential structural feature for efficacy in OPCs. Whereas zymostenol enhanced oligodendrocyte formation, the analogous sterol lacking the 8,9-unsaturation (5-cholestanol) had no effect on OPCs (FIG. 5H,I). Additionally, the inventors established that 8,9-dehydrocholesterol, which is not a canonical intermediate in cholesterol biosynthesis, robustly enhanced oligodendrocyte formation, while the otherwise identical sterol lacking the 8,9 unsaturation, cholesterol, had no effect on OPCs (FIG. 5H,I). Additional non-natural 8,9-unsaturated sterols also enhance oligodendrocyte formation. In addition to 8,9-dehydrocholesterol described above, 2,2-dimethylzymosterol shows optimal potency among all sterols evaluated to date ($EC_{50}$ 1-2 μM, a FIG. 5J,K). Co-treating OPCs with ketoconazole and 2,2-dimethylzymosterol provided no further benefit over ketoconazole alone, confirming that this representative cholesterol pathway inhibitor and optimal 8,9-unsaturated sterol function by overlapping mechanisms (FIG. 5L). Together these findings indicate that the accumulation of 8,9-unsaturated sterols in OPCs is a central mechanism for enhancing oligodendrocyte formation whether these sterols arise from small-molecule inhibition of cholesterol biosynthesis enzymes or are supplied to OPCs in purified form.

The inventors noted several 8,9-unsaturated sterols that enhance oligodendrocyte formation, including 14-dehydrozymostenol and zymostenol, had previously been shown to function as signaling lipids in oocytes by inducing the resumption of meiosis. However, the canonical 'meiosis-activating sterols', FF-MAS, T-MAS, MAS-412, and MAS-414, do not accumulate in OPCs following the small-molecule inhibitor treatments. Supplying OPCs with each of these four meiosis activating sterols in purified form led to enhanced oligodendrocyte formation, with MAS-412 and MAS-414 having optimal efficacy and potency among all canonical cholesterol biosynthesis intermediates evaluated (FIG. 2H, FIG. 5M-P). The broad efficacy of 'meiosis-activating sterols' to promote oligodendrocyte formation suggests that these bioactive sterols also guide cell fate transitions in OPCs.

Figure 6A:
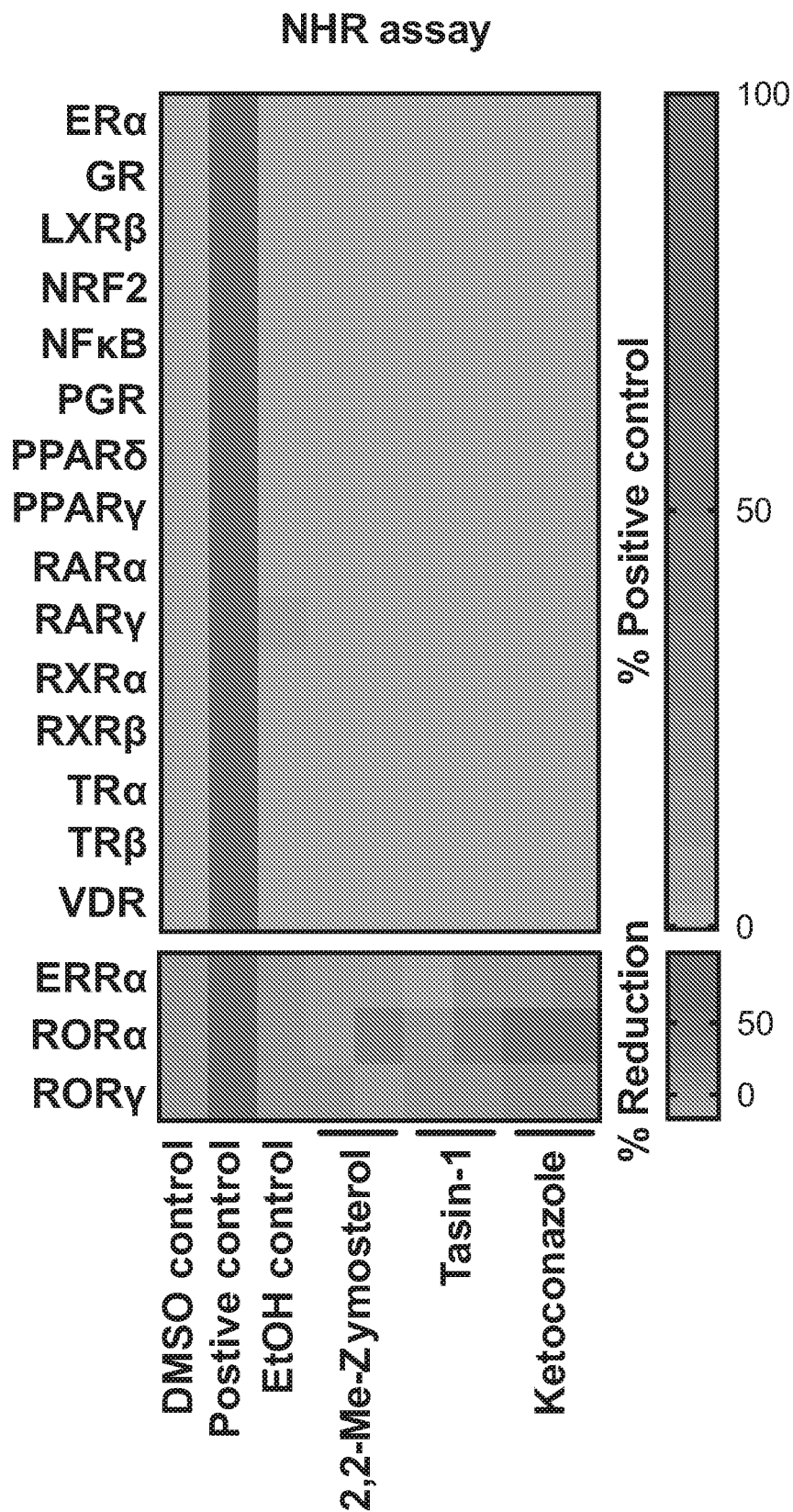
FIGS. 6(A-D) illustrate images and graphs showing the effect of 8,9-unsaturated sterols on nuclear hormone receptors and SREBP2 activity: a) Luciferase reporter assays were used to assess if 2,2-Dimethylzymosterol (5 μM), Ketoconazole (2.5 μM), and TASIN-1 (250 nM) modulate human ERα, GR, LXRβ, NFkB, NRF2, PGR, PPARδ, PPARγ, RARα, RARγ, RXRα, RXRβ, TRα, TRβ and VDR transcriptional activity in agonist mode and ERRα, RORα and RORγ in inverse-agonist mode. Measurements are shown as percentage of positive control, n=2 replicates per condition and n=3 replicates per condition for the controls. b) Effects of sterols (T-MAS 5 μM, FF-MAS 10 μM) and small molecules (Ketoconazole 2.5 μM, TASIN-1 100 nM) on the NR2F1-mediated activation of a NGFI-A promoter driven luciferase reporter in comparison to cells containing the reporter only (Ctrl.) or untreated. n=2 replicates per condition, with triplicate measurements per replicate. c) Effects of 2,2-dimethylzymosterol (5 μM) on the NR2C2 mediated activation of a NGFI-A promoter driven luciferase reporter in comparison to cells infected with reporter only, untreated, or treated with a previously reported positive control (all-trans retinoic acid, ATRA, 5 μM). n=2 replicates per condition, with triplicate measurements per replicate. d) LSS, DHCR7, LDLR mRNA levels measured by RT-qPCR following 24 h treatment with DMSO, Mevastatin (2.5 μM), Ro 48-8071 (500 nM), Ketoconazole (2.5 μM), TASIN-1 (100 nM), or Amorolfine (100 nM). n=2 replicates, with triplicate qPCR measurements per replicate. Experiments in panels b-d are representative of two indpedendent experiments.
Figure 6B:
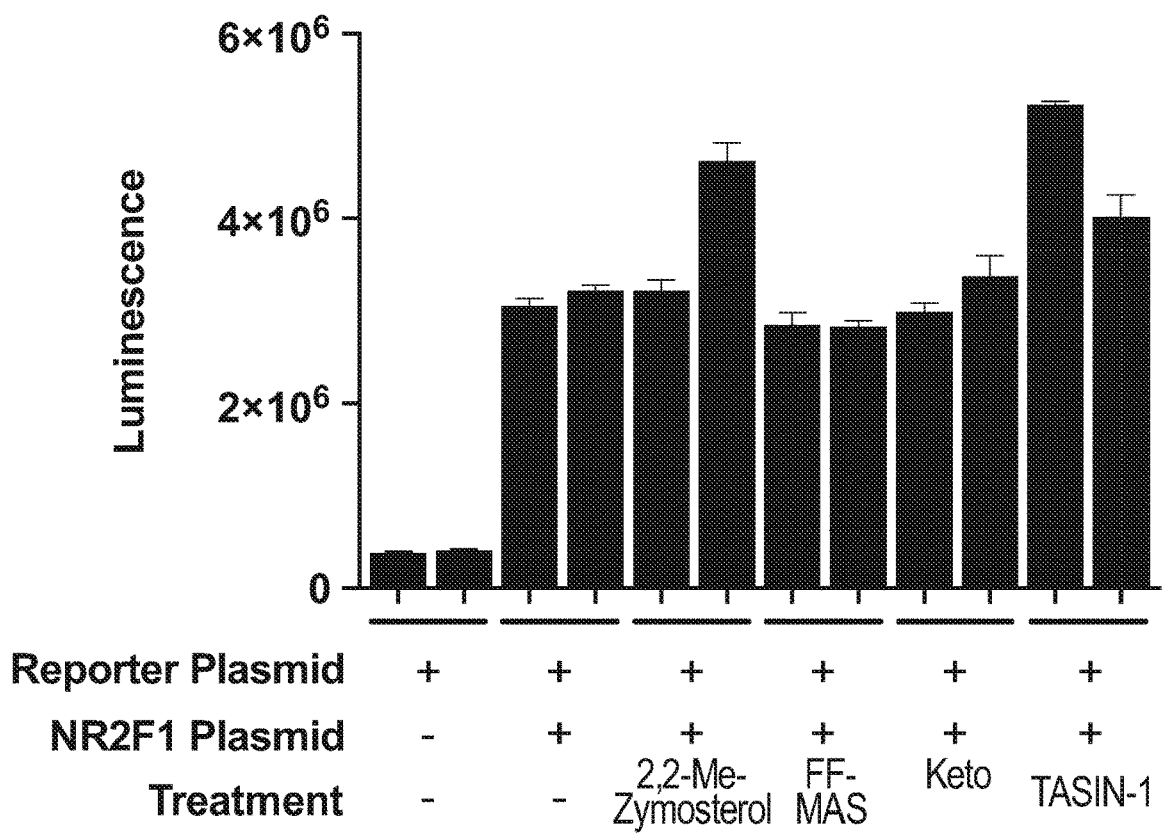
Figure 6C:
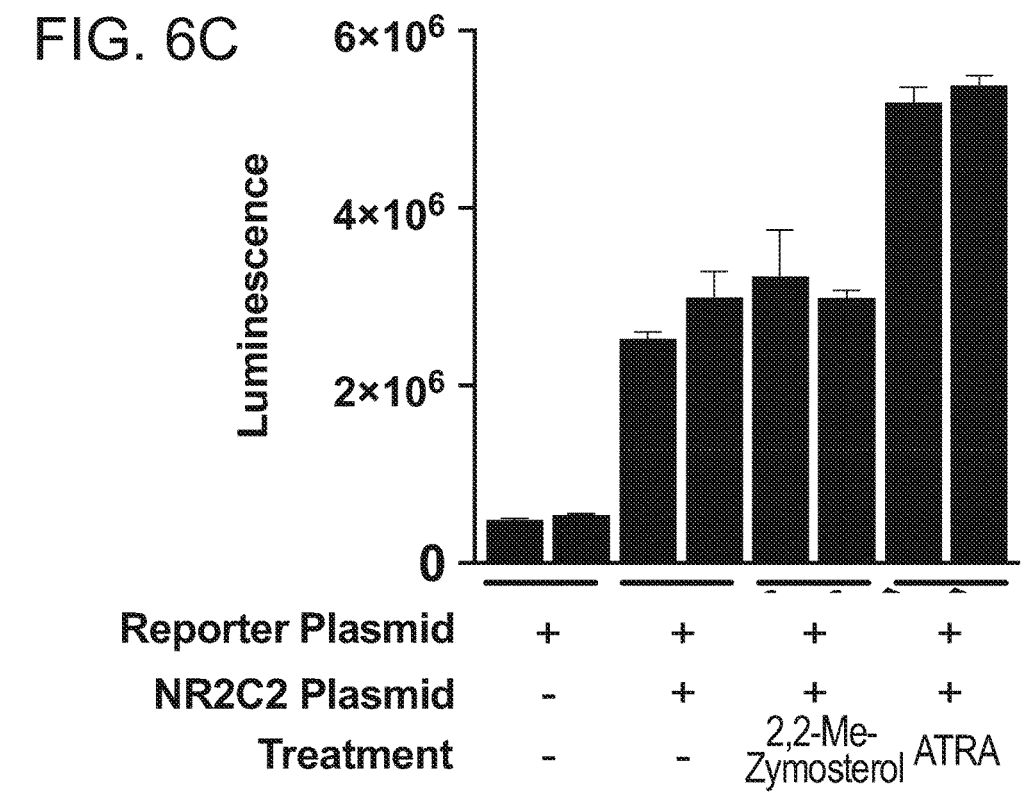
Figure 6D:
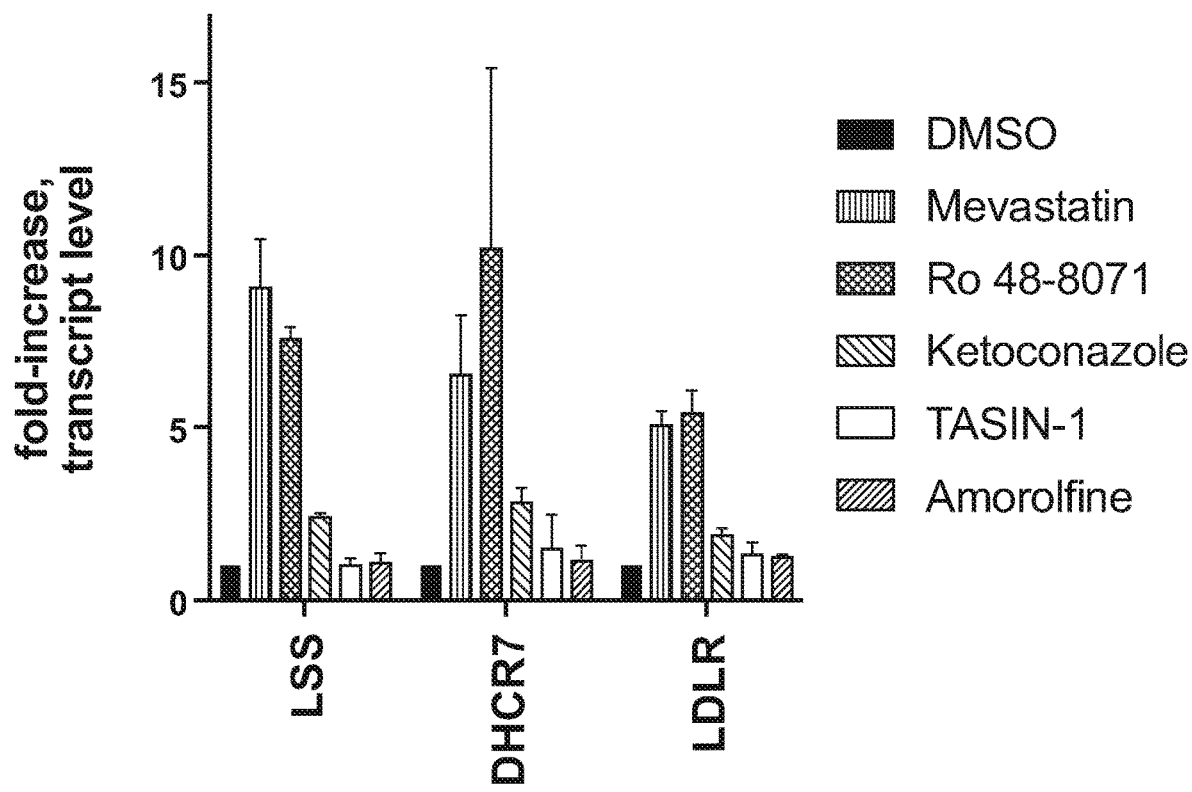

While the direct cellular targets of 8,9-unsaturated 'meiosis-activating sterols' remain poorly understood, past work suggested nuclear hormone receptors, in particular LXR, may play a role. The inventors evaluated 2,2-dimethylzymosterol and the pathway inhibitors ketoconazole and TASIN-1 in cell-based reporter assays for 18 well-studied NHRs, including the LXRβ isoform expressed in OPCs, but no molecule showed significant agonist activity in any assay (FIG. 6A). These molecules were also ineffective in reporter assays for two 'orphan' NHRs (NR2F1 and NR2C2) previously linked to myelin formation by mouse knockout experiments but whose endogenous ligand is unknown, suggesting that the meiosis-activating sterols may target other families of sterol-binding proteins (FIG. 6B, 6C). SREBP2 transcriptionally regulates cholesterol homeostasis by interacting with the sterol-sensing proteins SCAP and INSIG and has been shown to play a role in oligodendrocyte formation. However, canonical SREBP2 target genes were upregulated much more strikingly by inhibitors of the upstream pathway enzymes HMGCoA reductase and squalene synthase than by inhibitors of CYP51, sterol 14 reductase, or EBP, making SREBP2 an unlikely mediator of 8,9-unsaturated sterols' effects in OPCs (FIG. 6D). Together these studies suggest a novel role for the 'meiosis-activating sterols' in regulating oligodendrocyte formation and identify FF-MAS and 2,2-dimethylzymosterol as maximally potent enhancers of oligodendrocyte formation among the 8,9-unsaturated sterols tested.

In parallel, the inventors executed a screen of over 3,000 bioactive small molecules and approved drugs at a uniform dose of 2 μM. This library contains many approved drugs screened previously, as well as a wide range of non-approved drug candidates and well-annotated chemical probes.

Among the hits, the inventors obtained nine imidazole antifungals as well as other molecules previously annotated as enhancing OPC differentiation, including clemastine. The inventors also identified many confirmed hits with known targets that did not cluster into easily discernible categories. Among molecules not previously reported to modulate OPC differentiation, our top hit was EPZ005687, an inhibitor of the histone methyltransferase EZH2 (enhancer of zeste 2). EPZ005687 robustly enhanced oligodendrocyte formation in both our mouse epiblast stem cell-derived OPCs and mouse primary OPCs. Surprisingly, the inventors verified that three structurally analogous EZH2 inhibitors had no effect on OPC differentiation, suggesting that although EZH2 has previously been shown to play a role in oligodendrocyte formation, EPZ005687 functioned in OPCs by an idiosyncratic off-target effect beyond EZH2. The inventors examined the effects of these four EZH2 inhibitors in our GC/MS-based sterol profiling assay and found that EPZ005687 uniquely caused accumulation of zymosterol and zymostenol in OPCs, indicating that EPZ005687 acts as an EBP inhibitor in OPCs. Among these four closely-related EZH2 inhibitors, EPZ005687 alone inhibits EBP in OPCs and enhances the formation of oligodendrocytes.

Figure 3A:
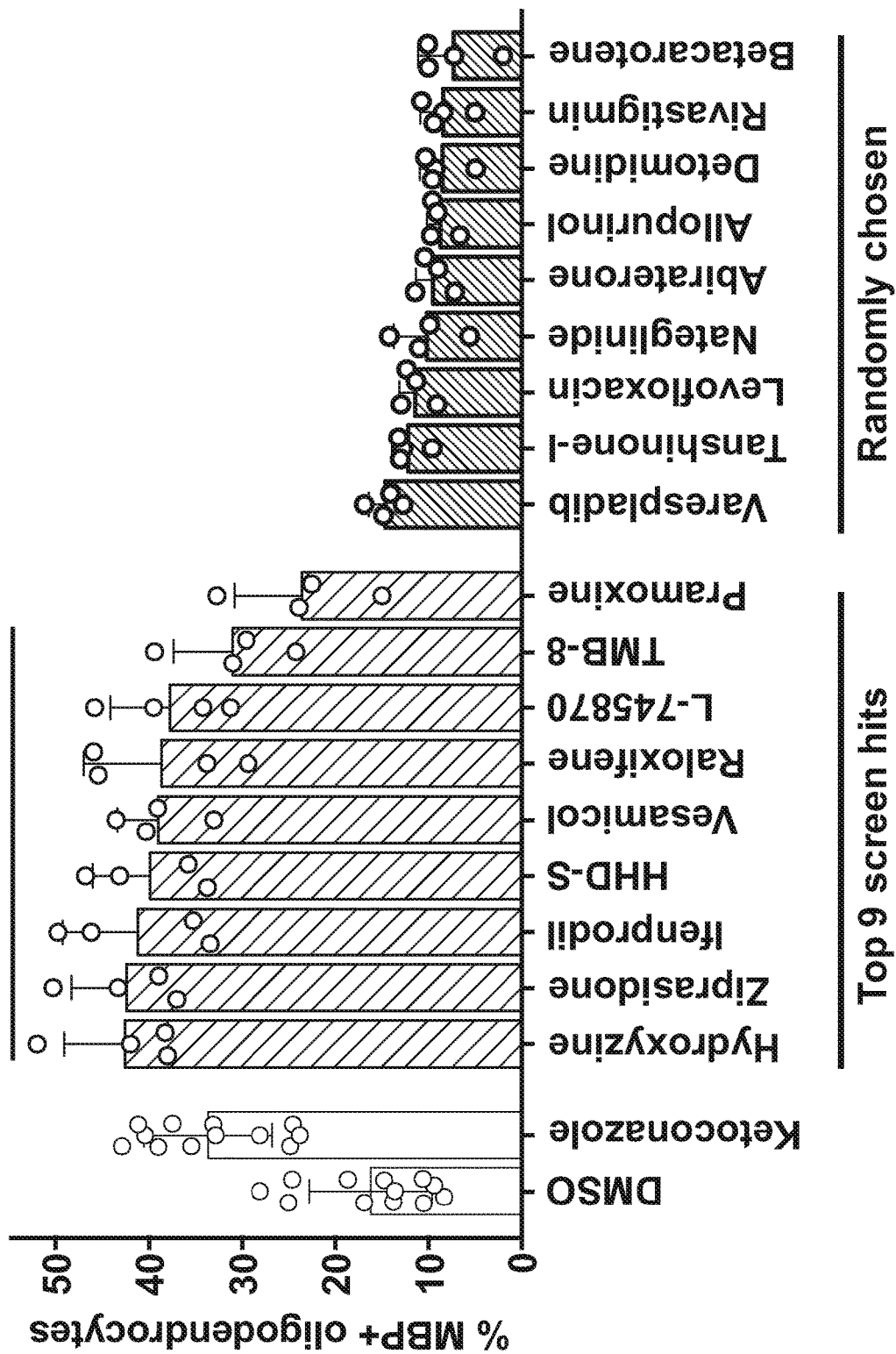
FIGS. 3(*a-f*) illustrate graphs showing inhibiting steps between CYP51 and EBP is a unifying mechanism for many small enhancers of oligodendrocyte formation identified by high-throughput screening. a) Percentage of MBP$^+$ oligodendrocytes generated from OPCs at 72 h following treatment with ketoconazole, nine molecules identified by bioactives screening (green), and nine randomly chosen library members (red) at a uniform dose of 5 μM. n=4 replicates per condition, with >1,000 cells analyzed per replicate. *, P<0.01, t-test. b) GC/MS-based quantitation of zymosterol, zymostenol, and 14-dehydrozymostenol levels in OPCs treated 24 h with the indicated screening hits and randomly chosen library members at 2 μM. One replicate per condition, with findings confirmed in a second OPC derivation (FIG. 5B). Molecules are clustered by enzyme targeted (top labels). c) GC/MS-based quantitation of zymostenol levels in OPCs treated 24 h with the indicated previously-reported enhancers of oligodendrocyte formation. Unless otherwise noted, the following concentrations were used: benztropine, 2 μM; clemastine 1 μM; tamoxifen 100 nM; U50488 5 μM; bexarotene, 1 μM; liothyronine, 3 μM. d) GC/MS-based quantitation of cholesterol levels in OPCs treated 24 h with the indicated previously-reported enhancers of oligodendrocyte formation. e) GC/MS-based quantitation of EBP enzymatic activity in a biochemical assay following treatment with small molecules (10 μM) that inhibit EBP in OPCs (green) or do not inhibit EBP in OPCs (red). n=3. f) Percentage of MBP$^+$ oligodendrocytes generated from OPCs at 72 h following treatment with the indicated combinations of enhancers of oligodendrocyte formation. n=4 replicates per treatment condition, with >1,000 cells analyzed per replicate. Keto=ketoconazole, 2.5 μM. All bar graphs indicate mean+/−standard deviation. Cell-based experiments were performed in the OPC-5 derivation, panels c-f are representative of two independent experiments, and all findings have been confirmed in a second independent derivation of OPCs (FIG. 5). Sigma H127, p-Fluorohexahydro-sila-difenidol.
Figure 3B:
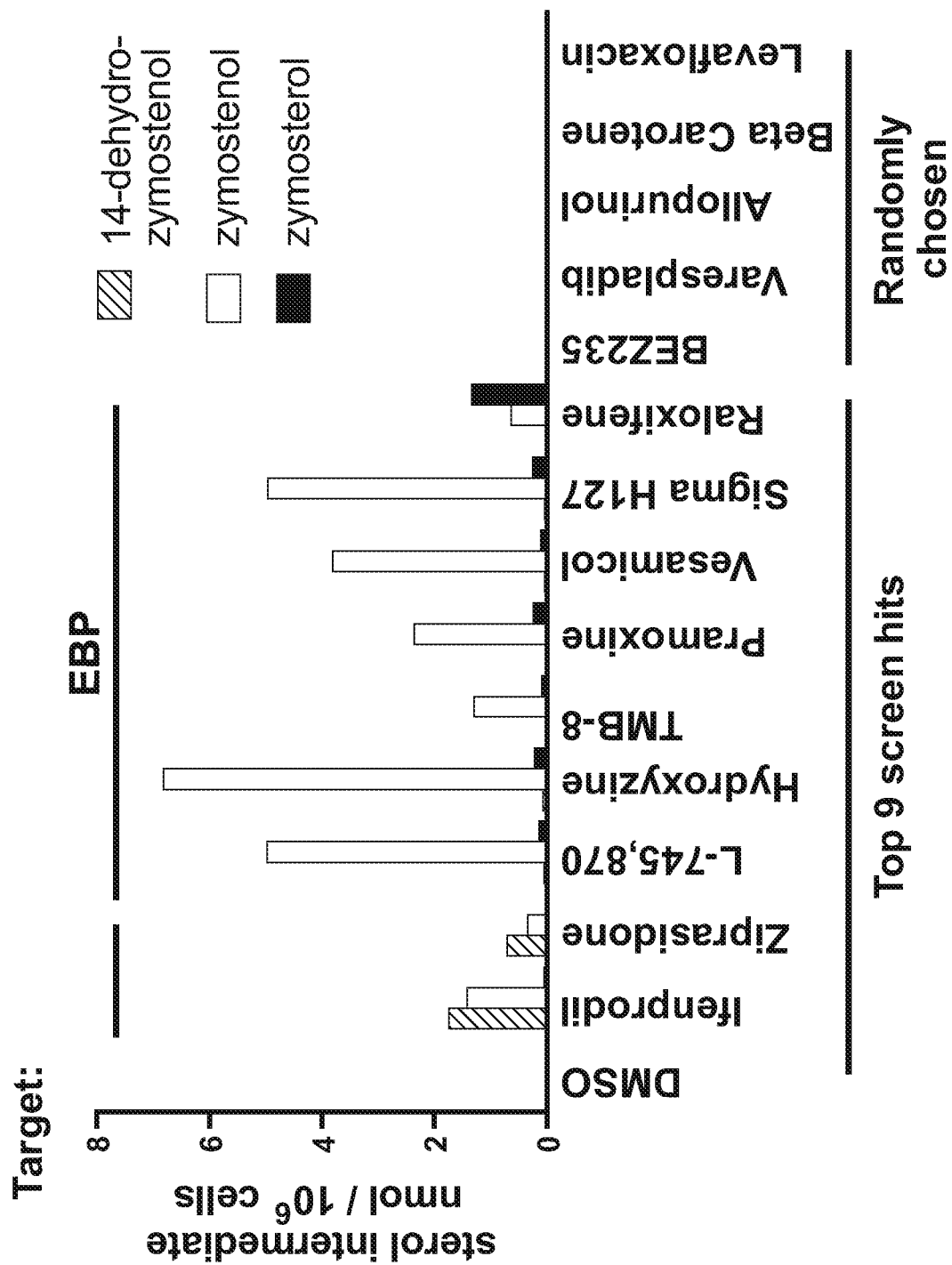

The inventors further examined the top 10 confirmed hits after EPZ005687 (exclusive of imidazole antifungals and other molecules identified in previously published screens) and found that all 10 induced altered sterol profiles at the screening dose (FIG. 3A-B). Seven molecules inhibited EBP, two molecules inhibited sterol 14-reductase activity, and one molecule (fulvestrant) targeted CYP51. Four of these molecules have previously been shown to modulate sterol 14-reductase or EBP activity in CNS-derived cells: ziprasidone, ifenprodil, hydroxyzine, and raloxifene. Among 10 library molecules that the inventors confirmed do not affect OPC differentiation to oligodendrocytes at the screening dose, none enhanced levels of 8,9-unsaturated sterol intermediates (FIG. 3A-B). These data show that accumulation of 8,9-unsaturated sterols is a dominant mechanism-of-action for enhancing the formation of oligodendrocytes among small molecules identified by high-throughput screening.

Figure 3C:
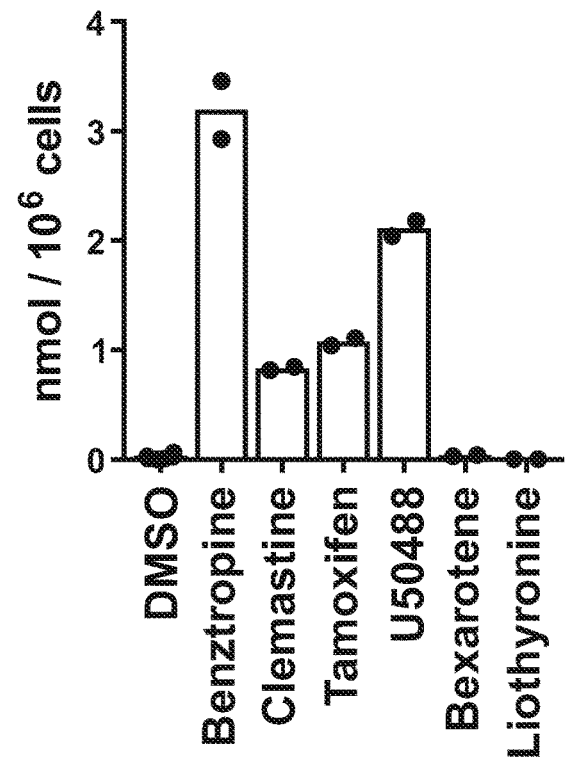
Figure 3D:
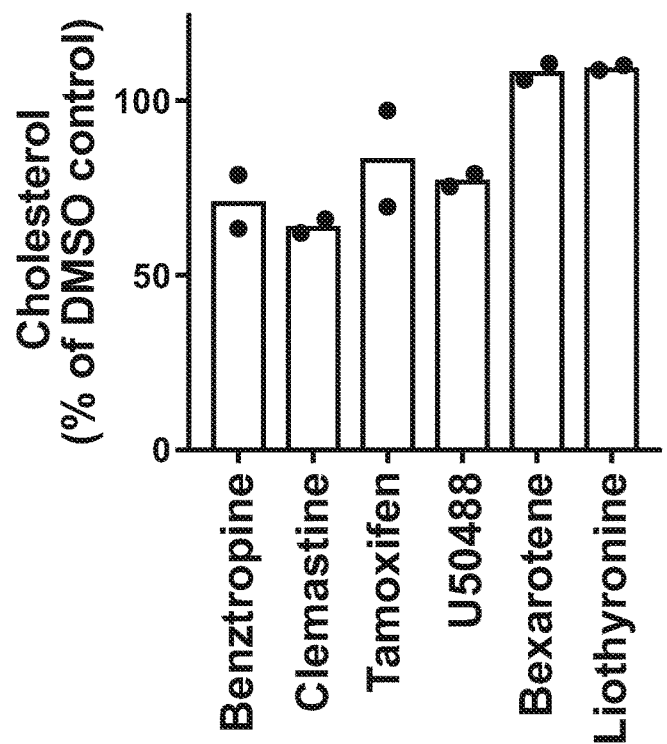

Given the frequency of cholesterol pathway modulators within the top screening hits, the inventors assessed whether any previously-reported enhancers of remyelination identified by HTS might also induce sterol intermediate accumulation. The inventors assembled a collection of molecules reported to induce OPC differentiation through a variety of canonical targets: benztropine (muscarinic receptor), clemastine ($H_1$ receptor and muscarinic receptor), tamoxifen (estrogen receptor), U50488 (κ-opioid receptor), bexarotene (retinoid-X receptor, RXR), and liothyronine (thyroid hormone receptor). The inventors identified the dose at which each molecule shows near-maximal upregulation of oligodendrocyte formation and then evaluated each molecule in our GC/MS sterol profiling assay). Benztropine, clemastine, tamoxifen, and U50488 induced accumulation of zymostenol and zymosterol and decreased basal sterol levels, indicative of inhibition of EBP in OPCs (FIG. 3C-D). Tamoxifen has been shown previously to inhibit EBP in a biochemical assay, in cell culture models, and in cancer patients undergoing chemotherapy. By contrast, liothyronine and bexarotene showed minimal effects on sterol levels, consistent with their known functions as regulators of transcription factor function and confirming that many, but not all, treatments that enhance oligodendrocyte formation cause sterol intermediate accumulation.

Figure 3E:
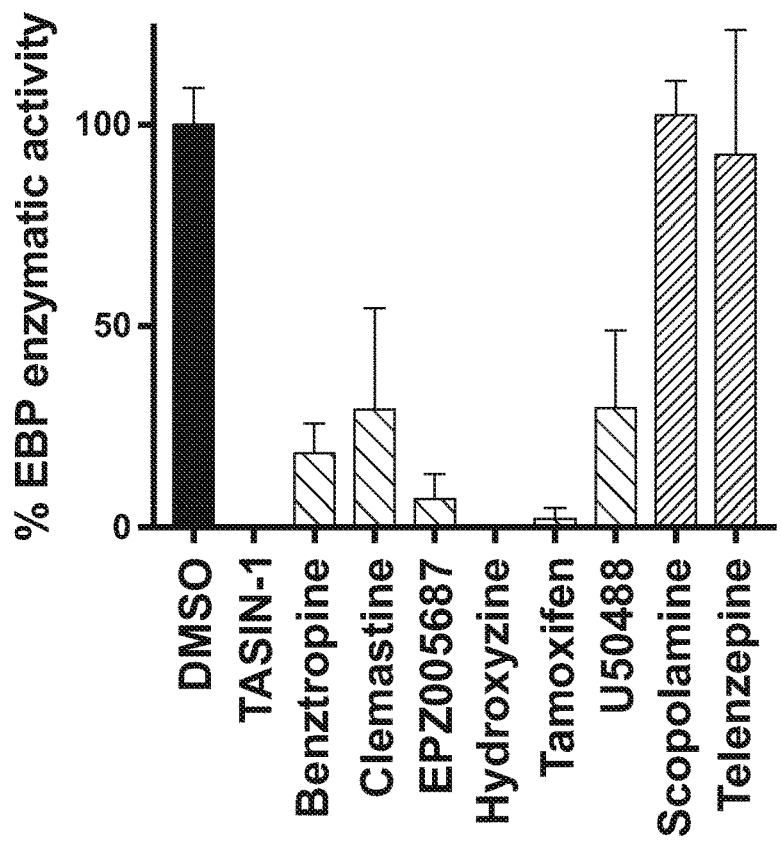

Inhibition of EBP in OPCs following treatment with clemastine, tamoxifen, or other small molecules could result from direct targeting of EBP or could reflect a downstream consequence of each molecule inhibiting its canonical protein target. The inventors assessed direct inhibition of EBP in vitro using a GC/MS-based biochemical assay of EBP enzymatic activity. The inventors observed clear inhibition by the selective EBP inhibitor TASIN-1 as well as by benztropine, clemastine, tamoxifen, and U50488, with more potent cellular EBP inhibitors showing a greater magnitude of inhibition (FIG. 3E). The inventors also annotated two molecules identified in our bioactives screen, EPZ005687 and hydroxyzine, as directly inhibiting EBP enzymatic activity in this biochemical assay, suggesting that many enhancers of oligodendrocyte formation directly target EBP in OPCs.

The inventors sought additional evidence that muscarinic receptor antagonists and selective estrogen receptor modulators (SERMs) mediate enhanced oligodendrocyte formation in OPCs by acting on EBP as their functional target. Although clemastine and benztropine have been validated as inducers of OPC differentiation to oligodendrocytes, previous work suggested that many other muscarinic receptor antagonists do not share this functional property. Using the bioactives screening data, the inventors selected four muscarinic receptor antagonists with varying isoform selectivity and independently confirmed that all four do not enhance $MBP^+$ oligodendrocyte generation at 2 μM. However, in independent cellular activity assays performed at the same concentration, these four molecules and clemastine showed comparable, near-complete inhibition of the muscarinic receptor M1, M3, and M5 isoforms, suggesting that muscarinic receptors may not be the functional target in OPCs. In contrast to clemastine and benztropine, which enhance 8,9-unsaturated sterol accumulation and directly inhibit EBP enzymatic activity, muscarinic receptor antagonists that do not enhance oligodendrocyte formation do not cause accumulation of zymostenol or other sterol intermediates in OPCs, and no inhibition of EBP was observed in an enzymatic activity assay (FIG. 3E). These findings suggest that only muscarinic receptor antagonists that inhibit EBP can enhance formation of oligodendrocytes.

The ability to inhibit EBP in OPCs also predicts enhanced formation of oligodendrocytes among selective estrogen receptor modulators (SERMs). The inventors evaluated two FDA-approved SERMs, toremifine and ospemifine, that they validated as having comparable cellular antiestrogenic potency and that are structurally identical except for ospemifine's substitution of a primary alcohol for toremifine's tertiary amine functionality. The inventors confirmed that toremifene inhibited EBP and also enhanced $MBP^+$ oligodendrocyte generation over a wide dose range. Strikingly, ospemifine had no effect on OPC differentiation and did not inhibit EBP, likely because it lacks a cationic functionality able to mimic EBP's sterol C8 cation-like transition state. Additionally, the inventors have established that both tamoxifen and 4-hydroxytamoxifen inhibit EBP in OPCs and enhance the formation of oligodendrocytes with comparable potency. Because 4-hydroxytamoxifen is 100-fold more potent than tamoxifen as an estrogen receptor modulator, the comparable potency of these molecules for enhancing oligodendrocyte formation further discounts a functional role for the estrogen receptor in the enhanced oligodendrocyte formation observed for these SERMs. These results demonstrate that among structurally near-identical SERMs the ability to inhibit EBP, and not modulation of the estrogen receptor, predicts enhanced oligodendrocyte formation.

Figure 3F:
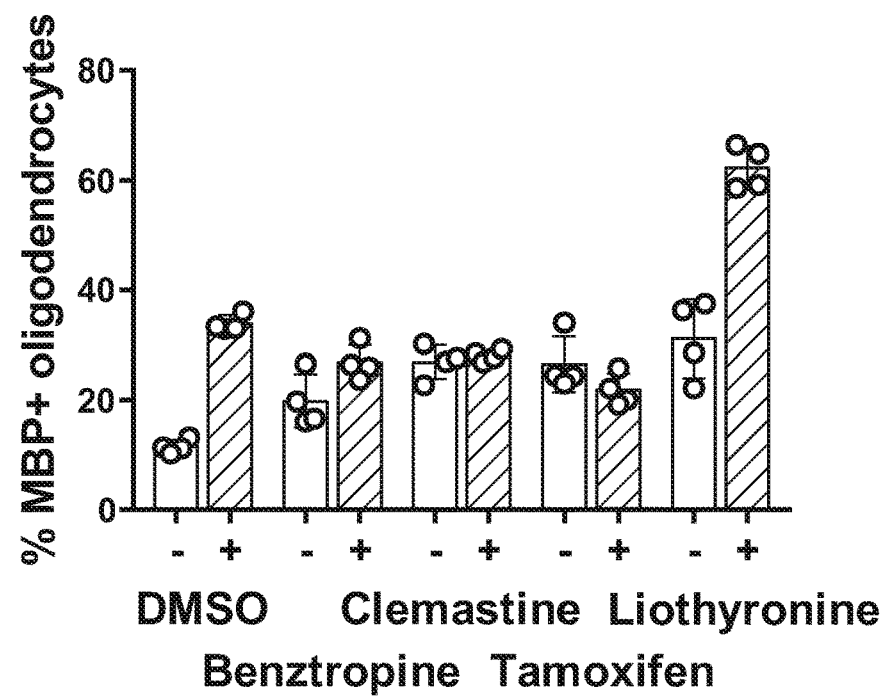

Because the results described herein suggest that sterol modulation is a shared function of many (but not all) compounds that enhance oligodendrocyte formation, the inventors tested the potential for combinations of small molecules to show additive or non-additive effects. Combining the thyroid hormone agonist liothyronine with a range of sterol-modulating OPC differentiation-inducing treatments produced additive effects on oligodendrocyte formation, indicating that these molecules likely function by mechanisms other than thyroid hormone receptor signaling to enhance oligodendrocyte generation. In contrast, combinations of ketoconazole at a maximally effective dose with any of four previously-reported enhancers of OPC differentiation (benztropine, clemastine, tamoxifen, and U50488) did not enhance differentiation above levels seen for ketoconazole alone (FIG. 3F). This non-additive effect is consistent with these molecules sharing 8,9-unsaturated sterol accumulation as a common mechanism for induction of oligodendrocyte formation. By inhibiting pathway flux at CYP51 with ketoconazole, inhibitors of EBP can no longer cause further sterol accumulation or enhance oligodendrocyte formation.

Since our in vitro OPC assays only model the initial differentiation event into oligodendrocytes, the inventors next tested whether sterol pathway modulation also enhanced subsequent oligodendrocyte maturation and myelination in vitro and in vivo. The inventors cultured OPCs for 14 days on electrospun microfibers to assess the effects of sterol pathway modulators on oligodendrocytes' ability to track and wrap along axon-like substrates. Ketoconazole (CYP51), amorolfine (sterol 14-reductase), and TASIN-1 (EBP), each of which function to accumulate sterol intermediates in OPCs, significantly enhanced MBP+ oligodendrocyte tracking along and wrapping of the microfibers. Inhibition of other enzymes, up- or downstream in the pathway, had no effect on oligodendrocyte maturation and ensheathment of microfibers.

Figure 4B:
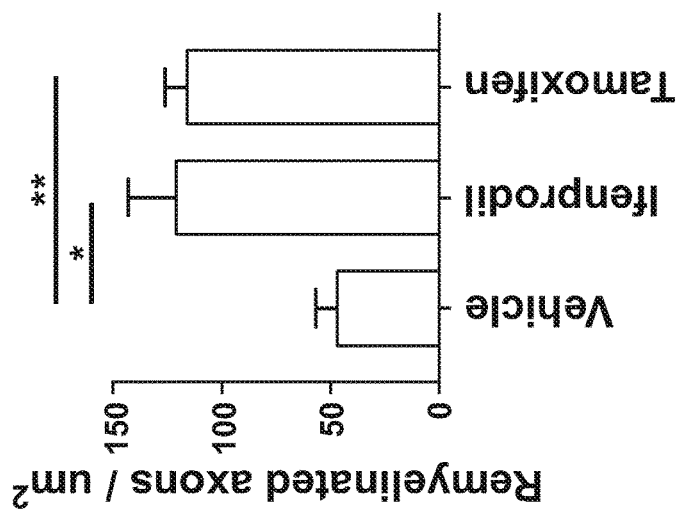
FIGS. 4(*a-f*) illustrate graphs and images showing the effect of small molecules on sterol intermediate accumulation and enhancement of remyelination in vivo. a) GC/MS-based quantitation of sterol levels in mouse brain following daily dosing with miconazole (10 mg per kg), ifenprodil (10 mg per kg), and tamoxifen (2 mg per kg) for three days. n=4 animals per group. b) Quantitation of remyelinated axons within toluidine blue stained sections of LPC-lesioned spinal cord from mice treated 8 days with molecules at the doses stated in panel a. n=6 animals per group except vehicle, n=4. Data are presented as mean+/−S.E.M. c) Representative images of toluidine blue stained sections of LPC-lesioned dorsal spinal cord from mice treated 8 days with molecules at doses stated in panel a. Scale bar, 20 μm. d) Representative electron microscopy images of sections of LPC-lesioned dorsal spinal cord from mice treated 8 days with molecules at doses stated in panel a. Scale bar, 5 μm. Mann-Whitney, *U<0.05 and **U<0.01 for drug-treated groups compared with their respective vehicle-treated group. e) Quantitation of MyRF+ oligodendrocytes within human myelinating cortical spheroids following treatment with miconazole and ifenprodil. Spheroids at day 62 were treated with the indicated small molecules for 10 days and stained at day 93. Four spheroids were analyzed per treatment condition, and four fields per organoid were used in the quantitation. f) Representative images of spheroids. Nuclei are labeled with DAPI (blue), and oligodendrocytes are immunostained for MyRF (red). Scale bar, 100 μm.
Figure 4A:
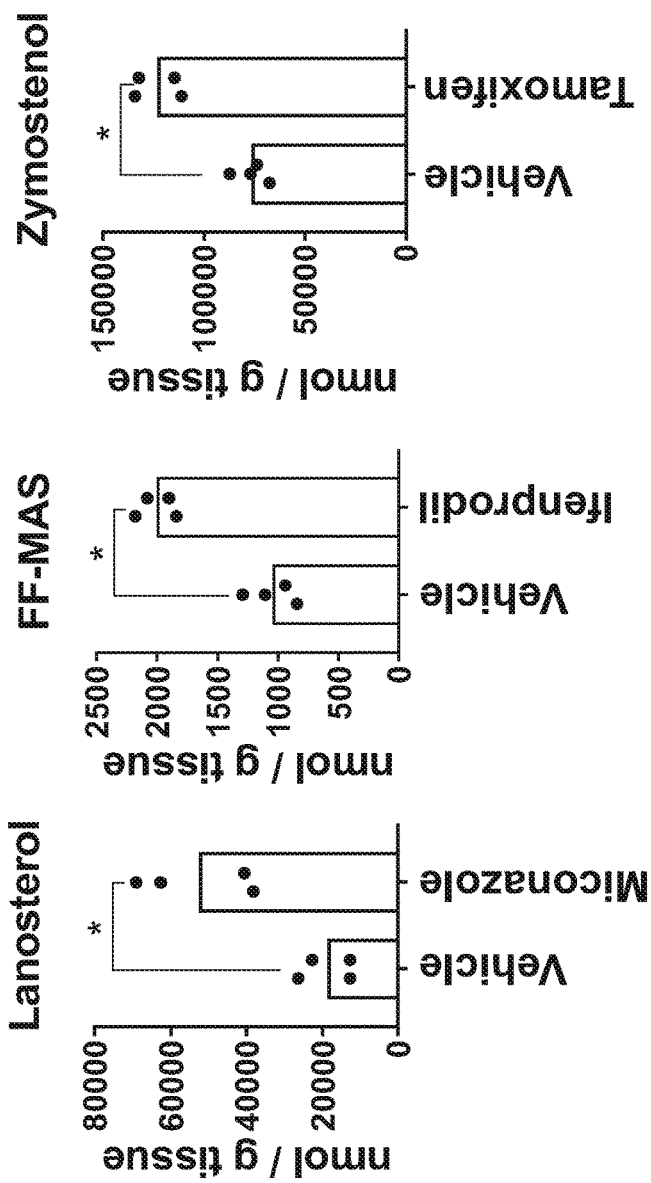

Previously the inventors established that the imidazole antifungal miconazole, which targets CYP51, penetrates the mouse blood brain barrier and enhances remyelination in mouse models of demyelination 4. To assess whether inhibition of other sterol pathway enzymes may also enhance remyelination in vivo, the inventors selected one inhibitor of sterol 14-reductase (ifenprodil) and one inhibitor of EBP (tamoxifen) for further evaluation. Both ifenprodil and tamoxifen are known to cross the mouse blood brain barrier. The inventors first used GC/MS-based sterol profiling to test target engagement in vivo in the CNS. Therapeutic doses of miconazole (10 mg per kg (body weight)) led to significantly elevated lanosterol levels in the brain of adult wild-type mice following 3 days of intraperitoneal dosing (FIG. 4A). Likewise, ifenprodil (10 mg per kg), and tamoxifen (2 mg per kg) each induced significant accumulation of 8,9-unsaturated sterols in vivo in the CNS (FIG. 4A). These data demonstrate that the sterol modulators miconazole, ifenprodil, and tamoxifen can functionally engage CYP51, sterol 14-reductase, and EBP respectively in the mouse CNS.

Previously the inventors demonstrated the positive effects of miconazole on remyelination using a well-established mouse model where injection of lysolecithin is used to create focal lesions of demyelination in the dorsal column white matter of the adult spinal cord. To test whether accumulation of other 8,9-unsaturated sterols enhances remyelination in vivo, the inventors treated lesioned mice with ifenprodil (10 mg per kg) or tamoxifen (2 mg per kg) by daily intraperitoneal injection. Treatment began 4 days after lesion, and the effects on remyelination were quantified histologically 8 days later (FIG. 4B). In vehicle treated animals, profiles of sparsely distributed remyelinating axons characterized by thin myelin sheaths were detected mainly at the periphery of the lesion (FIG. 4C), while ultrastructural analyses revealed unmyelinated axons or axons with a single wrap of myelin (FIG. 4D). By contrast, following 8 days of treatment with ifenprodil or tamoxifen, remyelination was widespread throughout the lesion (FIG. 4C), consistent with a recent report regarding tamoxifen. In both central and peripheral regions of the lesion the majority of axons were surrounded by thin myelin sheaths (FIG. 4D). No obvious differences in axonal diameter were apparent between unmyelinated and myelinated axons, and both small diameter and larger diameter axons appeared equally myelinated in both treatments. Collectively, these data show that small molecule inhibitors of CYP51, sterol 14-reductase, and EBP can significantly enhance remyelination in mice.

Finally, the oligodendrocyte-enhancing and sterol-modulating activities of leading pathway inhibitors are not limited to murine cells but extend to human cells and tissue. The inventors performed sterol profiling in a human glioma cell line and established that these molecules caused accumulation of the expected sterol intermediates. Likewise, miconazole and ifenprodil led to 8,9-unsaturated sterol accumulation within human induced pluripotent stem cell-derived cortical spheroids, further confirming that these molecules similarly engage the sterol synthesis pathway in mouse and human cells and CNS tissue. Importantly, these molecules also enhanced the formation of myelin regulatory factor (MyRF)-positive human oligodendrocytes within myelinating cortical spheroids (FIG. 4E,F). This modified cortical spheroid model enables the inclusion of OPCs as well as their differentiation to myelinating oligodendrocytes.

Although multiple groups have identified small-molecule enhancers of oligodendrocyte formation, a key hurdle to clinical translation of these findings to patients with diseases of white matter is the incomplete understanding of these molecules' functional targets in OPCs. Here the inventors define a dominant mechanism shared by many small molecule enhancers of remyelination: elevation of 8,9-unsaturated sterol intermediate levels by inhibition of a narrow window of cholesterol biosynthesis enzymes spanning CYP51 to EBP. In all the inventors have characterized twenty-seven small molecules with wide-ranging canonical targets as both enhancing myelination and elevating 8,9-unsaturated sterol intermediate levels. Several of these molecules have previously been shown to elevate 8,9-unsaturated sterol levels in mouse CNS cells and in human patients. No molecules have yet been identified that inhibit steps between CYP51 and EBP but are ineffective at enhancing oligodendrocyte formation.

Mechanistically, the inventors provide complementary lines of evidence that support a central signaling role for 8,9-unsaturated sterols in mediating the observed enhanced oligodendrocyte formation. Supplying OPCs with nine independent 8,9-unsaturated sterols was sufficient to enhance the formation of oligodendrocytes. Conversely, conditions that prevented the ketoconazole-mediated accumulation of lanosterol also blocked ketoconazole's ability to enhance oligodendrocyte formation. 8,9-unsaturated sterols have previously been shown to influence a cell fate transition in oocytes, and the work described herein indicates that these 'meisois-activating sterols' also play a novel signaling role during OPC differentiation to oligodendrocytes. While the direct cellular targets of the meiosis-activating sterols remain unclear, the nuclear hormone receptor family and cholesterol homeostasis regulators (SREBP2/LXR) appear to represent unlikely targets.

Myelin is cholesterol-enriched, and past work has established that genetic or pharmacological treatments that inhibit early enzymes in cholesterol biosynthesis, including squalene synthase and HMGCoA reductase, lead to hypomyelination in vivo. The work described herein supports these observations, as statin drugs and a squalene synthesis inhibitor have neutral-to-negative effects on oligodendrocyte formation in the assays (FIG. 2B). These enzymes catalyze steps prior to the synthesis of the first sterol intermediate, so their inhibition prevents the synthesis of all cellular sterols. The inventors' findings establish an alternate paradigm in which the cholesterol biosynthesis pathway can be leveraged to enhance the formation of new oligodendrocytes by targeting later steps whose inhibition does not cause net depletion of cellular sterols. Instead, acute inhibition of CYP51, sterol 14 reductase, or EBP during OPC differentiation induces a 'sterol shift' in which a fraction of cellular cholesterol (30-50% based on our GCMS analysis) is diverted to 8,9-unsaturated sterol intermediates that function as signaling molecules to enhance oligodendrocyte formation. Because cells treated with these cholesterol pathway inhibitors retain a significant pool of free cholesterol in addition to the accumulated 8,9-unsaturated sterols, these inhibitors are compatible with the formation of functional oligodendrocytes that wrap axon-like substrates in vitro and enhance remyelination in vivo. Importantly, the inventors have independently shown that multiple molecules now annotated by us as enhancing 8,9-unsaturated sterol intermediate levels can regenerate functional myelin in vivo, as evidenced by reversal of paralysis in mice with MS-like disease. Ultimately, the work described herein demonstrates that modulating the sterol landscape in OPCs can enhance the formation of oligodendrocytes and points to new therapeutic targets, potent inhibitors for these targets, and metabolite-based biomarkers to accelerate the development of optimal remyelinating therapeutics.

In this Example, the inventors show that regeneration of myelin is mediated by oligodendrocyte progenitor cells (OPCs), an abundant stem cell population in the CNS and the principal source of new myelinating oligodendrocytes. Loss of myelin-producing oligodendrocytes in the central nervous system (CNS) underlies a number of neurological diseases, including multiple sclerosis and diverse genetic diseases. Using high throughput chemical screening approaches, the inventors have identified small molecules that promote myelination by stimulating oligodendrocyte formation from OPCs, and functionally enhance remyelination in vivo. Here, the inventors demonstrate that a broad range of these pro-myelinating molecules function not through their canonical targets but by directly inhibiting CYP51, sterol 14-reductase, and EBP, a narrow range of enzymes within the cholesterol biosynthesis pathway. The inventors found that chemical or genetic inhibition of these enzymes resulted in accumulation of Δ8,9-unsaturated sterol intermediates, which when independently supplied to OPCs enhanced formation of new oligodendrocytes. Functional studies showed that small molecule inhibitors of CYP51, sterol 14-reductase, and EBP induce accumulation of Δ8,9-unsaturated sterols in human brain tissue in vitro and mouse brain tissue in vivo. At the same doses, these molecules also enhance the rate of myelination in vivo in a lysolecithin-induced mouse model of focal demyelination. Collectively, the results described herein provide a unifying mechanism-of-action for most known small-molecule enhancers of oligodendrocyte formation and highlight specific targets for the development of optimal remyelinating therapeutics.

Although multiple groups have identified small-molecule enhancers of oligodendrocyte formation, a key hurdle to clinical translation of these findings to patients with diseases of white matter is the incomplete understanding of these molecules' functional targets in OPCs. Here the inventors define a dominant mechanism shared by many small molecule enhancers of remyelination: elevation of sterol intermediate levels by inhibition of a narrow window of cholesterol biosynthesis enzymes spanning CYP51 to EBP. In all the inventors have characterized twenty-four small molecules with wide-ranging canonical targets as both enhancing myelination and elevating sterol intermediate levels. No molecules have yet been identified that inhibit steps between CYP51 and EBP but are ineffective at enhancing oligodendrocyte formation. Several of these molecules have previously been shown to elevate 8,9-unsaturated sterol levels in mouse CNS cells and in human patients. Supplying OPCs with 8,9-unsaturated sterols was sufficient to enhance the formation of oligodendrocytes, whereas depleting cholesterol levels was ineffective, suggesting that sterol intermediate accumulation plays a positive role in facilitating oligodendrocyte formation from OPCs. Notably, accumulation of 8,9-unsaturated sterol intermediates has been observed in other cell state transitions, and altering the sterol composition of membranes can perturb membrane structure and signaling. Ultimately, the work described herein demonstrates that modulating the sterol landscape in OPCs can enhance the formation of oligodendrocytes and points to new therapeutic targets, potent inhibitors for these targets, and metabolite-based biomarkers to accelerate the development of optimal remyelinating therapeutics.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

What is claimed is:

1. A method of treating a neurodegenerative disease or disorder multiple sclerosis, Alzheimer's disease or Parkinson's disease in a subject wherein myelination or remyelination is beneficial to the subject, the method comprising administering to the subject a therapeutically effective amount of at least one agent that enhances and/or induces accumulation of 8,9-unsaturated sterols in oligodendrocyte progenitor cells (OPCs) and enhances oligodendrocyte generation, and wherein the agent comprising a compound having the formula (III) or a pharmaceutically acceptable salt thereof:

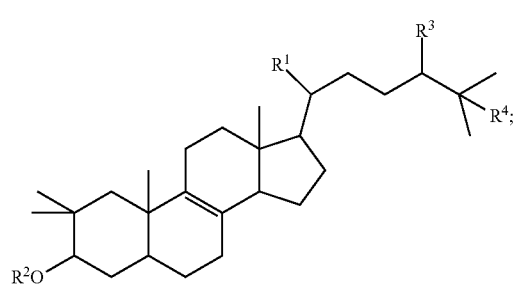

wherein,
(a) $R^1$ is —H or (C1-C3) alkyl;
(b) $R^3$ and $R^4$ are hydrogen or together they designate an additional bond between the carbon atoms to which they are bound; and
(c) $R^2$ is H, an acyl group, a sulphonyl group, a phosphonyl group, or a group which comes together with the remaining part of the molecule forms an ether.

2. The method of claim 1, wherein the agent comprises a compound having the formula (IV) or a pharmaceutically acceptable salt thereof:

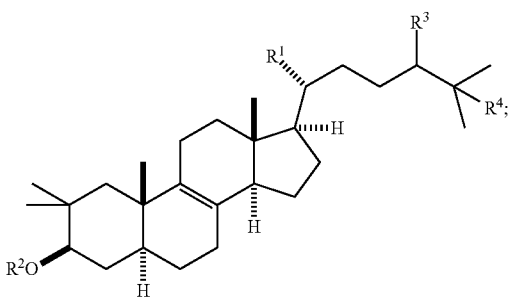

3. The method of claim 1, wherein the agent comprises a compound having the formula (V) or a pharmaceutically acceptable salt thereof:

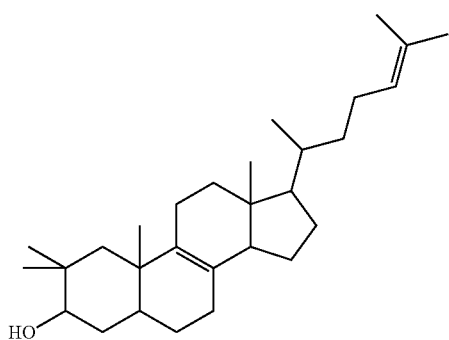 [SMILES: CC(C)=CCCC(C)C1CCC2C3=C(CCC21C)C1(C)CC(C)(C)C(O)CC1CC3]

4. The method of claim 3, wherein the agent comprises a compound having the formula (VI) or a pharmaceutically acceptable salt thereof:

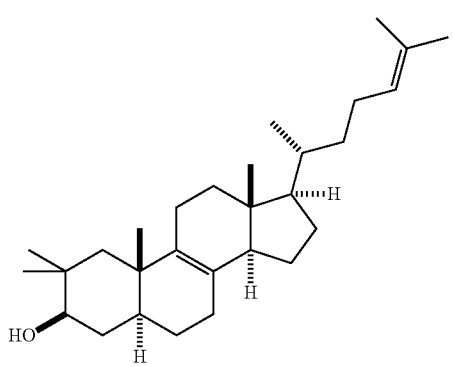 [SMILES: CC(C)=CCC[C@@H](C)[C@H]1CC[C@H]2C3=C(CC[C@]12C)[C@@]1(C)CC(C)(C)[C@H](O)C[C@@H]1CC3]

5. The method of claim 1, wherein the agent induces, promotes, and/or modulates oligodendrocyte precursor cell differentiation, proliferation and/or maturation.

6. The method of claim 5, the induction of OPC differentiation is characterized by an increase of myelin basic protein (MBP) expression.

7. The method of claim 6, wherein the increase of MBP expression is greater than 150% or more compared to a control.

8. The method of claim 1, wherein myelination is promoted in a demyelinated lesion of the subject's central nervous system (CNS).

9. A method of treating multiple sclerosis, Alzheimer's disease or Parkinson's disease in a subject wherein myelination or remyelination is beneficial to the subject, the method comprising administering to the subject a therapeutically effective amount of a compound having the formula (V):

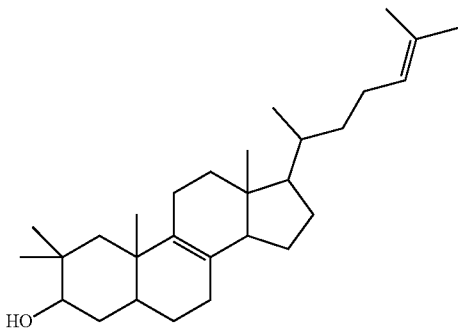 [SMILES: CC(C)=CCCC(C)C1CCC2C3=C(CCC21C)C1(C)CC(C)(C)C(O)CC1CC3]

or a pharmaceutically acceptable salt thereof.

10. The method of claim 9, wherein the compound has the formula (VI):

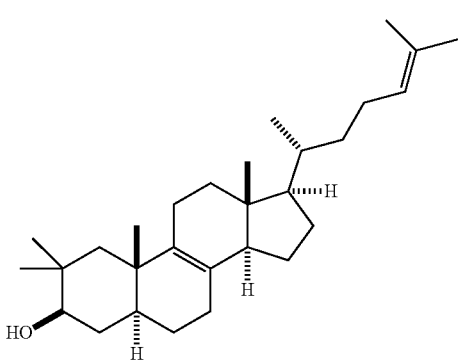 [SMILES: CC(C)=CCC[C@@H](C)[C@H]1CC[C@H]2C3=C(CC[C@]12C)[C@@]1(C)CC(C)(C)[C@H](O)C[C@@H]1CC3]

* * * * *

UNITED STATES PATENT AND TRADEMARK OFFICE
CERTIFICATE OF CORRECTION

PATENT NO. : 12,102,644 B2
APPLICATION NO. : 17/047831
DATED : October 1, 2024
INVENTOR(S) : Drew Adams et al.

It is certified that error appears in the above-identified patent and that said Letters Patent is hereby corrected as shown below:

On the Title Page

Item (60), delete "2019" and insert -- 2018 --

In the Claims

Column 44, Claim 1, Lines 43 and 44, delete "a neurodegenerative disease or disorder"

Column 44, Claim 1, Line 51, delete "comprising" and insert -- comprises --

Column 45, Claim 2, Line 17, delete ";" and insert -- . --

Column 45, Claim 3, Line 44, insert -- . --

Column 45, Claim 4, Line 61, insert -- . --

Column 46, Claim 9, Line 37, insert -- ; --

Column 46, Claim 10, Line 61, insert -- . --

Signed and Sealed this
Seventh Day of January, 2025

Derrick Brent
*Acting Director of the United States Patent and Trademark Office*